(12) United States Patent
Grewal et al.

(10) Patent No.: US 11,981,932 B2
(45) Date of Patent: May 14, 2024

(54) MATERIALS AND METHODS FOR THE MANUFACTURE OF PLURIPOTENT STEM CELLS

(71) Applicant: JANSSEN BIOTECH, INC., Horsham, PA (US)

(72) Inventors: Iqbal S. Grewal, Newtown, PA (US); Rajkumar Ganesan, Blue Bell, PA (US); Sanjaya Singh, Blue Bell, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 10 days.

(21) Appl. No.: 17/349,328

(22) Filed: Jun. 16, 2021

(65) Prior Publication Data

US 2021/0395697 A1   Dec. 23, 2021

Related U.S. Application Data

(60) Provisional application No. 63/040,392, filed on Jun. 17, 2020, provisional application No. 63/040,397, filed on Jun. 17, 2020, provisional application No. 63/040,398, filed on Jun. 17, 2020, provisional application No. 63/040,373, filed on Jun. 17, 2020, provisional application No. 63/040,374, filed on Jun. 17, 2020.

(51) Int. Cl.
*C12N 5/074* (2010.01)
*A61K 35/545* (2015.01)
*C12N 15/86* (2006.01)

(52) U.S. Cl.
CPC ......... *C12N 5/0696* (2013.01); *A61K 35/545* (2013.01); *C12N 15/86* (2013.01); *C12N 2501/2315* (2013.01); *C12N 2501/999* (2013.01); *C12N 2502/1114* (2013.01)

(58) Field of Classification Search
None
See application file for complete search history.

(56) References Cited

U.S. PATENT DOCUMENTS

| | | | |
|---|---|---|---|
| 4,526,938 A | 7/1985 | Churchill | |
| 4,642,120 A | 2/1987 | Nevo et al. | |
| 4,690,915 A | 9/1987 | Rosenberg | |
| 4,846,835 A | 7/1989 | Grande | |
| 5,041,138 A | 8/1991 | Vacanti et al. | |
| 5,128,326 A | 7/1992 | Balazs et al. | |
| 5,225,539 A | 7/1993 | Winter | |
| 5,530,101 A | 6/1996 | Queen et al. | |
| 5,565,332 A | 10/1996 | Hoogenboom | |
| 5,585,089 A | 12/1996 | Queen et al. | |
| 5,646,008 A | 7/1997 | Thompson et al. | |
| 5,679,377 A | 10/1997 | Bernstein et al. | |
| 5,698,446 A | 12/1997 | Klump et al. | |
| 5,766,886 A | 6/1998 | Studnicka et al. | |
| 5,770,196 A | 6/1998 | Studnicka | |
| 5,786,217 A | 7/1998 | Tubo et al. | |
| 5,821,123 A | 10/1998 | Studnicka | |
| 5,869,619 A | 2/1999 | Studnicka | |
| 5,912,015 A | 6/1999 | Bernstein et al. | |
| 5,916,597 A | 6/1999 | Lee et al. | |
| 5,989,463 A | 11/1999 | Tracy et al. | |
| 6,407,213 B1 | 6/2002 | Carter et al. | |
| 7,052,906 B1 | 5/2006 | Lawson et al. | |
| 7,371,849 B2 | 5/2008 | Honda et al. | |
| 7,741,465 B1 | 6/2010 | Eshhar et al. | |
| 8,754,287 B2 | 6/2014 | MacDonald et al. | |
| 2003/0170238 A1 | 9/2003 | Gruenberg et al. | |
| 2005/0042664 A1 | 2/2005 | Wu et al. | |
| 2009/0307787 A1 | 12/2009 | Grosveld et al. | |
| 2010/0122358 A1 | 5/2010 | Brüggemann et al. | |
| 2015/0289489 A1 | 10/2015 | MacDonald et al. | |
| 2015/0299317 A1 | 10/2015 | Orentas et al. | |
| 2018/0170982 A1 | 6/2018 | West et al. | |
| 2019/0359940 A1* | 11/2019 | Zeng ................... | C12N 5/0636 |
| 2020/0017837 A1 | 1/2020 | Aoi | |

FOREIGN PATENT DOCUMENTS

| | | |
|---|---|---|
| EP | 0239400 A2 | 9/1987 |
| EP | 0368684 A1 | 5/1990 |
| EP | 0519596 A1 | 12/1992 |
| EP | 0368684 B1 | 3/1994 |
| EP | 0592106 A1 | 4/1994 |
| EP | 0368684 B2 | 9/2004 |
| EP | 0592106 B1 | 11/2004 |

(Continued)

OTHER PUBLICATIONS

Van Acker et al. Interleukin-15 enhances the proliferation, stimulatory phenotype, and antitumor effector functions of human gamma delta Tcells. Journal of Hematology & Oncology (2016) 9:101. (Year: 2016).*

Zeng et al. Derivation of mimetic γδ T cells endowed with cancer recognition receptors from reprogrammed γδ T cell. PLoS One (2019) 14:5. (Year: 2019).*

Komatsu et al. RNA Virus-Based Episomal Vector with a Fail-Safe Switch Facilitating Efficient Genetic Modification and Differentiation of iPSCs. Molecular Therapy: Methods & Clinical Development (2019) 14. (Year: 2019).*

Watanabe D, Koyanagi-Aoi M, Taniguchi-Ikeda M, Yoshida Y, Azuma T, Aoi T. The Generation of Human γδT Cell-Derived Induced Pluripotent Stem Cells from Whole Peripheral Blood Mononuclear Cell Culture. Stem Cells Transl Med. Jan. 2018;7(1):34-44. doi: 10.1002/sctm. 17-0021. Epub Nov. 21, 2017. (Year: 2017).*

(Continued)

*Primary Examiner* — Allison M Fox
*Assistant Examiner* — Alyssa G Weston
(74) *Attorney, Agent, or Firm* — Troutman Pepper Hamilton Sanders LLP

(57) ABSTRACT

Provided here in are methods of producing induced pluripotent stem cells (iPSCs) and isolated population of produced induced pluripotent stem cells (iPSCs). Also provided herein are methods of treating a subject in need thereof using the produced iPSCs or pharmaceutical compositions comprising the produced iPSCs.

12 Claims, 19 Drawing Sheets

Figure 1:
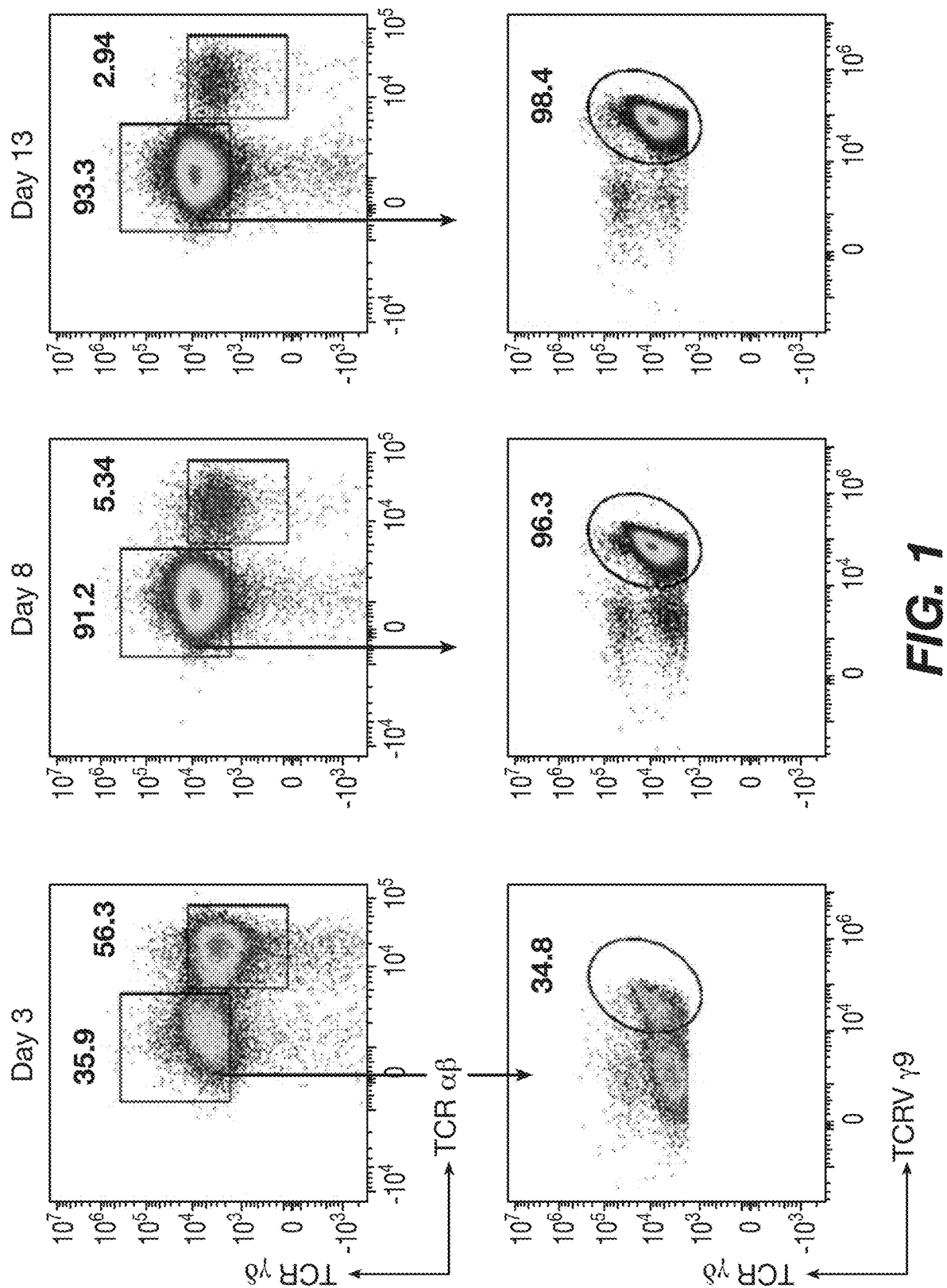

Specification includes a Sequence Listing.

(56) References Cited

FOREIGN PATENT DOCUMENTS

| EP | 0519596 B1 | 2/2005 |
|---|---|---|
| WO | WO 1991005548 A1 | 5/1991 |
| WO | WO 1991009967 A1 | 7/1991 |
| WO | WO 1993011794 A1 | 6/1993 |
| WO | WO 1993017105 A1 | 9/1993 |
| WO | WO 1994404678 A1 | 3/1994 |
| WO | WO 1996020698 A2 | 7/1996 |
| WO | WO 1996020698 A3 | 7/1996 |
| WO | WO 1996034103 A1 | 10/1996 |
| WO | WO 1999015154 A1 | 4/1999 |
| WO | WO 1999020253 A1 | 4/1999 |
| WO | WO 1999037681 A2 | 7/1999 |
| WO | WO 1999037681 A3 | 7/1999 |
| WO | WO 2003014161 A2 | 2/2000 |
| WO | WO 2000032776 A2 | 6/2000 |
| WO | WO 2000032776 A3 | 6/2000 |
| WO | WO 2000043507 A1 | 7/2000 |
| WO | WO 2001090190 A2 | 11/2001 |
| WO | WO 2001090190 A3 | 11/2001 |
| WO | WO 2003014161 A3 | 2/2003 |
| WO | WO 2003025020 A1 | 3/2003 |
| WO | WO 2003035694 A2 | 5/2003 |
| WO | WO 2003035694 A3 | 5/2003 |
| WO | WO 2004049794 A2 | 6/2004 |
| WO | WO 2004049794 A3 | 6/2004 |
| WO | WO 2006003388 A2 | 1/2006 |
| WO | WO 2006003388 A3 | 1/2006 |
| WO | WO 2006030220 A1 | 3/2006 |
| WO | WO 2015158671 A1 | 10/2015 |
| WO | WO 2016014789 A2 | 1/2016 |
| WO | WO 2016014789 A3 | 1/2016 |
| WO | WO 2016102965 A1 | 6/2016 |
| WO | WO 2018067992 A1 | 4/2018 |

OTHER PUBLICATIONS

Tan WK, Tay JCK, Zeng J, Zheng M, Wang S. Expansion of Gamma Delta T Cells—A Short Review on Bisphosphonate and K562-Based Methods. J Immunol Sci. (2018); 2(3): 6-12. (Year: 2018).*
Allen et al., 1989, "Acute eosinophilic pneumonia as a reversible cause of noninfectious respiratory failure," N. Engl. J. Med., 321(9):569-574.
Aran et al., 2019, "Reference-based analysis of lung single-cell sequencing reveals a transitional profibrotic macrophage," Nat. Immunol., 20(2):163-172 and Methods (15 pages).
Atala, 1999, "Engineering tissues and organs," Curr. Opin. Urol., 9(6):517-526.
Baca et al., 1997, "Antibody humanization using monovalent phage display," J. Biol. Chem., 272(16):10678-10684.
Bain et al., 1995, "Embryonic stem cells express neuronal properties in vitro," Dev. Biol., 168(2):342-357.
Bird et al., 1988, "Single-chain antigen-binding proteins," Science, 242(4877):423-426.
Brenner et al., 2010, "Adoptive T cell therapy of cancer," Curr. Opin. Immunol., 22(2):251-257.
Brinster et al., 1982, "Regulation of metallothionein—thymidine kinase fusion plasmids injected into mouse eggs," Nature, 296(5852):39-42.
Buchwald et al., 1980, "Long-term, continuous intravenous heparin administration by an implantable infusion pump in ambulatory patients with recurrent venous thrombosis," Surgery, 88(4):507-516.
Caldas et al., 2000, "Design and synthesis of germline-based hemi-humanized single-chain Fv against the CD18 surface antigen," Protein Eng., 13(5):353-360.
Carter et al., 1992, "Humanization of an anti-p185HER2 antibody for human cancer therapy," Proc. Natl. Acad. Sci. USA, 89(10):4285-4289.
Chothia et al., 1987, "Canonical structures for the hypervariable regions of immunoglobulins," J. Mol. Biol., 196(4):901-917.
Cleek et al., 1997, "Biodegradable polymeric carriers for a bFGF antibody for cardiovascular application," Pro. Int. Symp. Control. Rel. Bioact. Mater., 24:853-854.
Colcher et al., 1990, "In vivo tumor targeting of a recombinant single-chain antigen-binding protein," J. Natl. Cancer Inst., 82(14):1191-1197.
Corbeil et al., 1998, "AC133 hematopoietic stem cell antigen: human homologue of mouse kidney prominin or distinct member of a novel protein family?" Blood, 91(7):2625-2626.
Couto et al., 1995, "Anti-BA46 monoclonal antibody Mc3: humanization using a novel positional consensus and in vivo and in vitro characterization," Cancer Res., 55(8):1717-1722.
Couto et al., 1995, "Designing human consensus antibodies with minimal positional templates," Cancer Res., 55(23 Suppl):5973s-5977s.
Dahlstrand et al., 1992, "Characterization of the human nestin gene reveals a close evolutionary relationship to neurofilaments," J. Cell Sci., 103 (Pt 2):589-597.
Dall'Acqua et al., 2005, "Antibody humanization by framework shuffling," Methods, 36(1):43-60.
Damschroder et al., 2007, "Framework shuffling of antibodies to reduce immunogenicity and manipulate functional and biophysical properties," Mol. Immunol., 44(11):3049-3060.
Davies et al., 1994, "'Camelising' human antibody fragments: NMR studies on VH domains," FEBS Lett., 339(3):285-290.
Davies et al., 1996, "Single antibody domains as small recognition units: design and in vitro antigen selection of camelized, human VH domains with improved protein stability," Protein Eng., 9(6):531-537.
Davila et al., 2013, "CD19 CAR-targeted T cells induce long-term remission and B Cell Aplasia in an immunocompetent mouse model of B cell acute lymphoblastic leukemia," PLoS One, 8(4):e61338 (14 pages).
De Groot et al., 2006, "Evolutionary deimmunization: an ancillary mechanism for self-tolerance?" Cell Immunol., 244(2):148-153.
Dennis et al., 2003, "DAVID: Database for Annotation, Visualization, and Integrated Discovery," Genome Biol., 4(9):R60 (11 pages).
Dufner et al., 2006, "Harnessing phage and ribosome display for antibody optimisation," Trends Biotechnol., 24(11):523-529.
Duprey et al., 1988, "A mouse gene homologous to the *Drosophila* gene caudal is expressed in epithelial cells from the embryonic intestine," Genes Dev., 2(12A):1647-1654.
During et al., 1989, "Controlled release of dopamine from a polymeric brain implant: in vivo characterization," Ann. Neurol., 25(4):351-356.
Feldhaus et al., 2003, "Flow-cytometric isolation of human antibodies from a nonimmune *Saccharomyces cerevisiae* surface display library," Nat. Biotechnol., 21(2):163-170.
Floyd et al., 1999, "Combinatorial chemistry as a tool for drug discovery," Prog. Med. Chem., 36:91-168.
Foote et al., 1992, "Antibody framework residues affecting the conformation of the hypervariable loops," J. Mol. Biol., 224(2):487-499.
Gossen et al., 1995, "Transcriptional activation by tetracyclines in mammalian cells," Science, 268(5218):1766-1769.
Guex et al., 1997, "Swiss-Model and the Swiss-Pdb Viewer: an environment for comparative protein modeling," Electrophoresis, 18(15):2714-2723.
Hamers-Casterman et al., 1993, "Naturally occurring antibodies devoid of light chains," Nature, 363(6428):446-448.
Hermans et al., 2004, "The Vital assay: a versatile fluorometric technique for assessing CTL- and NKT-mediated cytotoxicity against multiple targets in vitro and in vivo," J. Immunol. Methods, 285(1):25-40.
Holt et al., 2003, "Domain antibodies: proteins for therapy," Trends Biotechnol., 21(11):484-490.
Hoogenboom, 2005, "Selecting and screening recombinant antibody libraries," Nat. Biotechnol., 23(9):1105-1116.
Howard III et al., 1989, "Intracerebral drug delivery in rats with lesion-induced memory deficits," J. Neurosurg., 71(1):105-112.
Huston et al., 1993, "Antigen recognition and targeted delivery by the single-chain Fv," Cell Biophys., 22(1-3):189-224.

(56) References Cited

OTHER PUBLICATIONS

International Search Report and Written Opinion for International Patent Application No. PCT/US2021/037594 (Pub No. WO 2021257679) dated Nov. 5, 2021 (9 pages).
Israel et al., 1989, "Highly inducible expression from vectors containing multiple GRE's in CHO cells overexpressing the glucocorticoid receptor," Nucleic Acids Res., 17(12): 4589-4604.
Ivanova et al., 2002, "A stem cell molecular signature," Science, 298(5593):601-604.
Jones et al., 1986, "Replacing the complementarity-determining regions in a human antibody with those from a mouse," Nature, 321(6069):522-525.
Jones et al., 2009, "Deimmunization of monoclonal antibodies," Methods Mol. Biol., 525:405-423, xiv (19 pages).
Kaji et al., 2009, "Virus-free induction of pluripotency and subsequent excision of reprogramming factors," Nature, 458(7239): 771-775 and Methods (6 pages).
Kakimi et al., 2014, "γδ T cell therapy for the treatment of non-small cell lung cancer," Transl Lung Cancer Res., 3(1):23-33.
Kalyan et al., 2013, "Defining the nature of human γδ T cells: a biographical sketch of the highly empathetic," Cell Mol. Immunol., 10(1):21-29 (Epub 2012).
Kannagi et al., 1983, "Stage-specific embryonic antigens (SSEA-3 and -4) are epitopes of a unique globo-series ganglioside isolated from human teratocarcinoma cells," EMBO J., 2(12):2355-2361.
Karagiannis et al., 2016, "Reprogramming away from the exhausted T cell state," Semin. Immunol., 28(1):35-44 (Epub 2015).
Kashmiri et al., 2005, "SDR grafting—a new approach to antibody humanization," Methods, 36(1):25-34.
Kastenberg et al., 2008, "Alternative sources of pluripotency: science, ethics, and stem cells," Transplant Rev (Orlando), 22(3):215-222.
Klock et al., 1987, "Oestrogen and glucocorticoid responsive elements are closely related but distinct," Nature, 329(6141):734-736.
Kochenderfer et al., 2009, "Construction and preclinical evaluation of an anti-CD19 chimeric antigen receptor," J. Immunother., 32(7):689-702.
Korinek et al., 1998, "Depletion of epithelial stem-cell compartments in the small intestine of mice lacking Tcf-4," Nat. Genet., 19(4):379-383.
Korsunsky et al., 2019, "Fast, sensitive and accurate integration of single-cell data with Harmony," Nat. Methods, 16(12):1289-1296 and Methods (16 pages).
Kosti et al., 2021, "Generation of hypoxia-sensing chimeric antigen receptor T cells," STAR Protoc., 2(3):100723 (21 pages).
Kosti et al., 2021, "Hypoxia-sensing CAR T cells provide safety and efficacy in treating solid tumors," Cell Rep. Med., 2(4):100227 (17 pages).
Lam et al., 1997, "Microencapsulation of recombinant humanized monoclonal antibody for local delivery," Proc. Intl. Symp. Control Rel. Bioact. Mater, 24:759-760.
Langer et al., 1983, "Chemical and Physical Structure of Polymers as Carriers for Controlled Release of Bioactive Agents: A Review," Journal of Macromolecular Science-reviews in Macromolecular Chemistry and Physics, 23(1):61-126.
Langer, 1990, "New methods of drug delivery," Science, 249(4976): 1527-1533.
Lazar et al., 2007, "A molecular immunology approach to antibody humanization and functional optimization," Mol. Immunol., 44(8):1986-1998 (Epub 2006).
Lee et al., 1981, "Glucocorticoids regulate expression of dihydrofolate reductase cDNA in mouse mammary tumour virus chimaeric plasmids," Nature, 294(5838):228-232.
Lee et al., 1988, "Glucocorticoids selectively inhibit the transcription of the interleukin 1 beta gene and decrease the stability of interleukin 1 beta mRNA," Proc. Natl. Acad. Sci. USA, 85(4):1204-1208.
Lee et al., 1999, "A possible role for the high mobility group box transcription factor Tcf-4 in vertebrate gut epithelial cell differentiation," J. Biol. Chem., 274(3):1566-1572.
Lendahl et al., 1990, "CNS stem cells express a new class of intermediate filament protein," Cell, 60(4):585-595.
Levy et al., 1985, "Inhibition of calcification of bioprosthetic heart valves by local controlled-release diphosphonate," Science, 228(4696):190-192.
Luecken et al., 2019, "Current best practices in single-cell RNA-seq analysis: a tutorial," Mol. Syst. Biol., 15(6):e8746 (23 pages).
Lundberg et al., 1996, "Generation of DOPA-producing astrocytes by retroviral transduction of the human tyrosine hydroxylase gene: in vitro characterization and in vivo effects in the rat Parkinson model," Exp. Neurol., 139(1):39-53.
Maherali et al., 2007, "Directly reprogrammed fibroblasts show global epigenetic remodeling and widespread tissue contribution," Cell Stem Cell, 1(1):55-70.
Matoba et al., 2018, "Somatic Cell Nuclear Transfer Reprogramming: Mechanisms and Applications," Cell Stem Cell, 23(4):471-485.
McInnes et al., 2018, "UMAP: Uniform Manifold Approximation and Projection for Dimension Reduction," arXiv:1802.03426 v1, Feb. 9, 2018 (18 pages).
McInnes et al., 2018, "UMAP: Uniform Manifold Approximation and Projection for Dimension Reduction," arXiv:1802.03426 v2, Dec. 6, 2018 (51 pages).
McInnes et al., 2020, "UMAP: Uniform Manifold Approximation and Projection for Dimension Reduction," arXiv:1802.03426 v3, Sep. 18, 2020 (63 pages).
Milone et al., 2009, "Chimeric receptors containing CD137 signal transduction domains mediate enhanced survival of T cells and increased antileukemic efficacy in vivo," Mol. Ther., 17(8):1453-1464.
Milstein et al., 1983, "Hybrid hybridomas and their use in immunohistochemistry," Nature, 305(5934):537-540.
Morea et al., 2000, "Antibody modeling: implications for engineering and design," Methods, 20(3):267-279.
Mulligan et al., 1993, "The basic science of gene therapy," Science, 260(5110):926-932.
Ning et al., 1996, "Intratumoral radioimmunotherapy of a human colon cancer xenograft using a sustained-release gel," Radiother Oncol., 39(2):179-189.
Okita et al., 2008, "Generation of mouse induced pluripotent stem cells without viral vectors," Science, 322(5903):949-953.
Ou et al., 2021, "Dichotomous and stable gamma delta T-cell number and function in healthy individuals," J. Immunother Cancer, 9(5):e002274 (13 pages).
Padlan et al., 1995, "Identification of specificity-determining residues in antibodies," FASEB J., 9(1):133-139.
Padlan, 1991, "A possible procedure for reducing the immunogenicity of antibody variable domains while preserving their ligand-binding properties," Mol. Immunol., 28(4-5):489-498.
Palacios et al., 1995, "In vitro generation of hematopoietic stem cells from an embryonic stem cell line," Proc. Natl. Acad. Sci. USA, 92(16):7530-7534.
Pease et al., 1990, "Isolation of embryonic stem (ES) cells in media supplemented with recombinant leukemia inhibitory factor (LIF)," Dev. Biol., 141(2):344-352.
Pedersen et al., 1994, "Comparison of surface accessible residues in human and murine immunoglobulin Fv domains. Implication for humanization of murine antibodies," J. Mol. Biol., 235(3):959-973.
Pedersen, 1994, "Studies of in vitro differentiation with embryonic stem cells," Reprod. Fertil. Dev., 6(5):543-552.
Pluckthun et al., 1989, "Expression of functional antibody Fv and Fab fragments in *Escherichia coli*," Methods Enzymol., 178:497-515.
Presta et al., 1993, "Humanization of an antibody directed against IgE," J. Immunol., 151(5):2623-2632.
Ramalho-Santos et al., 2002, ""Stemness": transcriptional profiling of embryonic and adult stem cells," Science. 298(5593):597-600.
Riechmann et al., 1988, "Reshaping human antibodies for therapy," Nature, 332(6162):323-327.
Riechmann et al., 1999, "Single domain antibodies: comparison of camel VH and camelised human VH domains," J. Immunol. Methods, 231(1-2):25-38.

(56) References Cited

OTHER PUBLICATIONS

Riechmann, 1996, "Rearrangement of the former VL interface in the solution structure of a camelised, single antibody VH domain," J. Mol. Biol., 259(5):957-969.
Roguska et al., 1994, "Humanization of murine monoclonal antibodies through variable domain resurfacing," Proc. Natl. Acad. Sci. USA, 91(3):969-973.
Roguska et al., 1996, "A comparison of two murine monoclonal antibodies humanized by CDR-grafting and variable domain resurfacing," Protein Eng., 9(10):895-904.
Rosenberg et al., 2008, "Adoptive cell transfer: a clinical path to effective cancer immunotherapy," Nat. Rev. Cancer, 8(4):299-308.
Rosenberg, 2011, "Cell transfer immunotherapy for metastatic solid cancer—what clinicians need to know," Nat. Rev. Clin. Oncol., 8(10):577-585.
Ruella et al., 2017, "Next-Generation Chimeric Antigen Receptor T-Cell Therapy: Going off the Shelf," BioDrugs, 31(6):473-481.
Sali et al., 1993, "Comparative protein modelling by satisfaction of spatial restraints," J. Mol. Biol., 234(3):779-815.
Sandhu, 1994, "A rapid procedure for the humanization of monoclonal antibodies," Gene., 150(2):409-410.
Sarkar et al., 2013, "Hypoxia induced impairment of NK cell cytotoxicity against multiple myeloma can be overcome by IL-2 activation of the NK cells," PLoS One, 8(5):e64835 (12 pages).
Schietinger et al., 2014, "Tolerance and exhaustion: defining mechanisms of T cell dysfunction," Trends Immunol., 35(2):51-60 (Epub 2013).
Schlapschy et al., 2004, "Functional humanization of an anti-CD30 Fab fragment for the immunotherapy of Hodgkin's lymphoma using an in vitro evolution approach," Protein Eng. Des. Sel., 17(12):847-860.
Sefton, 1987, "Implantable pumps," Crit. Rev. Biomed. Eng., 14(3):201-240.
Silva-Santos et al., 2015, "γδ T cells in cancer," Nat. Rev. Immunol., 15(11):683-691.
Sims et al., 1993, "A humanized CD18 antibody can block function without cell destruction," J. Immunol., 151(4):2296-2308.
Soldner et al., 2009, "Parkinson's disease patient-derived induced pluripotent stem cells free of viral reprogramming factors," Cell, 136(5):964-977.
Solter et al., 1978, "Monoclonal antibody defining a stage-specific mouse embryonic antigen (SSEA-1)," Proc. Natl. Acad. Sci. USA, 75(11):5565-5569.
Song et al., 1996, "Antibody mediated lung targeting of long-circulating emulsions," PDA J. Pharm. Sci. Technol., 50(6):372-377.
Stadtfeld et al., 2008, "Induced pluripotent stem cells generated without viral integration," Science, 322(5903):945-949.
Streltsov et al., 2005, "Structure of a shark IgNAR antibody variable domain and modeling of an early-developmental isotype," Protein Sci., 14(11):2901-2909.
Studnicka et al., 1994, "Human-engineered monoclonal antibodies retain full specific binding activity by preserving non-CDR complementarity-modulating residues," Protein Eng., 7(6):805-814.
Subramanian et al., 1998, "The murine Cdx1 gene product localises to the proliferative compartment in the developing and regenerating intestinal epithelium," Differentiation, 64(1):11-18.
Takahashi et al., 2006, "Induction of pluripotent stem cells from mouse embryonic and adult fibroblast cultures by defined factors," Cell, 126(4):663-676.
Takahashi et al., 2016, "A decade of transcription factor-mediated reprogramming to pluripotency," Nat. Rev. Mol. Cell Biol., 17(3):183-193.

Tan et al., 1998, "Stereoselective Synthesis of over Two Million Compounds Having Structural Features Both Reminiscent of Natural Products and Compatible with Miniaturized Cell-Based Assays," J. Am. Chem. Soc., 120(33):8565-8566.
Tan et al., 2002, ""Superhumanized" antibodies: reduction of immunogenic potential by complementarity-determining region grafting with human germline sequences: application to an anti-CD28," J. Immunol., 169(2):1119-1125.
Themeli et al., 2013, "Generation of tumor-targeted human T lymphocytes from induced pluripotent stem cells for cancer therapy," Nat. Biotechnol., 31(10):928-933 and Online Methods (8 pages).
Tsukahara et al., 2013, "CD19 target-engineered T-cells accumulate at tumor lesions in human B-cell lymphoma xenograft mouse models," Biochem. Biophys. Res. Commun., 438(1):84-89.
Tyler et al.., 2015, "Human Vγ9/Vδ2 T cells: Innate adaptors of the immune system," Cell Immunol., 296(1):10-21.
Verhoeyen et al., 1988, "Reshaping human antibodies: grafting an antilysozyme activity," Science, 239(4847):1534-1536.
Wakayama et al., 1998, "Full-term development of mice from enucleated oocytes injected with cumulus cell nuclei," Nature, 394(6691):369-374.
Ward et al., 1989, "Binding activities of a repertoire of single immunoglobulin variable domains secreted from *Escherichia coli*," Nature, 341(6242):544-546.
Watanabe et al., 2018, "The Generation of Human γδ T Cell-Derived Induced Pluripotent Stem Cells from Whole Peripheral Blood Mononuclear Cell Culture," Stem Cells Transl. Med., 7(1):34-44 (Epub 2017).
Weigmann et al., 1997, "Prominin, a novel microvilli-specific polytopic membrane protein of the apical surface of epithelial cells, is targeted to plasmalemmal protrusions of non-epithelial cells," Proc. Natl. Acad. Sci. USA, 94(23): 12425-12430.
Weinreb et al., 2018, "SPRING: a kinetic interface for visualizing high dimensional single-cell expression data," Bioinformatics, 34(7):1246-1248.
Wernig et al., 2007, "In vitro reprogramming of fibroblasts into a pluripotent ES-cell-like state," Nature, 448(7151):318-324 and Methods (8 pages).
Whitelegg et al., 2000, "WAM: an improved algorithm for modelling antibodies on the WEB," Protein Eng., 13(12):819-824.
Wilmut et al., 1997, "Viable offspring derived from fetal and adult mammalian cells," Nature, 385(6619):810-813.
Wobus et al., 1984, "Characterization of a pluripotent stem cell line derived from a mouse embryo," Exp. Cell Res., 152(1):212-219.
Wolf et al., 2018, "SCANPY: large-scale single-cell gene expression data analysis," Genome. Biol., 19(1):15 (5 pages).
Woltjen et al., 2009, "piggyBac transposition reprograms fibroblasts to induced pluripotent stem cells," Nature, 458(7239):766-770 and Methods (6 pages).
Yoshimoto et al., 1995, "Astrocytes retrovirally transduced with BDNF elicit behavioral improvement in a rat model of Parkinson's disease," Brain Res., 691(1-2):25-36.
Yu et al., 2009, "Human induced pluripotent stem cells free of vector and transgene sequences," Science, 324(5928):797-801.
Yusa et al., 2009, "Generation of transgene-free induced pluripotent mouse stem cells by the piggyBac transposon," Nat. Methods, 6(5):363-369 and Online Methods (9 pages).
Zambrowicz et al., 1997, "Disruption of overlapping transcripts in the ROSA beta geo 26 gene trap strain leads to widespread expression of beta-galactosidase in mouse embryos and hematopoietic cells," Proc. Natl. Acad. Sci. USA, 94(8):3789-3794.
Rigau, et al., 2020, "Butyrophilin 2A1 is essential for phosphoantigen reactivity by γδ T cells," Science 367, 642.

\* cited by examiner

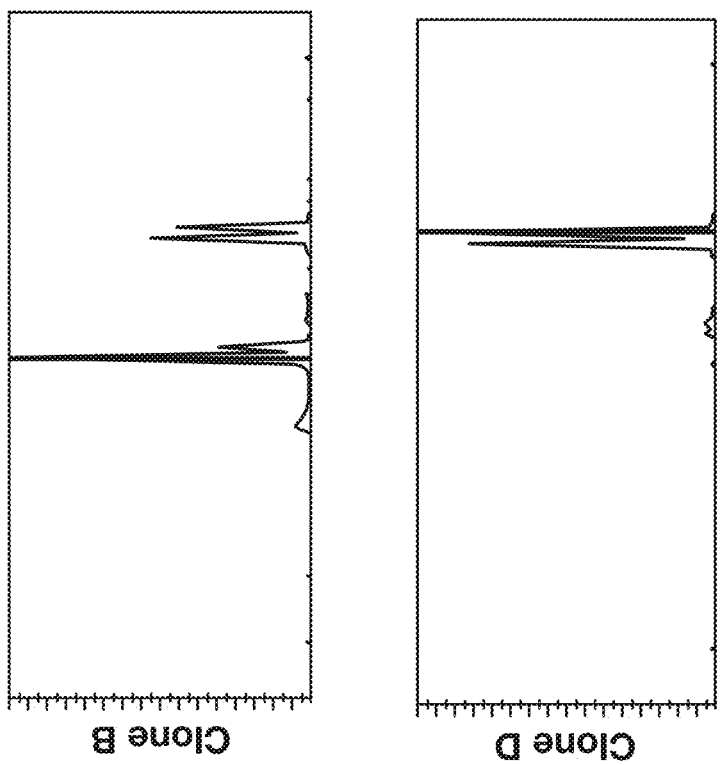
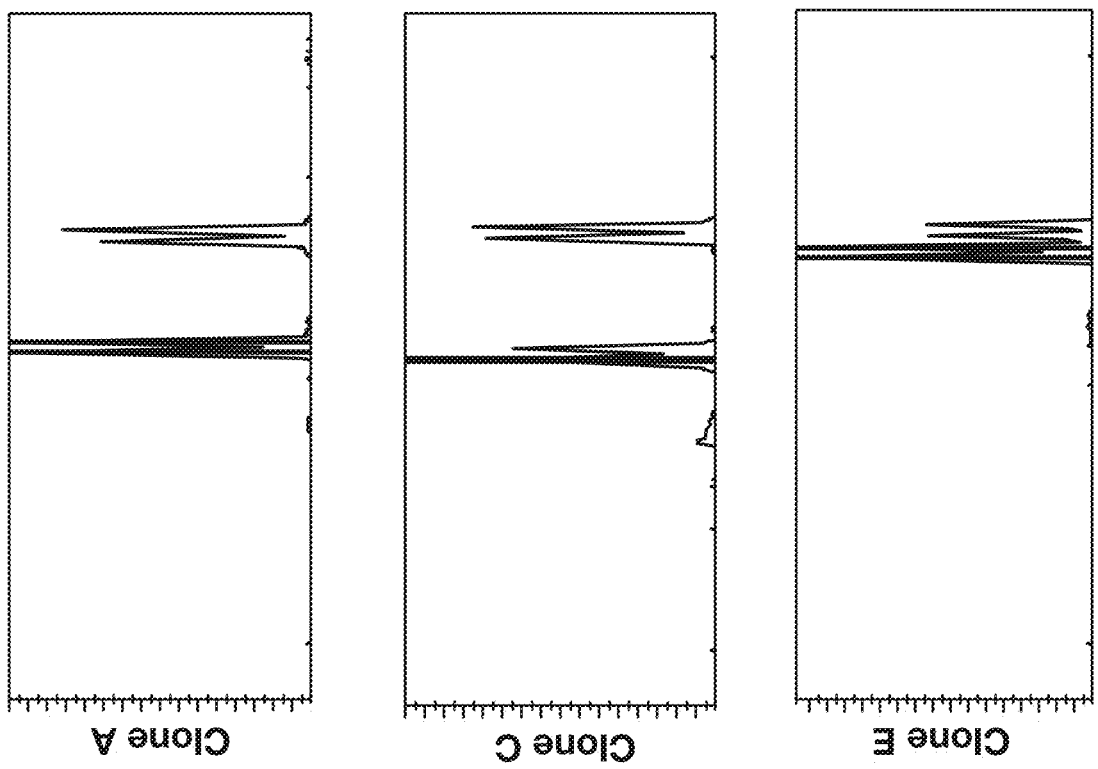
FIG. 3

Clone B

Vγ9 amplicon sequence:

GCAACATCTGTATATTGGTATGAGAGAGACCTGGTGAAGTCATACAGTTCCTGGTGTCCATTTCATATGACGGCACTGTCAGAA
AGGAATCCGGCATTCCGTCAGGCAAATTTGAGGTGAAGTAGGATACCTGAAACGTCTACACTCTCACCATTCACAATGTAGA
GAAACAGGACATAGCTACCTACTGTGCCTTGTGGGAGACACAAGAGTTGGGCAAAAAAATCAAGGTATTTGGTCCCGGAAC
AAAG (SEQ ID NO: 7)

1a. blastn (sequence alignment for Vγ9 amplicon sequence)

```
Query     1  GCAACATCTGTATATTGGTATGAGAGAGACCTGGTGAAGTCATACAGTTCCTGGTGTCC    60
             ||||||||||||||||||||||||||||||||||||||||||||||||||||||||||||
Sbjct    94  GCAACATCTGTATATTGGTATGAGAGAGACCTGGTGAAGTCATACAGTTCCTGGTGTCC   153

Query    61  ATTTCATATGACGGCACTGTCAGAAAGGAATCCGGCATTCCGTCAGGCAAATTTGAGGTG   120
             ||||||||||||||||||||||||||||||||||||||||||||||||||||||||||||
Sbjct   154  ATTTCATATGACGGCACTGTCAGAAAGGAATCCGGCATTCCGTCAGGCAAATTTGAGGTG   213

Query   121  GATAGGATACCTGAAACGTCTACATCCACTCACTCTCACAATGTAGAGAAACAGGAC      180
             ||||||||||||||||||||||||||||||||||||||||||||||||||||||||||
Sbjct   214  GATAGGATACCTGAAACGTCTACATCCTCACATTCACCATTCACAATGTAGAAACAGGAC   273

Query   181  ATAGCTACCTACTGTGCCTTGTGGGAGACACAAGAGTTGGGCAAAAAAATCAAGGTA      240
             ||||||||||||||||||||||||||||||||||||||||||||||||||||||||||
Sbjct   274  ATAGCTACCTACTGTGCCTTGTGGGAGACACAAGAGTTGGGCAAAAAAATCAAGGTA     333

Query   241  TTTGGTCCCGGAACAAAG     258  (SEQ ID NO: 7)
             ||||||||||||||||||
Sbjct   334  TTTGGTCCCGGAACAAAG     351  (SEQ ID NO: 8)
```

FIG. 5

Vδ2 amplicon sequence:

GCCCTTATACCGAGAAAGGACACATCTATGGCCCTGTGTTTCAAAGACAATTTCCAAGGTGACATTGATATTGCAAAGAACCTGGCT
GTACTTAAGATACTTGCACCATCAGAGAGAGATGAAGGTCTTACTACTGTCCTGTGACACCGTAAATGGGGGATACGCGGTC
ACCGATAAACTCATCTTTGGAAAAGGAACCCGTGTGACTGTGGAACAAGGC (SEQ ID NO: 9)

2a. blastn (sequence alignment for Vδ2 amplicon sequence)

```
Query    6    TATACCGAGAAAGGACATCTATGGCCCTGTGTTTCAAAGACAATTTCCAAGGTGACATTG    65
              ||||||||||||||||||||||||||||||||||||||||||||||||||||||||||||
Sbjct  146    TATACCGAGAAAGGACATCTATGGCCCTGTGTTTCAAAGACAATTTCCAAGGTGACATTG    205

Query   66    ATATTGCAAAGAACCTGGCTGTACTTAAGATACTTGCACCATCAGAGAGAGATGAAGGGT    125
              ||||||||||||||||||||||||||||||||||||||||||||||||||||||||||||
Sbjct  206    ATATTGCAAAGAACCTGGCTGTACTTAAGATACTTGCACCATCAGAGAGAGATGAAGGGT    265

Query  126    CTTACTACTGTGCCTGTGACACCGTAA-A-TGGGGGATACGCG-GTCACCGATAAACTCA    182
              |||||||||||||||||||||||||||| | ||||||||||||  | |||||||||||||
Sbjct  266    CTTACTACTGTGCCTGTGACACCGTAGTACTGGGGGATACGCTCGACACCGATAAACTCA    325

Query  183    TCTTTGGAAAAGGAACCCGTGTGACTGTGGAC-AAG    218   (SEQ ID NO: 10)
              |||||||||||||||||||||||||||||||| |||
Sbjct  326    TCTTTGGAAAAGGAACCCGTGTGACTGTGGAACCAAG    362   (SEQ ID NO: 11)
```

FIG. 5 (cont')

Clone A

Vγ9 amplicon sequence:

ATGCATGCTCGAGCGGCCGCCAGTGTGATGGATATCTGCAGAATTCGCCCTTTGTAATGATAAGCTTTGTTCCGGGACCAAATAC
CTTGATTTTTTTGCCCAACTCCAGCACCTCCCACAAGGCACAGTAGTAGGTAGCTATGTCCTGTTTCTCTACATTGTGAATGGTGA
GAGTGGATGTAGACGTTTCAGGTATCCTATCCACCTCAAATTTGCCTGACGGAATGCCGGATTCCTTTCTGACAGTGCCGTCATAT
GAAATGGACACCAGGAACTGTATGACTTCACCAGGTCTCTCTCGATACCAATATACAGATGTTGCAGAAATTGTTATTCCAGACA
CCACACATTCCAGGCGGGCTGTTTTTGACAGCGTTTTAGTACTGGAAATTTGAGGTTGCTCTAGGTGACCTGCAAGGGCGAATTC
CAGCACACTGGCGGCCGTTACTAGTGGATCCGAGCTCGGTACCAAGCTTGATGCATAGCTTGAGTA (SEQ ID NO: 1)

1a. blastn (sequence alignment for Vγ9 amplicon sequence)

```
Query   53    TGTAATGATAAGCTTTGTTCCGGGACCAAATACCTTGAttttttGCCCAACTCCAGCAC   112
              |||||||||||||||||||||||||||||||||||||||      ||||||||||||||  ||||
Sbjct   363   TGTAATGATAAGCTTTGTTCCGGGACCAAATACCTTGATTTTTTTGCCCAACTCCCGCAC   304

Query   113   CTCCCACAAGGCACAGTAGTAGGTAGCTATGTCCTGTTTCTCTACATTGTGAATGGTGAG   172
              ||||||||||||||||||||||||||||||||||||||||||||||||||||||||||||
Sbjct   303   CTCCCACAAGGCACAGTAGTAGGTAGCTATGTCCTGTTTCTCTACATTGTGAATGGTGAG   244

Query   173   AGTGGATGTAGACGTTTCAGGTATCCTATCCACCTCAAATTTGCCTGACGGAATGCCGGA   232
              ||||||||||||||||||||||||||||||||||||||||||||||||||||||||||||
Sbjct   243   AGTGGATGTAGACGTTTCAGGTATCCTATCCACCTCAAATTTGCCTGACGGAATGCCGGA   184

Query   233   TTCCTTTCTGACAGTGCCGTCATATGAAATGGACACCAGGAACTGTATGACTTCACCAGG   292
              ||||||||||||||||||||||||||||||||||||||||||||||||||||||||||||
Sbjct   183   TTCCTTTCTGACAGTGCCGTCATATGAAATGGACACCAGGAACTGTATGACTTCACCAGG   124

Query   293   TCTCTCTCGATACCAATATACAGATGTTGCAGAAATTGTTATTCCAGACACCACACATTC   352
              ||||||||||||||||||||||||||||||||||||||||||||||||||||||||||||
Sbjct   123   TCTCTCTCGATACCAATATACAGATGTTGCAGAAATTGTTATTCCAGACACCACACATTC   64

Query   353   CAGGCGGGCTGTTTTTGACAGCGTTTTAGTACTGGAAATTTGAGGTTGCTCTAGGTGACC   412
              ||||||||||||||||||||||||||||||||||||||||||||||||||||||||||||
Sbjct   63    CAGGCGGGCTGTTTTTGACAGCGTTTTAGTACTGGAAATTTGAGGTTGCTCTAGGTGACC   4

Query   413   TGC   415 (SEQ ID NO: 2)
              |||
Sbjct   3     TGC   1   (SEQ ID NO: 3)
```

FIG. 6A

Vδ2 amplicon sequence:
AGAAGGGGGGCGGGGCCGCCTATGAATGATTCGCCAGCTTTTGGTGACCTATACAATACTCGGCTATGCATCAGCTTGGTACCG
ATTTCGGATCCACTAGTAACGGCCGCCAGTGTGCTGGAATTCTCCCTTATACCGAGAAAAGGACATCTATGGCCCTGGTTACAAA
GACAATTTCCAAGGTGACATTGATATTGCCCAGAACCTGGCTGTACTTAAGATACTTGCACCATCAGAGAGAGATGAAGGGTCTT
ACTACTGTGCCTGTGACACCGTGGGGGAACAAACCGATAAACTCATCTTTGGAAAAGGAACCCGTTGTGACTGTGGAACAAGGG
CGAATTCTGCAGATATCCATCACACTGGCGGCCGCTCGAGCATGCATCTAGAGGGCCCAAT (SEQ ID NO: 4)

2a. blastn (sequence alignment for Vδ2 amplicon sequence)

```
Query  132  TATACCGAGAAAAGGACATCTATGGCCCTGGTTACAAAGACAATTTCCAAGGTGACATTG  191
            ||||||||||||||||||||||||||||||| ||||||||||||||||||||||||||||
Sbjct  161  TATACCGAGAAAAGGACATCTATGGCCCTGGTTTCAAAGACAATTTCCAAGGTGACATTG  220

Query  192  ATATTGCCCAGAACCTGGCTGTACTTAAGATACTTGCACCATCAGAGAGAGATGAAGGGT  251
            ||||||| ||||||||||||||||||||||||||||||||||||||||||||||||||||
Sbjct  221  ATATTGCAAAGAACCTGGCTGTACTTAAGATACTTGCACCATCAGAGAGAGATGAAGGGT  280

Query  252  CTTACTACTGTGCCTGTGACACCGTGGGGGA-ACA-A-ACCGATAAACTCATCTTTGGAA  308
            |||||||||||||||||||||||||||||||  ||  | ||||||||||||||||||||
Sbjct  281  CTTACTACTGTGCCTGTGACACCGTGGGGGATACCGACACCGATAAACTCATCTTTGGAA  340

Query  309  AAGGAACCCGTTGTGACTGTGGAAC-AAG    336 (SEQ ID NO: 5)
            ||||||||||  |||||||||||||  |||
Sbjct  341  AAGGAACCCG-TGTGACTGTGGAACCAAG   368 (SEQ ID NO: 6)
```

*FIG. 6A (cont')*

Clone C

Vγ9 amplicon sequence:
CCAGCTGGCGAAAGGGGGATGTGCTGCAAGGCGATTAAGTTGGGTAACGCCAGGGTTTTCCCAGTCACGACGTTGTAAAACGA
CGGCCAGTGAATTGTAATACGACTCACTATAGGGCGAATTGGGCCCTCTAGATGCATGCTCGAGCGGCCGCCAGTGTGATGGAT
ATCTGCAGAATTCAGGCCTGAATTCGCCCTTTGTAATGATAAGCTTTGTTCCGGGACCAAATACCTTGATTTTTTTGCCCAACTCTT
GTGTCTCCCACAAGGCACAGTASTASGTAGCTATGTCCTGTTTCTCTACATTGTGAATGGTGAGAGTGGATGTAGACGTTTCAGG
TATCCTATCCACCTCAAATTTGCCTGACGGAATGCCGGATTCCTTTCTGACAGTGCCGTCATATGAAATGGACACCAGGAACTGTA
TGACTTCACCAGGTCTCTCGATACCAATATACAGATGTTGCAGAAATTGTTATTCCAGACACCACACATTCCAGGCGGGCTGTT
TTTGACAGCGTTTTAGTACTGGAAATTTGAGGTTGCTCTAGGTGACCTGCAAGGGCGAATTCCAGCACACTGGCGGCCGTTACTA
GTGGATCCGAGCTCGGTACCAAGCTTGATGCATAGCTTGAGTATTCTATAGTGTCACCTAAATAGCTTGGCGTAATCATGGTCAT
AGCTGTTTCCTGTGTGAAATTGTTATCCGCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCC (SEQ ID NO: 12)

1a. blastn (sequence alignment for Vγ9 amplicon sequence)

```
Query  199  TGTAATGATAAGCTTTGTTCCGGGACCAAATACCTTGAtttttttGCCCAACTCTTGTGT  258
            ||||||||||||||||||||||||||||||||||||||     ||||||||||||| |
Sbjct  363  TGTAATGATAAGCTTTGTTCCGGGACCAAATACCTTGATTTTTTTGCCCAACTCTTGGTT  304

Query  259  CTCCCACAAGGCACAGTASTASGTAGCTATGTCCTGTTTCTCTACATTGTGAATGGTGAG  318
            |||||||||||||||||||  || |||||||||||||||||||||||||||||||||||
Sbjct  303  CTCCCACAAGGCACAGTAGTAGGTAGCTATGTCCTGTTTCTCTACATTGTGAATGGTGAG  244

Query  319  AGTGGATGTAGACGTTTCAGGTATCCTATCCACCTCAAATTTGCCTGACGGAATGCCGGA  378
            ||||||||||||||||||||||||||||||||||||||||||||||||||||||||||||
Sbjct  243  AGTGGATGTAGACGTTTCAGGTATCCTATCCACCTCAAATTTGCCTGACGGAATGCCGGA  184

Query  379  TTCCTTTCTGACAGTGCCGTCATATGAAATGGACACCAGGAACTGTATGACTTCACCAGG  438
            ||||||||||||||||||||||||||||||||||||||||||||||||||||||||||||
Sbjct  183  TTCCTTTCTGACAGTGCCGTCATATGAAATGGACACCAGGAACTGTATGACTTCACCAGG  124

Query  439  TCTCTCGATACCAATATACAGATGTTGCAGAAATTGTTATTCCAGACACCACACATTC   496
            ||||||||||||||||||||||||||||||||||||||||||||||||||||||||||
Sbjct  123  TCTCTCGATACCAATATACAGATGTTGCAGAAATTGTTATTCCAGACACCACACATTC    64

Query  499  CAGGCGGGCTGTTTTTGACAGCGTTTTAGTACTGGAAATTTGAGGTTGCTCTAGGTGACC  558
            ||||||||||||||||||||||||||||||||||||||||||||||||||||||||||||
Sbjct   63  CAGGCGGGCTGTTTTTGACAGCGTTTTAGTACTGGAAATTTGAGGTTGCTCTAGGTGACC   4

Query  559  TGC  561 (SEQ ID NO: 13)
            |||
Sbjct    3  TGC  1 (SEQ ID NO: 14)
```

FIG. 6B

Clone D

Vγ9 amplicon sequence:

ATAGGGCGAATTGGGCCCTCTAGATGCATGCTCGAGCGGCCGCCAGTGTGATGGATATCTGCAGAATTCGCCCTTGCAGGTCAC
CTAGAGCAACCTCAAATTTCCAGTACTAAAACGCTGTCAAAAACAGCCCGCCTGGAATGTGTGGTGTCTGGAATAACAATTTCTG
CAACATCTGTATATTGGTATCGAGAGAGACCTGGTGAAGTCATACAGTTCCTGGTGTCCATTTCATATGACGGCACTGTCAGAAA
GGAATCCGGCATTCCGTCAGGCAAATTTGAGGTGGATAGGATACCTGAAACGTCTACATCCACTCTCACCATTCACAATGTAGAG
AAACAGGACATAGCTACCTACTACTGTGCCTTGTGGGAGTCACAAGAGTTGGGCAAAAAAATCAAGGTATTTGGTCCCGGAACA
AAGCTTATCATTACAAAGGGCGAATTCCAGCACACTGGCGGCCGTTACTAGTGGATCCGAGCTCGGTACCAAGCTTGATGCATA
GCTTGAGTATTCTATAG (SEQ ID NO: 15)

1a. blastn (sequence alignment for Vγ9 amplicon sequence)

```
Query   76    GCAGGTCACCTAGAGCAACCTCAAATTTCCAGTACTAAAACGCTGTCAAAAACAGCCCGC    135
              ||||||||||||||||||||||||||||||||||||||||||||||||||||||||||||
Sbjct   1     GCAGGTCACCTAGAGCAACCTCAAATTTCCAGTACTAAAACGCTGTCAAAAACAGCCCGC    60

Query   136   CTGGAATGTGTGGTGTCTGGAATAACAATTTCTGCAACATCTGTATATTGGTATCGAGAG    195
              ||||||||||||||||||||||||||||||||||||||||||||||||||||||||||||
Sbjct   61    CTGGAATGTGTGGTGTCTGGAATAACAATTTCTGCAACATCTGTATATTGGTATCGAGAG    120

Query   196   AGACCTGGTGAAGTCATACAGTTCCTGGTGTCCATTTCATATGACGGCACTGTCAGAAAG    255
              ||||||||||||||||||||||||||||||||||||||||||||||||||||||||||||
Sbjct   121   AGACCTGGTGAAGTCATACAGTTCCTGGTGTCCATTTCATATGACGGCACTGTCAGAAAG    180

Query   256   GAATCCGGCATTCCGTCAGGCAAATTTGAGGTGGATAGGATACCTGAAACGTCTACATCC    315
              ||||||||||||||||||||||||||||||||||||||||||||||||||||||||||||
Sbjct   181   GAATCCGGCATTCCGTCAGGCAAATTTGAGGTGGATAGGATACCTGAAACGTCTACATCC    240

Query   316   ACTCTCACCATTCACAATGTAGAGAAACAGGACATAGCTACCTACTACTGTGCCTTGTGG    375
              ||||||||||||||||||||||||||||||||||||||||||||||||||||||||||||
Sbjct   241   ACTCTCACCATTCACAATGTAGAGAAACAGGACATAGCTACCTACTACTGTGCCTTGTGG    300

Query   376   GAG-TCACAAGAGTTGGGCaaaaaaTCAAGGTATTTGGTCCCGGAACAAAGCTTATCAT    434
              ||| || ||||||||||||      |||||||||||||||||||||||||||||||||||
Sbjct   301   GAGATC-CAAGAGTTGGGCAAAAAAATCAAGGTATTTGGTCCCGGAACAAAGCTTATCAT    359

Query   435   TACA    438 (SEQ ID NO: 16)
              ||||
Sbjct   360   TACA    363 (SEQ ID NO: 17)
```

*FIG. 6C*

Vδ2 amplicon sequence:

TTGGGCCCTCTAGATGCATGCTCGAGCGGCCGCCAGTGTGATGGATATCTGCAGAATTCGCCCTTATACCGAGAAAAGGACATCT
ATGGCCCTGGTTTCAAAGACAATTTCCAAGGTGACATTGATATTGCAAAGAACCTGGCTGTACTTAAGATACTTGCACCATCAGA
GAGAGATGAAGGGTCTTACTACTGTGCCTGTGACACCTTACTTCCTGGGGGACCGTACACCGATAAACTCATCTTTGGAAAAGGA
ACCCGTGTGACTGTGGAACAAGGGCGAATTCCAGCACACTGGCGGCCGTTACTAGTGGATCCGAGCTCGGTACCAAGCTTGATG
CATAGCTTGAGTATTCTATAG (SEQ ID NO: 18)

2a. blastn (sequence alignment for Vδ2 amplicon sequence)

```
Query   65    TATACCGAGAAAAGGACATCTATGGCCCTGGTTTCAAAGACAATTTCCAAGGTGACATTG   124
              ||||||||||||||||||||||||||||||||||||||||||||||||||||||||||||
Sbjct   237   TATACCGAGAAAAGGACATCTATGGCCCTGGTTTCAAAGACAATTTCCAAGGTGACATTG   296

Query   125   ATATTGCAAAGAACCTGGCTGTACTTAAGATACTTGCACCATCAGAGAGAGATGAAGGGT   184
              ||||||||||||||||||||||||||||||||||||||||||||||||||||||||||||
Sbjct   297   ATATTGCAAAGAACCTGGCTGTACTTAAGATACTTGCACCATCAGAGAGAGATGAAGGGT   356

Query   185   CTTACTACTGTGCCTGTGACACCTTACTTCCTGGGGAC--C-GTACACCGATAAACTCA   241
              |||||||||||||||||||||||||||  | | ||||||||  | |||||||||||||||
Sbjct   357   CTTACTACTGTGCCTGTGACACCTTGCGTACTGGGGACGACTGTACACCGATAAACTCA   416

Query   242   TCTTTGGAAAAGGAACCCGTGTGACTGTGGAAC-AAG    277 (SEQ ID NO: 19)
              |||||||||||||||||||||||||||||||||  |||
Sbjct   417   TCTTTGGAAAAGGAACCCGTGTGACTGTGGAACCAAG    453 (SEQ ID NO: 20)
```

*FIG. 6C (cont')*

Clone E

Vγ9 amplicon sequence:

GGCGAATTGGGCCCTCTAGATGCATGCTCGAGCGGCCGCCAGTGTGATGGATATCTGCAGAATTCGCCCTTTGTAATGATAAGCT
TTGTTCCGGGACCAAATACCTTGATTTTTTTGCCCAACTCTTGTAGCTCCCACAAGGCACAGTAGTAGGTAGCTATGTCCTGTTTCT
CTACATTGTGAATGGTGAGAGTGGATGTAGACGTTTCAGGTATCCTATCCACCTCAAATTTGCCWGACGGAATGCCGGATTCCTT
TCTGACAGTGCCGTCATATGAAATGGACACCAGGAACTGTATGACTTCACCAGGTCTCTCTCGATACCAATATACAGATGTTGCA
GAAATTGTTATTCCAGACACCACACATTCCAGGCGGGCTGTTTTTGACAGCGTTTTAGTACTGGAAATTTGAGGTTGCTCTAGGT
GACCTGCAAGGGCGAATTCAGGCCTGAATTCCAGCACACTGGCGGCCGTTACTAGTGGATCCGAGCTCGGTACCAAGCTTGATG
CATAGCTTGAGTATTCTATAGTGTCACCTAAATAGCTTGGCGTAAATCATGGTCATAGCTGTTTCCTGTGTGAAATTGTTATCCGC
TCACAAATTCCACACAACATACGAGCCGGAAGCATAAAGTGTAAAGCCTGGGGTGCCTAATGA (SEQ ID NO: 21)

1a. blastn (sequence alignment for Vγ9 amplicon sequence)

```
Query   72   TGTAATGATAAGCTTTGTTCCGGGACCAAATACCTTGA-----GCCCAACTCTTGTAG   131
             ||||||||||||||||||||||||||||||||||||||     ||||||||||||| |
Sbjct   363  TGTAATGATAAGCTTTGTTCCGGGACCAAATACCTTGATTTTTTGCCCAACTCTTGGAT  304

Query   132  CTCCCACAAGGCACAGTAGTAGGTAGCTATGTCCTGTTTCTCTACATTGTGAATGGTGAG  191
             ||||||||||||||||||||||||||||||||||||||||||||||||||||||||||||
Sbjct   303  CTCCCACAAGGCACAGTAGTAGGTAGCTATGTCCTGTTTCTCTACATTGTGAATGGTGAG  244

Query   192  AGTGGATGTAGACGTTTCAGGTATCCTATCCACCTCAAATTTGCCWGACGGAATGCCGGA  251
             |||||||||||||||||||||||||||||||||||||||||||| |||||||||||||||
Sbjct   243  AGTGGATGTAGACGTTTCAGGTATCCTATCCACCTCAAATTTGCCTGACGGAATGCCGGA  184

Query   252  TTCCTTTCTGACAGTGCCGTCATATGAAATGGACACCAGGAACTGTATGACTTCACCAGG  311
             ||||||||||||||||||||||||||||||||||||||||||||||||||||||||||||
Sbjct   183  TTCCTTTCTGACAGTGCCGTCATATGAAATGGACACCAGGAACTGTATGACTTCACCAGG  124

Query   312  TCTCTCTCGATACCAATATACAGATGTTGCAGAAATTGTTATTCCAGACACCACACATTC  371
             ||||||||||||||||||||||||||||||||||||||||||||||||||||||||||||
Sbjct   123  TCTCTCTCGATACCAATATACAGATGTTGCAGAAATTGTTATTCCAGACACCACACATTC  64

Query   372  CAGGCGGGCTGTTTTTGACAGCGTTTTAGTACTGGAAATTTGAGGTTGCTCTAGGTGACC  431
             ||||||||||||||||||||||||||||||||||||||||||||||||||||||||||||
Sbjct   63   CAGGCGGGCTGTTTTTGACAGCGTTTTAGTACTGGAAATTTGAGGTTGCTCTAGGTGACC  4

Query   432  TGC  434 (SEQ ID NO: 22)
             |||
Sbjct   3    TGC  1 (SEQ ID NO: 23)
```

FIG. 6D

Vδ2 amplicon sequence:

TGGGCCCTCTAGATGCATGCTCGAGCGGCCGCCAGTGTGATGGATATCTGCAGAATTCAGGCCTGAATTCGCCCTTGTTCCACAG
TCACACGGGTTCCTTTTCCAAAGATGAGTTTATCGGTGTACTTCTACCCCCAGTAGAGTAGCAGGCACAGTATTAAGACCCTTCAT
CTCTCTCTGATGGTGCAAGTATCTTAAGTACAGCCAGGTTCTTTGCAATATCAATGTCACCTTGGAAATTGTCTTTGAAACCAGGG
CCATAGATGTCCTTTTCTCGG (SEQ ID NO: 24)

2a. blastn (sequence alignment for Vδ2 amplicon sequence)

```
Query   74   CTT-GTTCCACAGTCACACGGGTTCCTTTTCCAAAGATGAGTTTATCGGTGT-ACTTCTA   131
             ||| ||||||||||||||||||||||||||||||||||||||||||||||||  | | ||
Sbjct  356   CTTGGTTCCACAGTCACACGGGTTCCTTTTCCAAAGATGAGTTTATCGGTGTTCCCTTTA   297

Query  132   -CCCCCAGTAGAGTAGCAGGCACAGTATTAAGACCCTTCATCTCTCTCTGATGGTGCAAG   190
              ||||||||  ||  |||||||||||||| |||||||||||||||||||||||||||||
Sbjct  296   TCCCCCAGTA-TGTCACAGGCACAGTAGTAAGACCCTTCATCTCTCTCTGATGGTGCAAG   238

Query  191   TATCTTAAGTACAGCCAGGTTCTTTGCAATATCAATGTCACCTTGGAAATTGTCTTTGAA   250
             ||||||||||||||||||||||||||||||||||||||||||||||||||||||||||||
Sbjct  237   TATCTTAAGTACAGCCAGGTTCTTTGCAATATCAATGTCACCTTGGAAATTGTCTTTGAA   178

Query  251   ACCAGGGCCATAGATGTCCTTTTCTCGG   278 (SEQ ID NO: 25)
             ||||||||||||||||||||||||||||
Sbjct  177   ACCAGGGCCATAGATGTCCTTTTCTCGG   150 (SEQ ID NO: 26)
```

FIG. 6D (cont')

Clone B

Clone D

Clone C

Clone E

MATERIALS AND METHODS FOR THE MANUFACTURE OF PLURIPOTENT STEM CELLS

CROSS-REFERENCE TO RELATED APPLICATIONS

This application claims the benefit of U.S. Ser. No. 63/040,373, filed Jun. 17, 2020; U.S. Ser. No. 63/040,374, filed Jun. 17, 2020; U.S. Ser. No. 63/040,392, filed Jun. 17, 2020; U.S. Ser. No. 63/040,397, filed Jun. 17, 2020; U.S. Ser. No. 63/040,398, filed Jun. 17, 2020, each of which is herein incorporated by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file "14620-526-999 SEQ LISTING" and a creation date of May 30, 2021 and having a size of 21,883 bytes. The sequence listing submitted via EFS-Web is part of the specification and is herein incorporated by reference in its entirety.

1. FIELD

Provided herein are, inter alia, methods of producing induced pluripotent stem cells (iPSCs) and isolated population of produced induced pluripotent stem cells (iPSCs), and uses thereof.

2. BACKGROUND

Pluripotent stem cells such as embryonic stem (ES) cells and induced pluripotent stem cells (iPSCs) possess the proliferative and developmental capacity to differentiate and generate multiple cell types in the body. The therapeutic and scientific potential of these cells is thus uncertain but extraordinary, especially after studies are said to have revealed that gene expression profiles in somatic cells can be changed to epigenetically reprogram them into pluripotent stem cells (see, e.g., Takahashi, K., & Yamanaka, S, *Nat. Rev. Mol. Cell Biol.*, 2016, 17(3):183-93).

Embryonic stem cells can be derived from the inner cell mass of mammalian blastocysts, see, e.g., Human Genes and Genomes: Science, Health, Society (Rosenberg, L. E. & Rosenberg, D. D., 1st ed. 2012). Additionally, somatic cell nuclear transfer (SCNT)-mediated reprogramming has also been utilized to generate pluripotent ES cells, and in some instances, cloned animals (Wilmut, I., et al., *Nature,* 1997, 385:810-813; Wakayama, T., et al., *Nature,* 1998, 394:369-374). Nevertheless, SCNT has suffered from various technical (e.g., epigenetic) barriers since the destruction of embryos and introduction of mammalian genetic information into an unfertilized egg is subject to controversies (Matoba, S. & Zhang, Y., supra; Kastenberg, Z. J. & Odorico, J. S., *Transplant Rev.,* 2008, 22(3):215-22).

Alternative techniques to reprogram somatic cells into pluripotent stem cells remain an interest. Induced Pluripotent Stem Cell (iPSC) technologies emerged as one of such alternatives when Yamanaka et al. reported that transcription factors Oct3/4, Sox2, Klf4 and c-Myc may confer pluripotency upon adult somatic cells and for generating iPSCs (Takahashi, K., & Yamanaka, S, Cell, 2006, 126(4):663-76; Wernig, M., et al., *Nature,* 2007, 448:318-324; Maherali, N., et al., *Cell Stem Cell,* 2007, 1(1):55-70).

3. SUMMARY

Against this backdrop, there is still a need for improved materials and methods for reprograming somatic cells into pluripotent state(s). In one aspect, provided herein are methods of producing induced pluripotent stem cells (iPSCs) comprising: (a) contacting an isolated population of cells with an activation culture; wherein the activation culture comprises IL-15 and zoledronic acid; (b) culturing the isolated population of cells in the activation culture to enrich and/or activate γδ T cells in the isolated population of cells; (c) transducing the γδ T cells with a viral vector encoding one or more reprogramming factors; and (d) culturing the transduced γδ T cells under conditions suitable for reprogramming mammalian somatic cells to a pluripotent state.

In certain embodiments, the activation culture further comprises IL-2.

In certain embodiments, the viral vector is a Sendai virus (SeV) vector.

In certain embodiments, the method further comprises obtaining the isolated population of cells from a subject.

In certain embodiments, the isolated population of cells are peripheral blood mononuclear cells (PBMCs). In certain embodiments, the isolated population of cells are terminally differentiated cells. In certain embodiments, the isolated population of cells are mammal cells. In certain embodiments, the isolated population of cells are human cells.

In certain embodiments, the isolated population of cells are cultured in the activation culture for 1-20 days. In certain embodiments, the isolated population of cells are cultured in the activation culture for 1-17 days. In certain embodiments, the isolated population of cells are cultured in the activation culture for 1-15 days. In certain embodiments, the isolated population of cells are cultured in the activation culture for 1-13 days. In certain embodiments, the isolated population of cells are cultured in the activation culture for 1-11 days. In certain embodiments, the isolated population of cells are cultured in the activation culture for 1-9 days. In certain embodiments, the isolated population of cells are cultured in the activation culture for 1-7 days. In certain embodiments, the isolated population of cells are cultured in the activation culture for 1-5 days. In certain embodiments, the isolated population of cells are cultured in the activation culture for 1-3 days. In certain embodiments, the isolated population of cells are cultured in the activation culture for 12-72 hours. In certain embodiments, the isolated population of cells are cultured in the activation culture for 12-60 hours. In certain embodiments, the isolated population of cells are cultured in the activation culture for 12-48 hours. In certain embodiments, the isolated population of cells are cultured in the activation culture for 12-36 hours. In certain embodiments, the isolated population of cells are cultured in the activation culture for 12-24 hours. In certain embodiments, the isolated population of cells are cultured in the activation culture for 8-16 hours. In certain embodiments, the isolated population of cells are cultured in the activation culture for 4-8 hours. In certain embodiments, the isolated population of cells are cultured in the activation culture for 2-4 hours.

In certain embodiments, the isolated population of cells are cultured in the activation culture for at most 13 days, at most 10 days, at most 9 days, at most 8 days, at most 7 days, at most 6 days, at most 5 days, at most 4 days, at most 3 days, at most 2 days, or at most 1 day.

In certain embodiments, the isolated population of cells are cultured in the activation culture for at most 3 days. In certain embodiments, the isolated population of cells are cultured in the activation culture for about 3 days. In certain embodiments, the isolated population of cells are cultured in the activation culture for 50 hours to 80 hours. In certain embodiments, the isolated population of cells are cultured in the activation culture for 55 hours to 75 hours. In certain embodiments, the isolated population of cells are cultured in the activation culture for 60 hours to 75 hours. In certain embodiments, the isolated population of cells are cultured in the activation culture for 70 hours to 75 hours.

In certain embodiments, after being cultured in the activation culture the isolated population of cells comprise 5%-100% γδ T cells. In certain embodiments, after being cultured in the activation culture the isolated population of cells comprise 5%-95% γδ T cells. In certain embodiments, after being cultured in the activation culture the isolated population of cells comprise 5%-90% γδ T cells. In certain embodiments, after being cultured in the activation culture the isolated population of cells comprise 5%-85% γδ T cells. In certain embodiments, after being cultured in the activation culture the isolated population of cells comprise 5%-80% γδ T cells. In certain embodiments, after being cultured in the activation culture the isolated population of cells comprise 5%-75% γδ T cells. In certain embodiments, after being cultured in the activation culture the isolated population of cells comprise 5%-70% γδ T cells. In certain embodiments, after being cultured in the activation culture the isolated population of cells comprise 5%-65% γδ T cells. In certain embodiments, after being cultured in the activation culture the isolated population of cells comprise 5%-60% γδ T cells. In certain embodiments, after being cultured in the activation culture the isolated population of cells comprise 5%-55% γδ T cells. In certain embodiments, after being cultured in the activation culture the isolated population of cells comprise 5%-50% γδ T cells. In certain embodiments, after being cultured in the activation culture the isolated population of cells comprise 5%-45% γδ T cells. In certain embodiments, after being cultured in the activation culture the isolated population of cells comprise 5%-40% γδ T cells. In certain embodiments, after being cultured in the activation culture the isolated population of cells comprise 5%-35% γδ T cells. In certain embodiments, after being cultured in the activation culture the isolated population of cells comprise 15%-35% γδ T cells. In certain embodiments, after being cultured in the activation culture the isolated population of cells comprise 25%-35% γδ T cells. In certain embodiments, after being cultured in the activation culture the isolated population of cells comprise 30%-35% γδ T cells. In certain embodiments, after being cultured in the activation culture the isolated population of cells comprise 5%-30% γδ T cells. In certain embodiments, after being cultured in the activation culture the isolated population of cells comprise 5%-25% γδ T cells. In certain embodiments, after being cultured in the activation culture the isolated population of cells comprise 5%-20% γδ T cells. In certain embodiments, after being cultured in the activation culture the isolated population of cells comprise 5%-15% γδ T cells.

In certain embodiments, after being cultured in the activation culture the isolated population of cells comprise less than 90%, less than 80%, less than 70%, less than 60%, less than 50%, less than 45%, less than 40%, less than 35%, or less than 30% γδ T cells. In certain embodiments, after being cultured in the activation culture the isolated population of cells comprise less than 35% γδ T cells.

In certain embodiments, the method further comprises enriching the γδ T cells in the isolated population of cells.

In certain embodiments, the γδ T cells are enriched by cell-cell clump enrichment. In certain embodiments, at least part of the γδ T cells are activated to Vγ9$^+$ γδ T cells in step (b).

In certain embodiments, at least part of the γδ T cells are activated to Vγ9δ2$^+$ γδ T cells in step (b).

In certain embodiments, the one or more reprogramming factors are selected from a group consisting of OCT3/4, SOX2, KLF4, LIN28, and c-Myc.

In certain embodiments, in step (d) the transduced γδ T cells are cultured in the presence of one or more feeder layers. In certain embodiments, in step (d) the transduced γδ T cells are cultured in the presence of a mono layer of feeder layer. In certain embodiments, the feeder layer comprises mouse embryonic fibroblasts (MEFs).

In certain embodiments, the method further comprises isolating and/or purifying the produced iPSCs. In certain embodiments, the method further comprises administering the isolated iPSCs to a subject.

In certain embodiments, the method further comprises differentiating the iPSCs ex vivo to cells of a desired cell type.

In certain embodiments, the method further comprises administering the differentiated cell to a subject. In certain embodiments, the subject is a mammal. In certain embodiments, the subject is a human. In certain embodiments, the subject has a hyperproliferative disorder or a cancer of the hematopoietic system.

In certain embodiments, the produced iPSCs are negative for a Sendai virus (SeV) vector. In certain embodiments, the produced iPSCs are derived from γδ T cells. In certain embodiments, the produced iPSCs have rearrangement genes of TRG and TRD gene loci. In certain embodiments, the produced iPSCs are not derived from αβ T cells.

In certain embodiments, the produced iPSCs do not produce polymerase chain reaction (PCR) products from TCRA and TCRB gene loci. In some embodiments, the produced iPSCs have Vγ9 and Vδ2 gene arrangements. In certain embodiments, the produced iPSCs are genomically stable with no loss of a chromosome. In certain embodiments, the genomic stability of the produced iPSCs is determined by Karyotyping analysis. In certain embodiments, the produced iPSCs can grow in feeder free medium after adoption.

In another aspect, provided herein is an induced pluripotent stem cell (iPSC) produced according to the method provided herein.

In another aspect, provided herein is a pharmaceutical composition comprising the iPSC provided herein and a pharmaceutically acceptable excipient.

In another aspect, provided herein is a differentiated cell produced according to the method provided herein.

In another aspect, provided herein is a pharmaceutical composition comprising the differentiated cell provided herein and a pharmaceutically acceptable excipient.

In yet another aspect, provided herein is method of treating a subject in need thereof comprising: (i) obtaining a population of cells comprising peripheral blood mononuclear cells (PBMCs) from a subject; (ii) reprogramming γδ T cells in the population of cells to produce iPSCs according to the method of producing iPSCs provided herein; and (iii) administering the produced iPSCs, or a pharmaceutical composition comprising the produced iPSCs to the subject, optionally after differentiating the iPSCs into one or more desired types of cells. In certain embodiments, the subject is a human. In certain embodiments, the subject has a hyperproliferative disorder or a cancer of the hematopoietic system.

In yet another aspect, provided herein is an isolated population of induced pluripotent stem cells (iPSCs), wherein the isolated population of iPSCs comprise pluripotent cells, wherein the pluripotent cells express one or more reprogramming factors, and/or wherein the pluripotent cells comprise a nucleotide sequence encoding rearrangement of TRG and TRD genes.

In yet another aspect, provided herein is a method of producing induced pluripotent stem cells (iPSCs) comprising: (a) a step for performing a function of enriching and/or activating γδ T cells in the isolated population of cells; and (b) a step for performing a function of reprogramming the γδ T cells to a pluripotent state. In another aspect, provided herein is an induced pluripotent stem cell (iPSC) produced according to the method provided herein.

In yet another aspect, provided herein is an isolated population of induced pluripotent stem cells (iPSCs) comprising pluripotent cells, wherein the pluripotent cells comprise a means for expressing one or more reprogramming factors, and/or wherein the pluripotent cells comprise a means for encoding rearrangement of TRG and TRD genes.

4. BRIEF DESCRIPTION OF THE FIGURES

FIG. 1 depicts the abundance of TCRVγ9+ γδ T cells among enriched cell-cell clumps on various days of PBMC culture with Zol+IL-2+IL-15. Numbers in representative FACS plots show the frequency of TCR γδ and αβ T cells among whole PBMCs (top row) and TCRVγ9+ cells among γδ T cells (bottom row) on day 3 (left column), day 8 (middle column) and day 13 (right column) of PBMCs stimulated with Zol+IL-2+IL-15. Arrows represent parent and progeny gates.

Figure 2B:
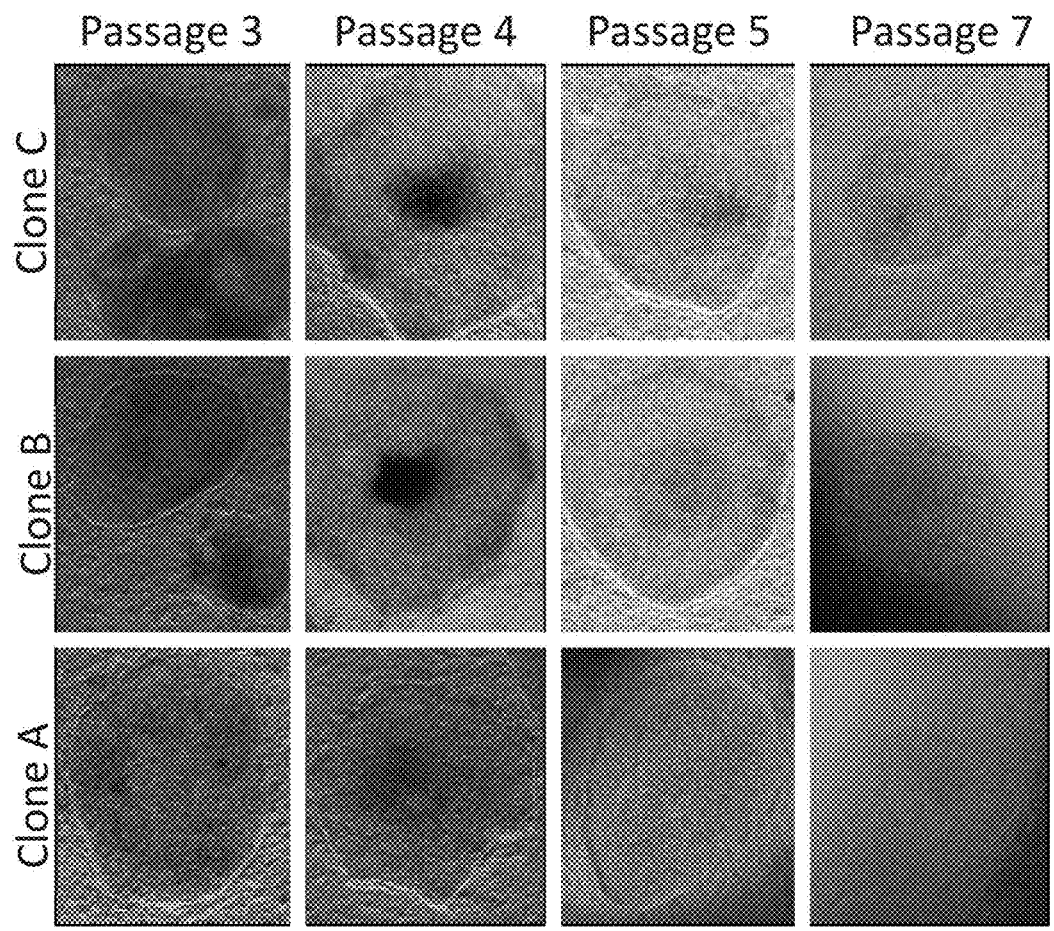
Figure 2A:
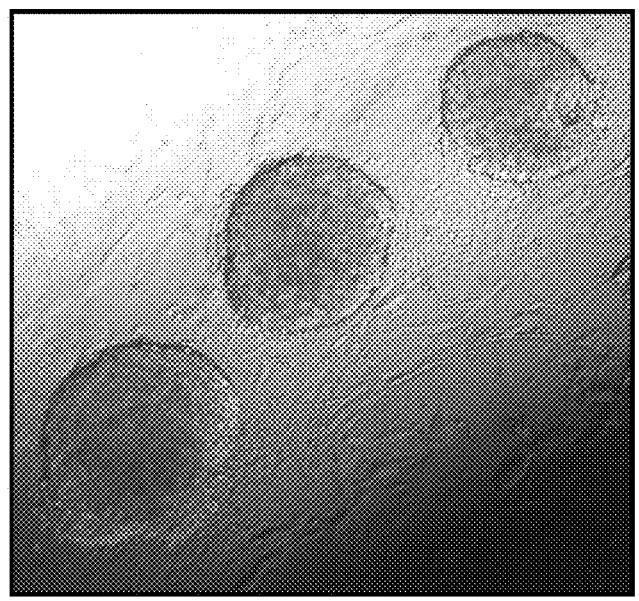

FIGS. 2A-2B depict the microscopic observation of iPSC colonies derived from PBMCs culture stimulated with Zol+IL-2+IL-15 for 3 days. FIG. 2A depicts a representative microscopic image showing iPSCs on MEF feeder layers as round colonies with tight and smooth borders and compact cells insider borders. Elongated cells in the background are Mitomycin-C treated MEF feeder layers. FIG. 2B depicts representative microscopic images showing iPSCs colonies from three individual clones at various passages, i.e., passages 3, 4, 5, and 7. iPSC colonies were on irradiated MEF feeder layers.

FIG. 3 depicts the assessment of gene rearrangement at the TRG locus using IdentiClone™ TCRG gene rearrangement assay. Genomic DNA was isolated from all five colonies. Genomic PCR was performed using primers from IdentiClone™ TCRG gene rearrangement assay kit, pursuant to the manufacturer's protocol. Representative peaks depict the size (in base pairs) of the amplicon from genomic PCR from Clones A, B, C, D and E.

Figure 4:
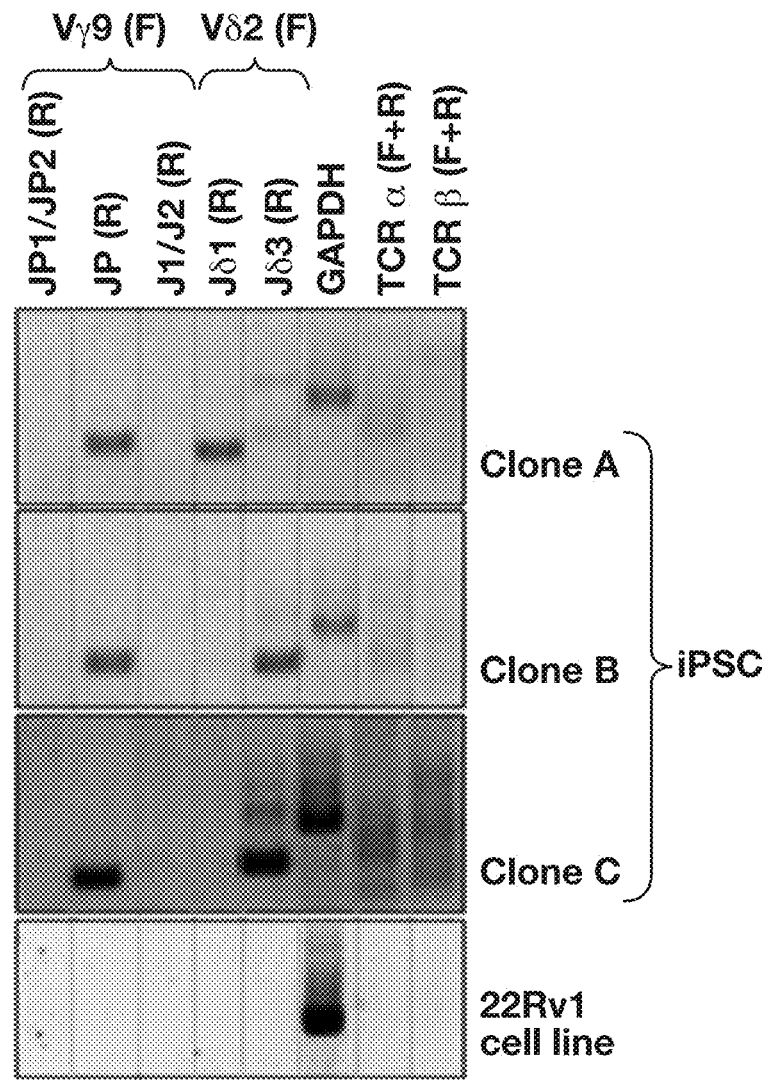

FIG. 4 depicts the assessment of TRG and TRD loci gene rearrangement among iPSC colonies. Representative agarose gel images show the amplification of genomic DNAs from Clones A, B, and C mediated by either Vγ9 or Vδ2 forward primers in combination to various joining region primers. As a negative control, 22 Rv1 cell line genomic DNA was used.

FIG. 5 depicts representative sequence alignment showing the similarity between the sequence obtained from amplicons (from clone B) and human TCR Vγ9 and Vδ2 sequences.

FIGS. 6A-6D depict the assessment of sequence homology between genomic DNA amplified amplicon and TRGV9 and TRDV2 for five iPSC clones. Genomic DNA was isolated from all five iPSC clones and a genomic PCR was performed with primers against TCRVγ9(FP), JP1/JP2, JP or J1/J2 (RV) and TCRVδ2(FP), Jδ1 (RP) or Jδ3 (RP). Amplified products were gel eluted, top cloned and sequenced. Sequence was subjected to BLAST against the whole human genome. FIG. 6A: Clone A; FIG. 6B: Clone C: FIG. 6C: Clone D; FIG. 6D: Clone E). Representative sequence alignment shows the sequence homology between amplicons and TRGV9 and TRDV2 gene sequences.

Figure 7A:
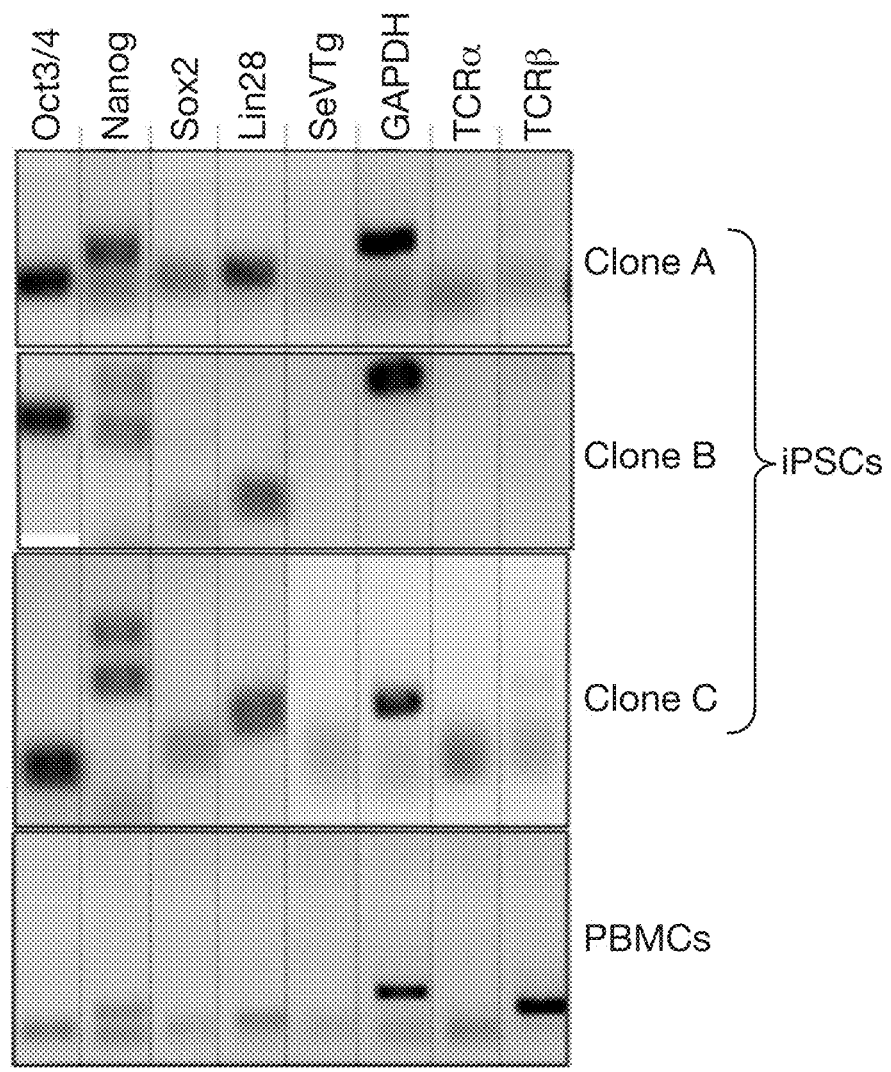
Figure 7B:
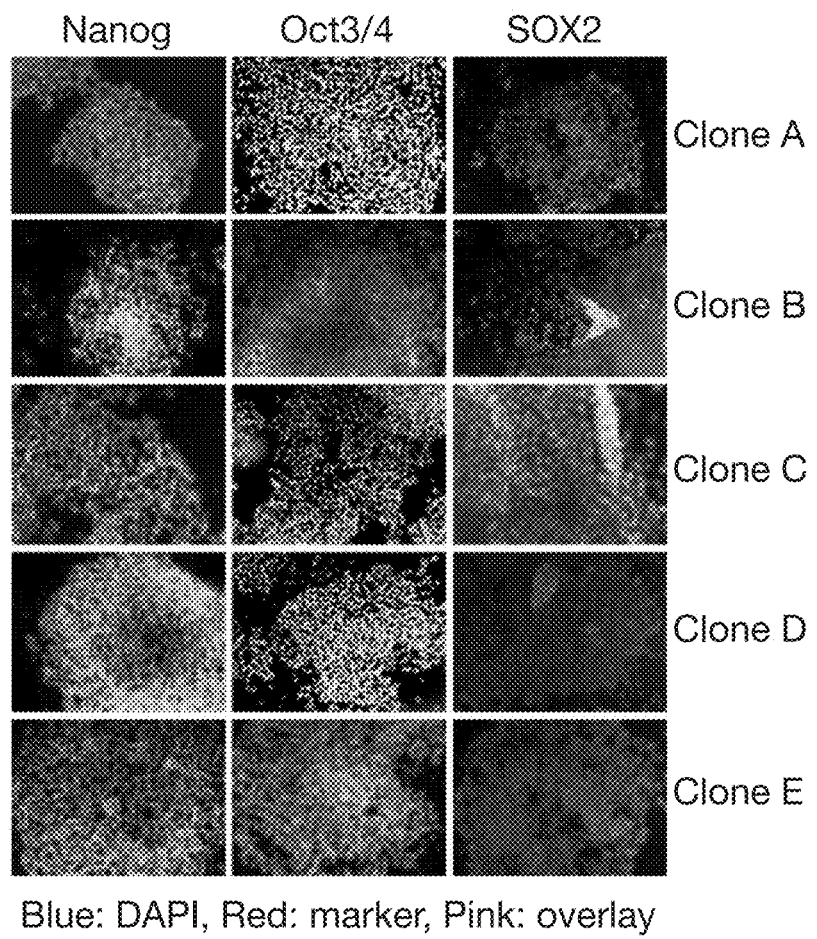
Figure 7C:
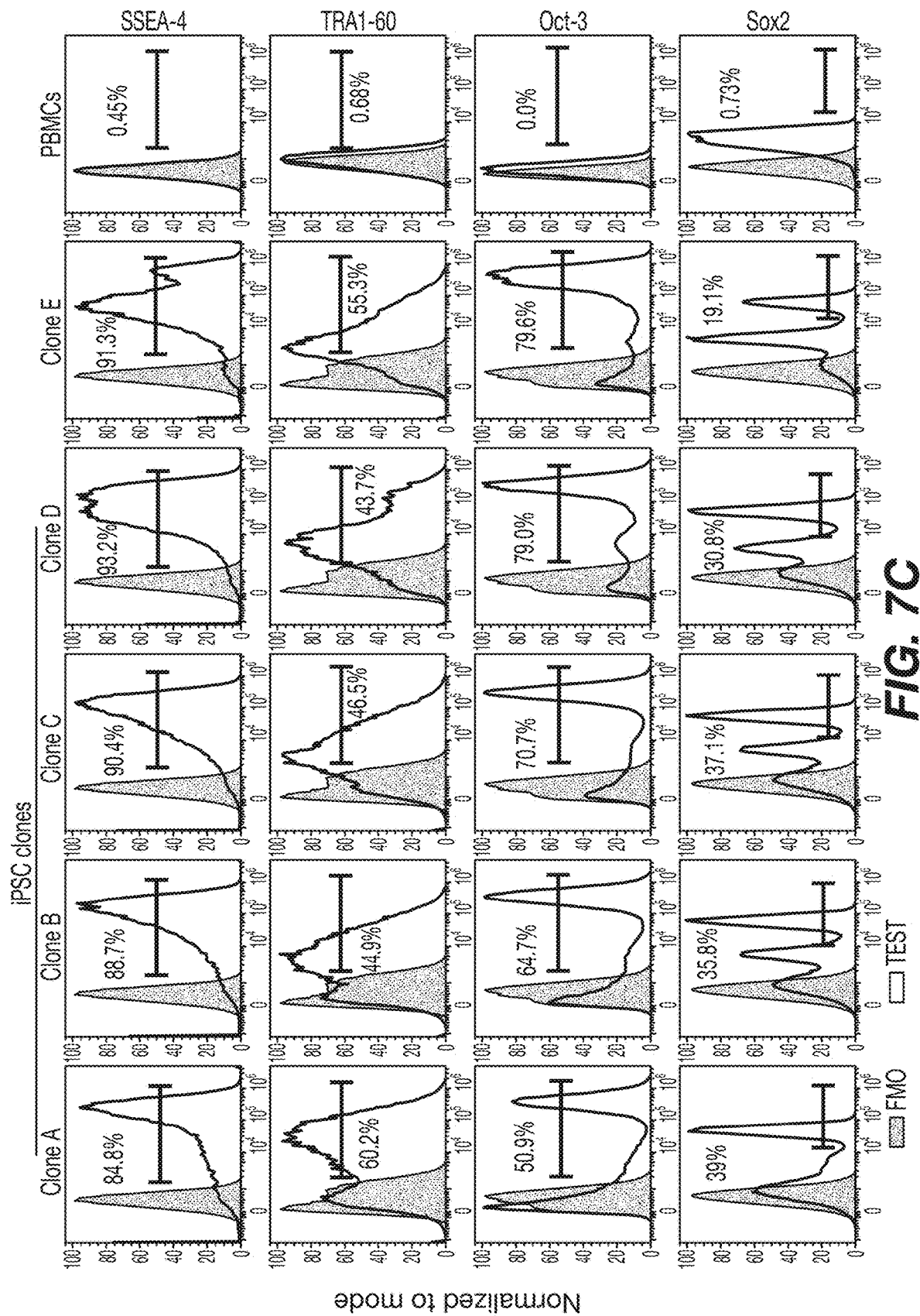

FIGS. 7A-7C depict the characterization of γδ T-cell derived iPSCs. FIG. 7A depicts representative agarose gel image showing the RT-PCR amplicons for Oct3/4, Nanog, Sox2, Lin28, Sendai Virus (SeV), GAPDH, TCR alpha and beta from A, B and C iPSC clones. FIG. 7B shows overlay immunohistochemistry (IHC) images visualizing the cells positive for DAPI (blue only), marker (Nanog/Oct 3/4/Sox2: red only) or DAPI+marker (pink) among iPSC clones. FIG. 7C depicts representative histograms showing the frequency of cells positive for SSEA-4 and TRA 1-60 surface expression and Oct-3 and Sox2 intracellular expression among iPSC Clones A, B, C, D and E.

Figure 8A:
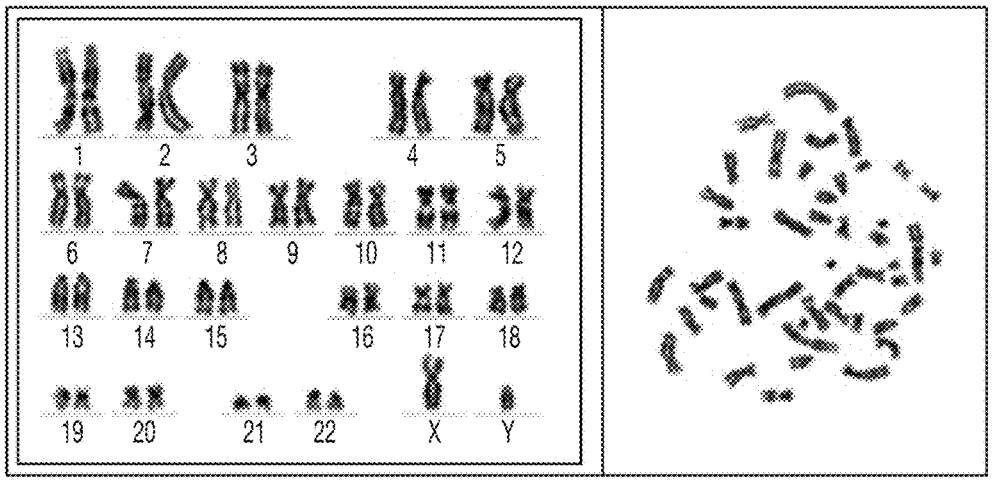
Figure 8B:
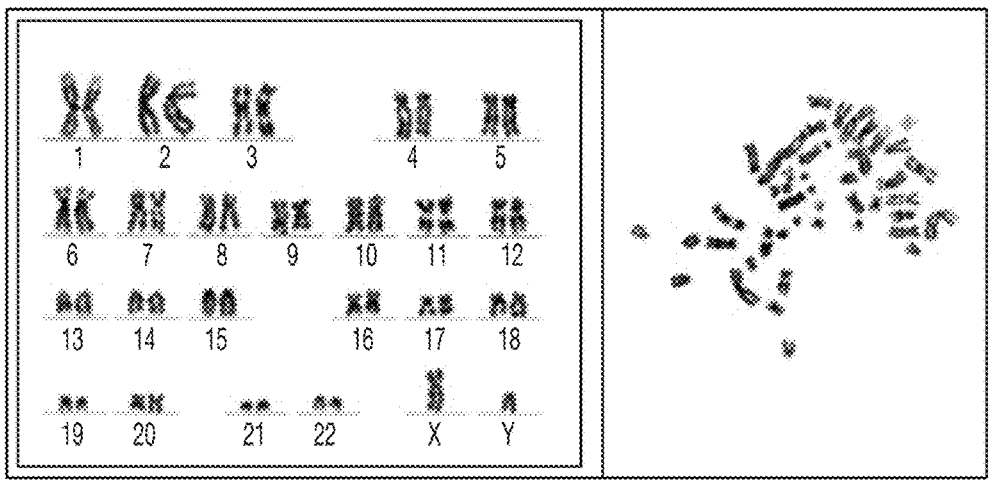
Figure 8C:
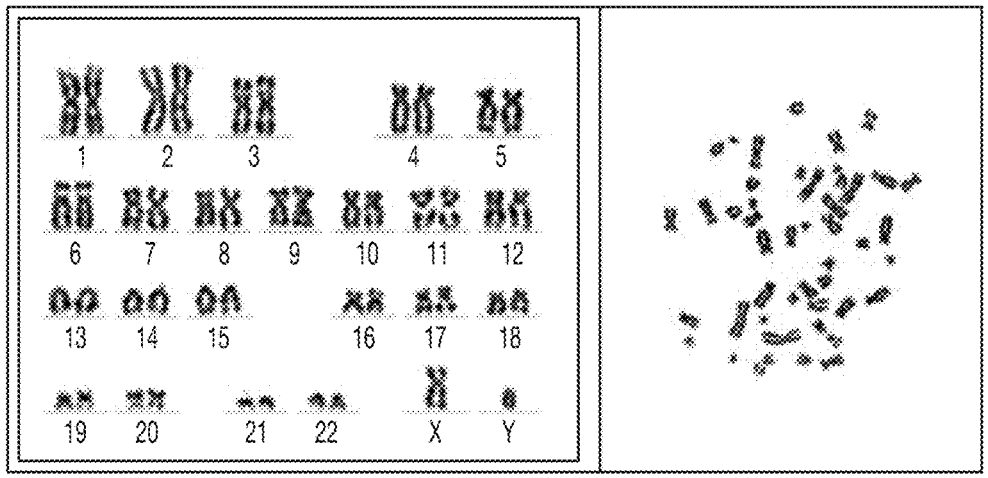
Figure 8D:
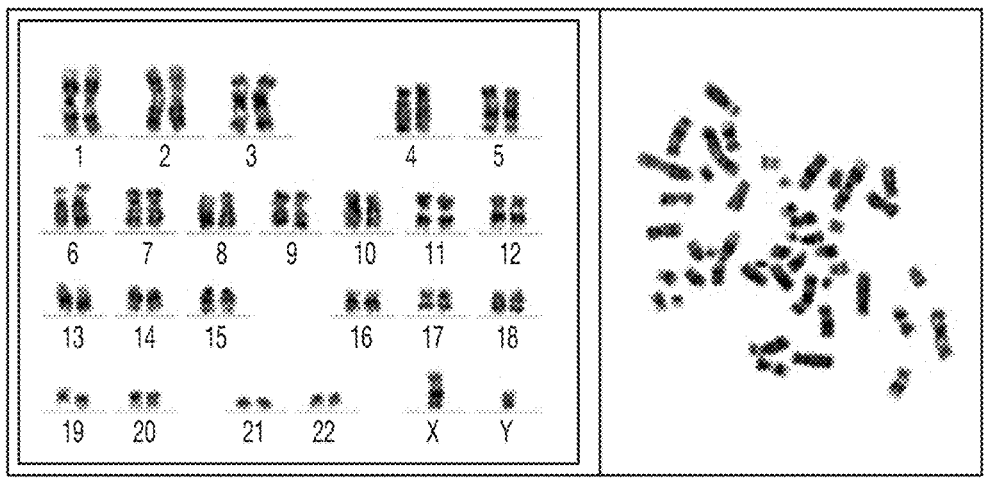

FIGS. 8A-8D depicts the assessment of genomic stability of iPSC Clones B, C, D and E via karyotyping analysis. FIG. 8A: Clone B; FIG. 8B: Clone D; FIG. 8C: Clone C; FIG. 8D: Clone E.

Figure 9:
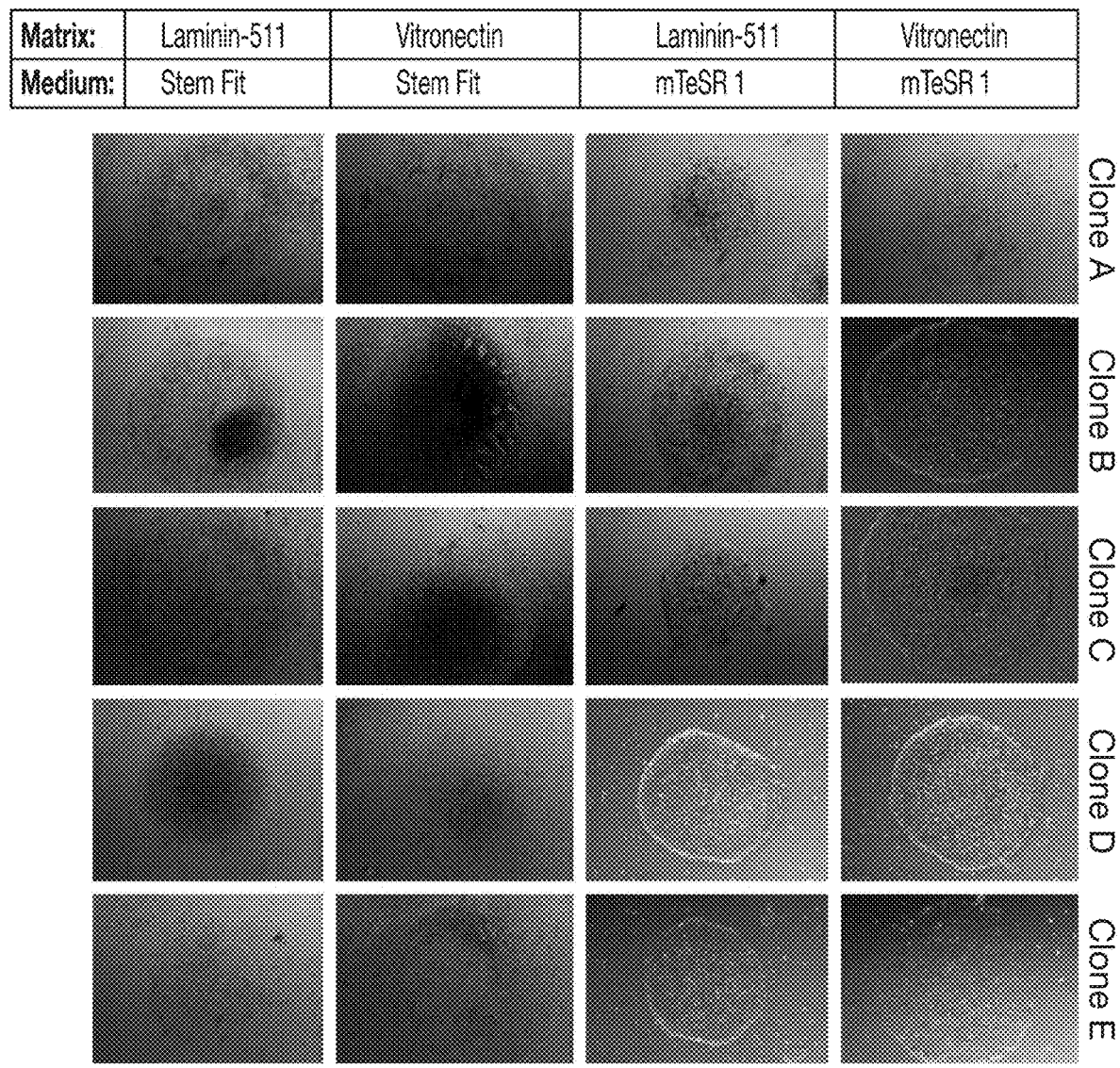

FIG. 9 shows representative bright field microscopic images depicting feed-based iPSC colonies from all five clones (Clones A-E) that were adopted to the feeder-free condition in the presence of different matrix and medium combinations.

5. DETAILED DESCRIPTION

The present disclosure provides in part improved methods for producing iPSCs from T cells, particularly from γδ T cells.

γδ T cells are a subset of T lymphocytes that express TCRs distinctive from those expressed by αβ T cells, a major subset of T lymphocytes in human peripheral blood (Kalyan, S. & Kabelitz, D., Cell Mol. Immunol., 2013, 10(1):21-29). Vγ9Vδ2 T cells are a major subset of γδ T cells, and exhibit significant effector functions against tumor cells (Tyler, C. J., et al., Cellular Immunology, 2015, 296(1):10-21; Silva-Santos. B., Nat Rev Immunol., 2015, 15:683-91). Moreover, unlike αβ T cells, antigen-recognition and anti-tumor efficacy of Vγ9Vδ2 T cells is major histocompatibility complex (MHC)-unrestricted (Kalyan, S. & Kabelitz, D., supra). For these reasons, Vγ9Vδ2 T cells are considered an attractive option for cancer immune therapy and have been explored and exploited clinically (Kakimi, K., et al., Transl Lung Cancer Res., 2014, 3(1):23-33).

5.1. Definitions

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. The range of quantity, level, value, number, frequency, percentage, dimension, size, amount, weight or length can be ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

A "cell culture medium" (also referred to herein as a "culture medium" or "culture" or "medium") is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Some non-limiting examples are provided herein.

As used herein, "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

As used herein, the term "differentiate," "differentiation," or the like refers to the process by which an unspecialized (or uncommitted) or less specialized cell acquires the features of a specialized cell such as, for example, a blood cell or a muscle cell. A differentiated or differentiation-induced cell is one that has taken on a more specialized (or committed) position within the lineage of a cell. A cell is committed when it has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" is intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously As used herein, the term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

As used herein, the term "induced pluripotent stem cells" or, "iPSCs," refers to stem cells produced from differentiated adult cells that have been induced or changed (i.e. reprogrammed) into cells capable of differentiating into tissues of all three germ or dermal layers: mesoderm, endoderm, and ectoderm.

As used herein, the term "isolated" or the like when used in reference to a cell is intended to mean a cell that is substantially free of at least one component as the referenced cell is found in nature. The term includes a cell that is removed from some or all components as it is found in its natural environment. The term also includes a cell that is removed from at least one, some or all components as the cell is found in non-naturally occurring environments. Therefore, an isolated cell is partly or completely separated from other substances as it is found in nature or as it is grown, stored or subsisted in non-naturally occurring environments. Specific examples of isolated cells include partially pure cells, substantially pure cells and cells cultured in a medium that is non-naturally occurring.

As used herein, the term "purify" or the like refers to increase purity. For example, the purity can be increased to at least 50%, 60%, 70%, 80%, 90%, 95%, 99%, or 100%.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "population" when used with reference to T lymphocytes refers to a group of cells including two or more T lymphocytes. The isolated population of T lymphocytes can have only one type of T lymphocyte, or two or more types of T lymphocyte. The isolated population of T lymphocytes can be a homogeneous population of one type of T lymphocyte or a heterogeneous population of two or more types of T lymphocyte. The isolated population of T lymphocytes can also be a heterogeneous population having T lymphocytes and at least a cell other than a T lymphocyte, e.g., a B cell, a macrophage, a neutrophil, an erythrocyte, a hepatocyte, an endothelial cell, an epithelial cells, a muscle cell, a brain cell, etc. The heterogeneous population can have from 0.01% to about 100% T lymphocyte. Accordingly, an isolated population of T lymphocytes can have at least 50%, 60%, 70%, 80%, 90%, 95%, 98%, or 99% T lymphocytes. The isolated population of T lymphocytes can include only one type of T lymphocytes, or a mixture of more than one type of T lymphocytes. The isolated population of T lymphocytes can include one or more, or all of, the different types of T lymphocytes, including but not limited to those disclosed herein. An isolated population of T lymphocytes can include all known types of T lymphocytes. In an isolated population of T lymphocytes that includes more than one type of T lymphocytes, the ratio of each type of T lymphocyte can range from 0.01% to 99.99%. The isolated population also can be a clonal population of T lymphocytes, in which all the T lymphocytes of the population are clones of a single T lymphocyte.

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

As used herein, "reprogramming", refers to a process that alters or reverses the differentiation state of a somatic cell. The cell can be either partially or terminally differentiated prior to reprogramming. Reprogramming encompasses complete reversion of the differentiation state of a somatic cell (e.g., a T cell) to a pluripotent state. Reprogramming also encompasses partial reversion of the differentiation state of a somatic cell to a state that renders the cell more susceptible to complete reprogramming to a pluripotent state when subjected to additional manipulations such as those described herein. Such contacting may result in expression of particular genes by the cells, which expression contributes to reprogramming. In certain embodiments of the invention, reprogramming of a somatic cell causes the somatic cell to be a pluripotent and ES-like state. The resulting cells are referred to herein as reprogrammed pluripotent somatic cells or induced pluripotent stem cells (iPSCs). In some embodiments, reprogramming also encompasses partial reversion of the differentiation state of a somatic cell to a multipotent state.

Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent. In some embodiments, the methods described herein contribute to establishing the pluripotent state by reprogramming. In some embodiments, the methods described herein may be practiced on cells that fully differentiated and/or particular types of cells (e.g., γδ T cells), rather than on cells that are already multipotent or pluripotent.

As used herein, "reprogramming factor" refers to a gene, RNA, or protein that promotes or contributes to cell reprogramming, e.g., in vitro. Examples of reprogramming factors of interest for reprogramming somatic cells to pluripotency in vitro are Oct3/4, Klf4, c-Myc, Nanog, Sox2, and Lin28, and any gene/protein that can substitute for one or more of these in a method of reprogramming somatic cells, e.g., in vitro.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T lymphocyte can be any T lymphocyte, such as a cultured T lymphocyte, e.g., a primary T lymphocyte, or a T lymphocyte from a cultured T cell line, e.g., Jurkat, SupT1, etc., or a T lymphocyte obtained from a mammal. The T lymphocyte can be CD3+ cells. The T lymphocyte can be any type of T lymphocyte and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. A T lymphocyte can be T regulatory cell, which includes nTregs (natural Tregs), iTregs (inducible Tregs), $CD8^+$ Treg, Tr1 regulatory cells, and Th3 cells. Additional types of helper T cells include cells such as Th3 (Treg), Th17, Th9, or Tfh cells. Additional types of memory T cells include cells such as central memory T cells ($T_{CM}$ cells), effector memory T cells ($T_{EM}$ cells and $T_{EMRA}$ cells). The T lymphocyte can also refer to a genetically engineered T lymphocyte, such as a T lymphocyte modified to express a T cell receptor (TCR) or a chimeric antigen receptor (CAR). The T lymphocyte can also be differentiated from a stem cell, definitive hemogenic endothelium, a CD34+ cell, a HSC (hematopoietic stem and progenitor cell), a hematopoietic multipotent progenitor cell, or a T cell progenitor cell.

As used herein, the term "γδ T cells" refers to T cells having T cell receptor comprising a γ-chain and a δ-chain on their surfaces.

As used herein, the term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

In some embodiments, the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an antimitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell type, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder and stromal cells and is also not pre-conditioned by the cultivation of feeder cells.

The term "pluripotency associated gene" refers to a gene whose expression under normal conditions (e.g., in the absence of genetic engineering or other manipulation designed to alter gene expression) occurs in and is typically restricted to pluripotent stem cells, and is crucial for their functional identity as such. It will be appreciated that the polypeptide encoded by a gene functionally associated with pluripotency may be present as a maternal factor in the oocyte. The gene may be expressed by at least some cells of the embryo, e.g., throughout at least a portion of the pre-implantation period and/or in germ cell precursors of the adult.

The term "pluripotency factor" is used refer to the expression product of pluripotency associated gene, e.g., a polypeptide encoded by the gene. In some embodiments, the pluripotency factor is one that is normally substantially not expressed in somatic cell types that constitute the body of an adult animal (with the exception of germ cells or precursors thereof). For example, the pluripotency factor may be one whose average level in ES cells is at least 50-fold or 100-fold greater than its average level in those terminally differentiated cell types present in the body of an adult mammal. In some embodiments, the pluripotency factor is one that is essential to maintain the viability or pluripotent state of ES cells in vivo and/or ES cells derived using conventional methods. Thus if the gene encoding the factor is knocked out or inhibited (i.e., its expression is eliminated or substantially reduced), the ES cells are not formed, die or, in some embodiments, differentiate. In some embodiments, inhibiting expression of a gene whose function is associated with pluripotency in an ES cell (resulting in, e.g., a reduction in the average steady state level of RNA transcript and/or protein encoded by the gene by at least 50%, 60%, 70%, 80%, 90%, 95%, or more) results in a cell that is viable but no longer pluripotent. In some embodiments the gene is characterized in that its expression in an ES cell decreases (resulting in, e.g., a reduction in the average steady state level of RNA transcript and/or protein encoded by the gene by at least 50%, 60%, 70%, 80%, 90%, 95%, or more) when the cell differentiates into a terminally differentiated cell.

A "pluripotency inducing gene" as used herein, refers to a gene whose expression, contributes to reprogramming somatic cells to a pluripotent state. "Pluripotency inducing factor" refers to an expression product of a pluripotency inducing gene. A pluripotency inducing factor may, but need not be, a pluripotency factor. Expression of an exogenously introduced pluripotency inducing factor may be transient, i.e., it may be needed during at least a portion of the reprogramming process in order to induce pluripotency and/or establish a stable pluripotent state but afterwards not required to maintain pluripotency. For example, the factor may induce expression of endogenous genes whose function is associated with pluripotency. These genes may then maintain the reprogrammed cells in a pluripotent state.

"Polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

"Polypeptide" refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual.

5.2. Abbreviations

A list of abbreviations used in the present disclosure is provided in Table 1 below.

TABLE 1

| Abbreviations | |
|---|---|
| Abbreviations | Definitions |
| bFGF | Basic fibroblastic growth factor |
| bp | Base pairs |
| Complete RPMI medium | RPMI + 10% FBS + 1 × Pen/Strep |
| DAPI | 4',6-diamidino-2-phenylindole |
| ddH$_2$O | Double distilled water |
| DMEM | Dulbecco's Modified Eagle Medium |
| DPBS | Dulbecco's phosphate buffered saline |
| ECM | Extracellular matrix |
| FACS | Fluorescence-activated cell sorting |
| FACS buffer | DPBS + 2% FBS |
| 6-FAM | 6-Carboxyfluorescein |
| FBS | Foetal bovine serum |
| FMO | Fluorescence minus one |
| FP/F | Forward Primer |
| IU | International Units |
| KLF4 | Kruppel-like factor 4 |
| mAb | Monoclonal antibody |
| MEF | Mouse embryonic fibroblasts |
| Oct-3 | Octamer-binding transcription factor-3 |
| PCR | Polymerase Chain Reaction |
| Pen/Strep | Penicillin and streptomycin |
| PBMCs | Peripheral blood mononuclear cells |
| rhIL-2 | Recombinant human Interleukin-2 |
| rhIL-15 | Recombinant human Interleukin-15 |
| rpm | Revolutions per minute |

TABLE 1-continued

| Abbreviations | |
|---|---|
| Abbreviations | Definitions |
| RPMI | Roswell Park Memorial Institute medium |
| RV/R | Reverse primer |
| SeV | Sendai virus |
| SSEA-4 | Stage-specific embryonic antigen-4 |
| MOI | Multiplicity of Infection |
| SOX2 | Sex determining region Y-box 2 |
| TRG | T cell receptor gamma locus |
| TRD | T cell receptor delta locus |
| Tg | Transgenic |
| x g | Gravity (or g-force) |
| V | Voltage |
| Zol | Zoledronic acid monohydrate |

5.3. Methods of Producing Induced Pluripotent Stem Cells (iPSCs)

In one aspect, provided herein are methods for reprogramming somatic cells (e.g., a T cell) to a less differentiated state. The resulting cells are called reprogrammed somatic cells herein. A reprogrammed somatic cell may be a reprogrammed somatic cell of varying differentiation status. In some embodiments, the reprogrammed somatic cell is an induced pluripotent stem cell (iPSC). The present disclosure is based in part on the surprising discovery that a combination of various factors, e.g., a combination of zoledronic acid and Interleukin-15 (IL-15), can activate γδ T cells and thus improve the efficiency of induction of pluripotency in non-pluripotent mammalian T cells transformed with transcription factors. Accordingly, in one aspect, the present disclosure provides for methods of inducing pluripotency in non-pluripotent mammalian γδ T cells (e.g., Vγ9$^+$ γδ T cells) wherein the method comprises contacting peripheral blood mononuclear cells (PBMCs) with an activation culture comprising IL-15 and zoledronic acid.

In some embodiments, provided herein are methods of reprogramming a somatic cell comprising: (a) contacting an isolated population of cells with an activation culture; wherein the activation culture comprises IL-15 and zoledronic acid; (b) culturing the isolated population of cells in the activation culture to enrich and/or activate γδ T cells in the isolated population of cells; (c) transducing the γδ T cells with one or more viral vector(s) encoding one or more reprogramming factors; and (d) culturing the transduced γδ T cells under conditions suitable for reprogramming mammalian somatic cells to a less differentiated state. In some embodiments, the less differentiated state is a multipotent state. In some embodiments, the less differentiated state is a pluripotent state.

In some more specific embodiments, provided herein are methods of producing induced pluripotent stem cells (iPSCs) comprising: (a) contacting an isolated population of cells with an activation culture; wherein the activation culture comprises IL-15 and zoledronic acid; (b) culturing the isolated population of cells in the activation culture to enrich and/or activate γδ T cells in the isolated population of cells; (c) transducing the γδ T cells with one or more viral vector(s) encoding one or more reprogramming factors; and (d) culturing the transduced γδ T cells under conditions suitable for reprogramming mammalian somatic cells to a pluripotent state.

In certain embodiments, the activation culture further comprises one or more additional agents or compounds, for example, to improve the efficiency of activation or induction. In one embodiment, the activation culture further comprises Interleukin-2 (IL-2).

Therefore, in some embodiments, provided herein are methods of reprogramming a somatic cell comprising: (a) contacting an isolated population of cells with an activation culture; wherein the activation culture comprises IL-15, zoledronic acid and IL-2; (b) culturing the isolated population of cells in the activation culture to enrich and/or activate γδ T cells in the isolated population of cells; (c) transducing the γδ T cells with one or more viral vector(s) encoding one or more reprogramming factors; and (d) culturing the transduced γδ T cells under conditions suitable for reprogramming mammalian somatic cells to a less differentiated state.

In some more specific embodiments, provided herein are methods of producing induced pluripotent stem cells (iPSCs) comprising: (a) contacting an isolated population of cells with an activation culture; wherein the activation culture comprises IL-15, zoledronic acid and IL-2; (b) culturing the isolated population of cells in the activation culture to enrich and/or activate γδ T cells in the isolated population of cells; (c) transducing the γδ T cells with one or more viral vector(s) encoding one or more reprogramming factors; and (d) culturing the transduced γδ T cells under conditions suitable for reprogramming mammalian somatic cells to a pluripotent state.

In certain embodiments, the method further comprises obtaining the isolated population of cells from a subject. In certain embodiments, the subject is a mammal. In certain embodiments, the subject is a human.

In certain embodiments, the isolated population of cells are peripheral blood cells, cord blood cells, or bone marrow cells. In one embodiment, the isolated population of cells are peripheral blood mononuclear cells (PBMCs).

Methods for identifying reprogrammed mammalian somatic cells with a less differentiated state or a pluripotent state are known in the art. For example, in some embodiments, reprogrammed somatic cells are identified by selecting for cells that express the appropriate selectable marker. In some embodiments, reprogrammed somatic cells are further assessed for pluripotency characteristics. The presence of pluripotency characteristics indicates that the somatic cells have been reprogrammed to a pluripotent state.

Differentiation status of cells is a continuous spectrum, with terminally differentiated state at one end of this spectrum and de-differentiated state (pluripotent state) at the other end. Reprogramming, as used herein, refers to a process that alters or reverses the differentiation status of a somatic cell, which can be either partially or terminally differentiated. Reprogramming includes complete reversion, as well as partial reversion, of the differentiation status of a somatic cell. In other words, the term "reprogramming," as used herein, encompasses any movement of the differentiation status of a cell along the spectrum toward a less-differentiated state. For example, reprogramming includes reversing a multipotent cell back to a pluripotent cell, reversing a terminally differentiated cell back to either a multipotent cell or a pluripotent cell. In one embodiment, reprogramming of a somatic cell turns the somatic cell all the way back to a pluripotent state. In another embodiment, reprogramming of a somatic cell turns the somatic cell back to a multipotent state. The term "less-differentiated state," as used herein, is thus a relative term and includes a completely de-differentiated state and a partially differentiated state.

The term "pluripotency characteristics" refers to many characteristics associated with pluripotency, including, for example, the ability to differentiate into all types of cells and an expression pattern distinct for a pluripotent cell, including expression of pluripotency genes, expression of other ES cell markers, and on a global level, a distinct expression profile known as "stem cell molecular signature" or "stemness."

Thus, to assess reprogrammed somatic cells for pluripotency characteristics, one may analyze such cells for different growth characteristics and ES cell-like morphology. In some embodiments, cells may be injected subcutaneously into immunocompromised SCID mice to induce teratomas (a standard assay for ES cells). ES-like cells can be differentiated into embryoid bodies (another ES specific feature). Moreover, ES-like cells can be differentiated in vitro by adding certain growth factors known to drive differentiation into specific cell types. Self-renewing capacity, marked by induction of telomerase activity, is another pluripotency characteristics that can be monitored.

In some embodiments, functional assays of the reprogrammed somatic cells may be conducted by introducing them into blastocysts to determine whether the cells are capable of giving rise to all cell types. If the reprogrammed cells are capable of forming a few cell types of the body, they are multipotent; if the reprogrammed cells are capable of forming all cell types of the body including germ cells, they are pluripotent.

In other embodiments, the expression of an individual pluripotency gene in the reprogrammed somatic cells may be examined to assess their pluripotency characteristics.

Additionally, one may assess the expression of other ES cell markers. Stage-specific embryonic 1 5 antigens-1, -3, and -4 (SSEA-1, SSEA-3, SSEA-4) are glycoproteins specifically expressed in early embryonic development and are markers for ES cells (Solter and Knowles, 1978, Proc. Natl. Acad. Sci. USA 75:5565-5569; Kannagi et al., 1983, EMBO J 2:2355-2361).

Elevated expression of the enzyme Alkaline Phosphatase (AP) is another marker associated with undifferentiated embryonic stem cells (Wobus et al., 1984, Exp. Cell 152: 212-219; Pease et al., 1990, Dev. Biol. 141:322-352). Other stem/progenitor cells markers include the intermediate neurofilament nestin (Lendahl et al., 1990, Cell 60:585-595; Dah-Istrand et al., 1992, J. Cell Sci. 103:589-597), the membrane glycoprotein prominin/AC133 (Weigmann et al., 1997, Proc. Natl. Acad. USA 94:12425-12430; Corbeil et al., 1998, Blood 91:2625-22626), the transcription factor Tcf-4 (Korinek et al, 1998, Nat. Genet. 19: 379-383; Lee et al., 1999, J. Biol. Chem. 274.1566-1572), and the transcription factor Cdxl (Duprey et al., 1988, Genes Dev. 2:1647-1654; Subramania'n et al., 1998, Differentiation 64:11-18).

In some embodiments, expression profiling of the reprogrammed somatic cells may be used to assess their pluripotency characteristics. Pluripotent cells, such as embryonic stem cells, and multipotent cells, such as adult stem cells, are known to have a distinct pattern of global gene expression profile. This distinct pattern is termed "stem cell molecular signature", or "stemness". See, for example, Ramalho-Santos et al., Science 298: 597-600 (2002); Ivanova et al., Science 298: 601-604.

Somatic cells may be reprogrammed to gain either a complete set of the pluripotency characteristics and are thus pluripotent. Alternatively, somatic cells may be reprogrammed to gain only a subset of the pluripotency characteristics. In another alternative, somatic cells may be reprogrammed to be multipotent.

Activation Culturing

In certain embodiments, the isolated population of cells are cultured in the activation culture for a first period of time. In certain embodiments, the first period of time is 1-20 days.

In certain embodiments, the first period of time is 1-17 days.
In certain embodiments, the first period of time is 1-15 days.
In certain embodiments, the first period of time is 1-13 days.
In certain embodiments, the first period of time is 1-11 days.
In certain embodiments, the first period of time is 1-9 days.
In certain embodiments, the first period of time is 1-7 days.
In certain embodiments, the first period of time is 1-5 days.
In certain embodiments, the first period of time is 1-3 days.
In certain embodiments, the first period of time 12-72 hours.
In certain embodiments, the first period of time 12-60 hours.
In certain embodiments, the first period of time 12-48 hours.
In certain embodiments, the first period of time 12-36 hours.
In certain embodiments, the first period of time 12-24 hours.
In certain embodiments, the first period of time 8-16 hours.
In certain embodiments, the first period of time 4-8 hours. In certain embodiments, the first period of time 2-4 hours. In certain embodiments, the first period of time 4-8 hours. In certain embodiments, the first period of time 50-80 hours. In certain embodiments, the first period of time 4-8 hours. In certain embodiments, the first period of time 55-75 hours. In certain embodiments, the first period of time 4-8 hours. In certain embodiments, the first period of time 60-75 hours. In certain embodiments, the first period of time 4-8 hours. In certain embodiments, the first period of time 70-75 hours. In certain embodiments, the first period of time is 1, 2, 3, 4, 5, 6, 7, 8, 9, 10, 11, 12, 13, 14, 15, 16, 17, 18, 19, or 20 days.

In certain embodiments, wherein the isolated population of cells are cultured in the activation culture no long than a certain period of time. For example, the isolated population of cells are cultured in the activation culture for at most 13 days, at most 12 days, at most 11 day, at most 10 days, at most 9 days, at most 8 days, at most 7 days, at most 6 days, at most 5 days, at most 4 days, at most 3 days, at most 2 days, or at most 1 day. In a specific embodiment, the isolated population of cells are cultured in the activation culture for at most 5 days. In a specific preferred embodiment, the isolated population of cells are cultured in the activation culture for at most 3 days. In a specific preferred embodiment, the isolated population of cells are cultured in the activation culture for about 3 days.

In certain embodiments, after being cultured in the activation culture for the first period of time, the isolated population of cells comprise 5%-100% γδ T cells. In certain embodiments, after being cultured in the activation culture for the first period of time, the isolated population of cells comprise 5%-95% γδ T cells. In certain embodiments, after being cultured in the activation culture for the first period of time, the isolated population of cells comprise 5%-90% γδ T cells. In certain embodiments, after being cultured in the activation culture for the first period of time, the isolated population of cells comprise 5%-85% γδ T cells. In certain embodiments, after being cultured in the activation culture for the first period of time, the isolated population of cells comprise 5%-80% γδ T cells. In certain embodiments, after being cultured in the activation culture for the first period of time, the isolated population of cells comprise 5%-75% γδ T cells. In certain embodiments, after being cultured in the activation culture for the first period of time, the isolated population of cells comprise 5%-70% γδ T cells. In certain embodiments, after being cultured in the activation culture for the first period of time, the isolated population of cells comprise 5%-65% γδ T cells. In certain embodiments, after being cultured in the activation culture for the first period of time, the isolated population of cells comprise 5%-60% γδ T cells. In certain embodiments, after being cultured in the activation culture for the first period of time, the isolated population of cells comprise 5%-55% γδ T cells. In certain embodiments, after being cultured in the activation culture for the first period of time, the isolated population of cells comprise 5%-50% γδ T cells. In certain embodiments, after being cultured in the activation culture for the first period of time, the isolated population of cells comprise 5%-45% γδ T cells. In certain embodiments, after being cultured in the activation culture for the first period of time, the isolated population of cells comprise 5%-40% γδ T cells. In certain embodiments, after being cultured in the activation culture for the first period of time, the isolated population of cells comprise 5%-35% γδ T cells. In certain embodiments, after being cultured in the activation culture for the first period of time, the isolated population of cells comprise 15%-35% γδ T cells. In certain embodiments, after being cultured in the activation culture for the first period of time, the isolated population of cells comprise 25%-35% γδ T cells. In certain embodiments, after being cultured in the activation culture for the first period of time, the isolated population of cells comprise 30%-35% γδ T cells. In certain embodiments, after being cultured in the activation culture for the first period of time, the isolated population of cells comprise 5%-30% γδ T cells. In certain embodiments, after being cultured in the activation culture for the first period of time, the isolated population of cells comprise 5%-25% γδ T cells. In certain embodiments, after being cultured in the activation culture for the first period of time, the isolated population of cells comprise 5%-20% γδ T cells. In certain embodiments, after being cultured in the activation culture for the first period of time, the isolated population of cells comprise 5%-15% γδ T cells.

In certain embodiments, after being cultured in the activation culture for the first period of time, the isolated population of cells comprise about 100%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5% γδ T cells. In certain embodiments, after being cultured in the activation culture for the first period of time, the isolated population of cells comprise less than about 90%, less than about 80%, less than about 70%, less than about 60%, less than about 50%, less than about 45%, less than about 40%, less than about 35%, or less than about 30% γδ T cells.

In one embodiment, after being cultured in the activation culture for the first period of time, the isolated population of cells comprise less than about 60% γδ T cells. In another embodiment, after being cultured in the activation culture for the first period of time, the isolated population of cells comprise less than about 55% γδ T cells. In yet another embodiment, after being cultured in the activation culture for the first period of time, the isolated population of cells comprise less than about 50% γδ T cells. In yet another embodiment, after being cultured in the activation culture for the first period of time, the isolated population of cells comprise less than about 45% γδ T cells. In yet another embodiment, after being cultured in the activation culture for the first period of time, the isolated population of cells comprise less than about 40% γδ T cells. In yet another embodiment, after being cultured in the activation culture for the first period of time, the isolated population of cells comprise less than about 35% γδ T cells.

In certain embodiments, after being cultured in the activation culture for the first period of time, the γδ T cells in the isolated population of cells comprise 5%-100% TCRVγ9+ T cells. In certain embodiments, after being cultured in the activation culture for the first period of time, the γδ T cells in the isolated population of cells comprise 5%-95%

TCRVγ9+ T cells. In certain embodiments, after being cultured in the activation culture for the first period of time, the γδ T cells in the isolated population of cells comprise 5%-90% TCRVγ9+ T cells. In certain embodiments, after being cultured in the activation culture for the first period of time, the γδ T cells in the isolated population of cells comprise 5%-85% TCRVγ9+ T cells. In certain embodiments, after being cultured in the activation culture for the first period of time, the γδ T cells in the isolated population of cells comprise 5%-80% TCRVγ9+ T cells. In certain embodiments, after being cultured in the activation culture for the first period of time, the γδ T cells in the isolated population of cells comprise 5%-75% TCRVγ9+ T cells. In certain embodiments, after being cultured in the activation culture for the first period of time, the γδ T cells in the isolated population of cells comprise 5%-70% TCRVγ9+ T cells. In certain embodiments, after being cultured in the activation culture for the first period of time, the γδ T cells in the isolated population of cells comprise 5%-65% TCRVγ9+ T cells. In certain embodiments, after being cultured in the activation culture for the first period of time, the γδ T cells in the isolated population of cells comprise 5%-60% TCRVγ9+ T cells. In certain embodiments, after being cultured in the activation culture for the first period of time, the γδ T cells in the isolated population of cells comprise 5%-55% TCRVγ9+ T cells. In certain embodiments, after being cultured in the activation culture for the first period of time, the γδ T cells in the isolated population of cells comprise 5%-50% TCRVγ9+ T cells. In certain embodiments, after being cultured in the activation culture for the first period of time, the γδ T cells in the isolated population of cells comprise 5%-45% TCRVγ9+ T cells. In certain embodiments, after being cultured in the activation culture for the first period of time, the γδ T cells in the isolated population of cells comprise 5%-40% TCRVγ9+ T cells. In certain embodiments, after being cultured in the activation culture for the first period of time, the γδ T cells in the isolated population of cells comprise 5%-35% TCRVγ9+ T cells. In certain embodiments, after being cultured in the activation culture for the first period of time, the γδ T cells in the isolated population of cells comprise 5%-30% TCRVγ9+ T cells. In certain embodiments, after being cultured in the activation culture for the first period of time, the γδ T cells in the isolated population of cells comprise 5%-25% TCRVγ9+ T cells. In certain embodiments, after being cultured in the activation culture for the first period of time, the γδ T cells in the isolated population of cells comprise 5%-20% TCRVγ9+ T cells. In certain embodiments, after being cultured in the activation culture for the first period of time, the γδ T cells in the isolated population of cells comprise 5%-15% TCRVγ9+ T cells.

In certain embodiments, after being cultured in the activation culture for the first period of time, the γδ T cells in the isolated population of cells comprise about 100%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% TCRVγ9$^+$ T cells (aka Vγ9$^+$ T cells). In certain embodiments, after being cultured in the activation culture for the first period of time, the γδ T cells in the isolated population of cells comprise less than about 90%, less than about 80%, less than about 70%, less than about 60%, less than about 50%, less than about 45%, less than about 40%, less than about 35%, or less than about 30% TCRVγ9$^+$ T cells.

In one embodiment, after being cultured in the activation culture for the first period of time, the γδ T cells in the isolated population of cells comprise less than about 60% TCRVγ9+ T cells. In one embodiment, after being cultured in the activation culture for the first period of time, the γδ T cells in the isolated population of cells comprise less than about 55% TCRVγ9+ T cells. In yet another embodiment, after being cultured in the activation culture for the first period of time, the γδ T cells in the isolated population of cells comprise less than about 50% TCRVγ9+ T cells. In yet another embodiment, after being cultured in the activation culture for the first period of time, the γδ T cells in the isolated population of cells comprise less than about 45% TCRVγ9+ T cells. In yet another embodiment, after being cultured in the activation culture for the first period of time, the γδ T cells in the isolated population of cells comprise less than about 40% TCRVγ9+ T cells. In yet another embodiment, after being cultured in the activation culture for the first period of time, the γδ T cells in the isolated population of cells comprise less than about 35% TCRVγ9+ T cells.

In certain embodiments, the method further comprises enriching the γδ T cells in the isolated population of cells. In certain embodiments, the γδ T cells are enriched by cell-cell clump enrichment.

In certain embodiments, at least part of the activated γδ T cells in step (b) are Vγ9$^+$ γδ T cells.

In certain embodiments, at least part of the activated γδ T cells in step (b) are Vγ9δ2$^+$ γδ T cells.

Cells

The present disclosure is predicated on the discovery that an isolated population of cells, e.g., an isolated population of γδ T cells, can be activated and reprogramed to pluripotency by activation (e.g., in presence of zoledronic acid and IL-15) and introduction of transcription factors (e.g., by Sendai virus vector).

The isolated population of cells of the present disclosure include any T cell of the body that is not a stem cell, a germ cell, or an iPSC. Non-limiting examples of a non-iPSC is a T cell derived from any tissue of the body, including internal organs, skin, bones, blood, nervous tissue, and connective tissue.

In certain embodiments, the isolated population of cells are blood cells. In certain embodiments, the blood cells are suitably peripheral blood mononuclear cells (PMBCs), and may include all types of blood cells existing on an entire differentiation process from hematopoietic stem cells to final differentiation into peripheral blood. In one embodiment, the blood cells include, for example, hematopoietic stem cells, lymphoid stem cells, lymphoid dendritic cell progenitor cells, lymphoid dendritic cells, T lymphocyte progenitor cells, T cells, B lymphocyte progenitor cells, B cells, plasma cells, NK progenitor cells, NK cells, monocytes, and macrophages.

In some embodiments, the isolated population of cells can be can be peripheral blood mononuclear cells (PBMC), peripheral blood leukocytes (PBL), tumor infiltrating lymphocytes (TIL), or a combination thereof. In some embodiments, the isolated population of cells are peripheral blood mononuclear (PBMC) cells.

In certain embodiments, the isolated population cells are T cells. In some embodiment, the isolated population of T cells can be selected from the group consisting of CD4+/CD8+ double positive T cells, cytotoxic T cells, Th3 (Treg) cells, Th9 cells, Thαβ helper cells, Tfh cells, stem memory TSCM cells, central memory TCM cells, effector memory TEM cells, effector memory TEMRA cells, gamma delta T cells and any combination thereof.

In some embodiments, the isolated population of cells is derived from a cell type that is easily accessible and requires minimal invasion, such as a fibroblast, a skin cell, a cord blood cell, a peripheral blood cell, and a renal epithelial cell.

In certain embodiments, the isolated population of cells are terminally differentiated cells. In certain embodiments, the isolated population of cells are terminally differentiated T cells. In certain embodiments, the isolated population of cells are terminally differentiated PBMC cells. In certain embodiments, the isolated population of cells are terminally differentiated γδ T cells.

The isolated population of cells of the present disclosure may be derived from a mammal, preferably a human, but include and are not limited to non-human primates, murines (i.e., mice and rats), canines, felines, equines, bovines, ovines, porcines, caprines, etc.

In certain embodiments, the isolated population of cells are mammal cells.

In certain embodiments, the isolated population of cells are human cells.

In some embodiments, the isolated population of cells are human PBMC cells.

Introduction of Pluripotency-Associated Genes

The present disclosure also relates to introducing into the activated population of cells an endogenous gene locus that is a pluripotency-associated gene. In some embodiments, such pluripotency-associated gene can be introduced using an expression vector. In some embodiments, such pluripotency-associated gene can be introduced using the CRISPR activation system with at least one sgRNA targeting the desired gene locus. In some embodiments, such pluripotency-associated gene can be introduced by expression from a recombinant expression cassette that has been introduced into the target cell. In some embodiments, such pluripotency-associated gene can be introduced by incubating the cells in the presence of exogenous reprogramming transcription factor polypeptides.

In certain embodiments, the expression vector used to introduce pluripotency-associated gene includes a modified viral polynucleotide, such as from an adenovirus, a Sendai virus, a herpesvirus, or a retrovirus, such as a lentiviral vector. The expression vector is not restricted to recombinant viruses and includes non-viral vectors such as DNA plasmids and in vitro transcribed mRNA. In one preferred embodiment, Sendai virus vector is used.

To address the safety issues that arise from target cell genomes harboring integrated exogenous sequences, a number of modified genetic protocols have been developed and can be used in the methods of producing described herein. These protocols produce iPS cells with potentially reduced risks, and include non-integrating adenoviruses to deliver reprogramming genes (Stadtfeld, M., et al., Science, 2008, 322:945-949), transient transfection of reprogramming plasmids (Okita, K., et al., Science, 2008, 322:949-953), piggyBac transposition systems (Woltjen, K., et al., Nature, 2009, 458:766-770; Yusa, et al., Nat. Methods, 2009, 6:363-369; Kaji, K., et al. (2009)), Cre-excisable viruses (Soldner, F., et al., Cell, 2009, 136:964-977), and oriP/EBNA1-based episomal expression system (Yu, J., et al., Science, 2009, 324(5928): 797-801).

Non-limiting examples of a pluripotency-associated gene (gene that encode a reprogramming transcription factor) are Oct3/4, Sox2, Nanog, Klf4, c-Myc, Nanog, Lin28, Nr5a2, Glis1, Cebpa, Esrrb, and Rex1. In some embodiments, the endogenous gene locus is Oct4 or Sox2.

In certain embodiments, the isolated population of cells endogenously express at least one or more proteins from the group consisting of Oct3/4 polypeptide, a Klf4 polypeptide, a c-Myc polypeptide, a Sox2 polypeptide, a Nanog polypeptide, a Lin28 polypeptide, a Nr5a2 polypeptide, a Glis1 polypeptide, a Cebpa polypeptide, a Esrrb polypeptide, and a Rex1 polypeptide. In certain embodiments, the isolated population of cells do not endogenously express any reprogramming transcription factor.

In certain embodiment, the reprogramming factors comprise Oct3/4, Sox2, Klf4, and c-Myc.

In certain embodiments, the reprogramming factors are Oct3/4, Sox2, KLF4, c-Myc, and Lin28.

In certain embodiment, the reprogramming factors are Oct3/4, Sox2, Klf4, c-Myc.

The exogenously introduced pluripotency gene may be carried out in several ways. In one embodiment, the exogenously introduced pluripotency gene may be expressed from a chromosomal locus different from the endogenous chromosomal locus of the pluripotency gene. Such chromosomal locus may be a locus with open chromatin structure, and contain gene(s) dispensable for a somatic cell. In other words, the desirable chromosomal locus contains gene(s) whose disruption will not cause cells to die. Exemplary chromosomal loci include, for example, the mouse ROSA 26 locus and type II collagen (Col2a1) locus (See Zambrowicz et al., 1997)

The exogenously introduced pluripotency gene may be expressed from an inducible promoter such that their expression can be regulated as desired.

In an alternative embodiment, the exogenously introduced pluripotency gene may be transiently transfected into cells, either individually or as part of a cDNA expression library, prepared from pluripotent cells. Such pluripotent cells may be embryonic stem cells, oocytes, blastomeres, inner cell mass cells, embryonic germ cells, embryoid body (embryonic) cells, morula-derived cells, teratoma (teratocarcinoma) cells, and multipotent partially differentiated embryonic stem cells taken from later in the embryonic development process.

The cDNA library is prepared by conventional techniques. Briefly, mRNA is isolated from an organism of interest. An RNA-directed DNA polymerase is employed for first strand synthesis using the mRNA as template. Second strand synthesis is carried out using a DNA-directed DNA polymerase which results in the cDNA product. Following conventional processing to facilitate cloning of the cDNA, the cDNA is inserted into an expression vector such that the cDNA is operably linked to at least one regulatory sequence. The choice of expression vectors for use in connection with the cDNA library is not limited to a particular vector. Any expression vector suitable for use in mouse cells is appropriate. In one embodiment, the promoter which drives expression from the cDNA expression construct is an inducible promoter. The term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express cDNAs. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The exogenously introduced pluripotency gene may be expressed from an inducible promoter. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee et al. P.N.A.S. USA (1988), 85, 1204-1208; (1981), 294, 228-232; Klock et al. Nature (1987), 329, 734-736; Israel and Kaufman, Nucleic Acids Res. (1989), 17, 2589-2604), promoters that respond to chemical agents, such as glucose, lactose, galactose or antibiotic.

A tetracycline-inducible promoter is an example of an inducible promoter that responds to an antibiotics. See Gossen et al., 2003. The tetracycline-inducible promoter comprises a minimal promoter linked operably to one or more tetracycline operator(s). The presence of tetracycline or one of its analogues leads to the binding of a transcription activator to the tetracycline operator sequences, which activates the minimal promoter and hence the transcription of the associated cDNA. Tetracycline analogue includes any compound that displays structural homologies with tetracycline and is capable of activating a tetracycline-inducible promoter. Exemplary tetracycline analogues includes, for example, doxycycline, chlorotetracycline and anhydrotetracycline.

Thus, in one embodiment, the present disclosure provides somatic cells carrying at least one pluripotency gene expressed as a transgene under an inducible promoter. It is possible that somatic cells with such inducible pluripotency transgene(s) are more prone to be reprogrammed.

Any of the engineered somatic cells of the present disclosure may be used in the methods. In one embodiment, somatic cells used in the methods comprise only one endogenous pluripotency gene linked to a first selectable marker, and the selection step is carried out to select for the expression of the first selectable marker. In an alternative embodiment, the somatic cells used in the methods comprise any number of endogenous pluripotency genes, each of which is linked to a distinct selectable marker respectively, and the selection step is carried out to select for at least a subset of the selectable markers. For example, the selection step may be carried out to select for all the selectable markers linked to the various endogenous pluripotency genes.

In an alternative embodiment, somatic cells used in the method comprise a selectable marker linked to an endogenous pluripotency gene and an additional pluripotency gene expressed as a transgene under an inducible promoter. For these cells, the method of reprogramming may comprises induce the expression of the pluripotency transgene and select for the expression of the selectable marker.

In certain embodiments, in step (d) described in the method above, the transduced γδ T cells are cultured in the presence of one or more feeder layers. In certain embodiments, in step (d) the transduced γδ T cells are cultured in the presence of a mono layer of feeder layer. In certain embodiments, the feeder layer comprises mouse embryonic fibroblasts (MEFs). In certain embodiments, in step (d) the transduced γδ T cells are cultured in the presence of a mono layer of feeder layer. In certain embodiments, in step (d) the transduced γδ T cells are cultured in the presence of mitotically inactivated mouse embryonic fibroblasts (MEFs). In certain embodiments, in step (d) the transduced γδ T cells are cultured under feeder free condition. In certain embodiment, in step (d) the transduced yS T cells are cultured in iMatrix-511 coated plates.

In certain embodiments, following step (d) the method further comprises step (e) isolating and/or purifying the produced iPSCs.

In certain more specific embodiments, provided herein is a method of producing induced pluripotent stem cells (iPSCs) comprising: contacting an isolated population of cells with an activation culture; wherein the activation culture comprises IL-15, zoledronic acid and IL-2; culturing the isolated population of cells in the activation culture to enrich and/or activate γδ T cells in the isolated population of cells; transducing the γδ T cells with a Sendai virus (SeV) vector encoding one or more reprogramming factors; and culturing the transduced γδ T cells under conditions suitable for reprogramming mammalian somatic cells to a pluripotent state.

In certain more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture to enrich and/or activate γδ T cells in the isolated population of cells; transducing the γδ T cells with a Sendai virus (SeV) vector encoding one or more reprogramming factors; and culturing the transduced γδ T cells under conditions suitable for reprogramming mammalian somatic cells to a pluripotent state.

In other more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture for about 3 days to enrich and/or activate γδ T cells in the isolated population of cells; transducing the γδ T cells with a Sendai virus (SeV) vector encoding one or more reprogramming factors; and culturing the transduced γδ T cells under conditions suitable for reprogramming mammalian somatic cells to a pluripotent state.

In other more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture for about 3 days so that after being cultured in the activation culture the isolated population of cells comprise less than 35% γδ T cells; transducing the γδ T cells with a Sendai virus (SeV) vector encoding one or more reprogramming factors; and culturing the transduced γδ T cells under conditions suitable for reprogramming mammalian somatic cells to a pluripotent state.

In other more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture for about 3 days so that after being cultured in the activation culture the isolated population of cells comprise less than 35% γδ T cells; further enriching γδ T cells by cell-cell clump enrichment; transducing the γδ T cells with a Sendai virus (SeV) vector encoding one or more reprogramming factors; and culturing the transduced γδ T cells under conditions suitable for reprogramming mammalian somatic cells to a pluripotent state.

In other more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture for about 3 days so that after being cultured in the activation culture the isolated population of cells comprise less than 35% γδ T cells; optionally further enriching γδ T cells by cell-cell clump enrichment; transducing the γδ T cells with a Sendai virus (SeV) vector encoding one or more reprogramming factors selected from a group consisting of OCT3/4, SOX2, KLF4, LIN28, and c-Myc; and culturing the transduced γδ T cells under conditions suitable for reprogramming mammalian somatic cells to a pluripotent state.

In other more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture for about 3 days so that after being cultured in the activation culture the isolated population of cells comprise less than 35% γδ T cells; optionally further enriching γδ T cells by cell-cell clump enrichment; transducing the γδ T cells with a Sendai virus (SeV) vector encoding one or more reprogramming factors selected from a group consisting of OCT3/4, SOX2, KLF4, LIN28, and c-Myc; and culturing the transduced γδ T cells under conditions suitable for reprogramming mammalian somatic cells to a pluripotent state in the presence of one or more layers of feeder layer.

In other more specific embodiments, provided herein is a method of producing induced pluripotent stem cells (iPSCs) comprising: obtaining an isolated population of cells (e.g., terminally differentiated cells such as peripheral blood mononuclear cells (PBMCs)) from a subject (e.g., a human); contacting an isolated population of cells with an activation culture; wherein the activation culture comprises IL-15, zoledronic acid and IL-2; culturing the isolated population of cells in the activation culture for about 3 days so that after being cultured in the activation culture the isolated population of cells comprise less than 35% γδ T cells; optionally further enriching γδ T cells by cell-cell clump enrichment; transducing the γδ T cells with a Sendai virus (SeV) vector encoding one or more reprogramming factors selected from a group consisting of OCT3/4, SOX2, KLF4, LIN28, and c-Myc; and culturing the transduced γδ T cells under conditions suitable for reprogramming mammalian somatic cells to a pluripotent state in the presence of a mono layer of feeder layer that comprises mouse embryonic fibroblasts (MEFs).

iPSCs Derived from γδ T Cells

In certain embodiments, the produced iPSCs are derived from γδ T cells. In certain embodiments, the produced iPSCs have rearrangement genes of TRG and TRD gene loci. In certain embodiments, the produced iPSCs do not produce polymerase chain reaction (PCR) products from TCRG and TCRD gene loci.

In certain embodiments, the produced iPSCs are not derived from αβ T cells.

In certain embodiments, the produced iPSCs are negative for a Sendai virus (SeV) vector.

In certain embodiments, the produced iPSCs are genomically stable with no loss of a chromosome. In one embodiment, the genomic stability of the produced iPSCs is determined by Karyotyping analysis.

In certain embodiments, the produced iPSCs can grow and maintain in feeder free medium after adoption.

In certain embodiments, the method further comprises differentiating the produced iPSCs to a desired cell type in vitro or ex vivo. In certain embodiments, the method further comprises differentiating the produced iPSCs to a desired cell type in vitro. In certain embodiments, the method further comprises differentiating the produced iPSCs to a desired cell type ex vivo.

In certain embodiments, the method further comprises administering the produced iPSCs to a subject.

In certain embodiments, the method further comprises administering the differentiated cells that are differentiated from the iPSCs produced herein to a subject.

5.4. T-Cell Derived Induced Pluripotent Stem Cells (iPSCs)

Also provided here are isolated populations of induced pluripotent stem cells (iPSCs) with novel characteristics. In some embodiments, the isolated population of iPSCs comprise pluripotent cells that express one or more reprogramming factors, and comprise a nucleotide sequence encoding rearrangement of TRG and TRD genes.

In certain embodiments, the isolated populations of iPSCs are produced according to the methods described herein (e.g., in Section 5.3).

In certain embodiments, the reprogramming factors are selected from a group consisting of Oct3/4, Sox2, Klf4, c-Myc, and Lin28.

In certain embodiment, the reprogramming factors comprise Oct3/4, Sox2, Klf4, and c-Myc.

In certain embodiments, the reprogramming factors are Oct3/4, Sox2, KLF4, c-Myc, and Lin28.

In certain embodiment, the reprogramming factors are Oct3/4, Sox2, Klf4, and c-Myc.

In certain embodiments, the isolated population of iPSCs are derived from γδ T cells. In certain embodiments, the isolated population of iPSCs have rearrangement genes of TRG and TRD gene loci. In certain embodiments, the isolated population of iPSCs do not produce PCR products from TCRG and TCRD gene loci.

In certain embodiments, the isolated population of iPSCs are not derived from αβ T cells. In certain embodiments, the isolated population of iPSCs do not have rearrangement genes of TRA and TRB gene loci. In certain embodiments, the isolated population of iPSCs do not produce PCR products from TCRA and TCRB gene loci.

In certain embodiments, the isolated population of iPSCs are negative for a Sendai virus (SeV) vector.

In certain embodiments, the isolated population of iPSCs are genomically stable with no loss of a chromosome. In one embodiment, the genomic stability of the isolated population of iPSCs is determined by Karyotyping analysis.

In certain embodiments, the isolated population of iPSCs can grow and maintain in feeder free medium after adoption.

In some embodiments, provided herein is an isolated population of induced pluripotent stem cells (iPSCs) comprising pluripotent cells that express one or more reprogramming factors, wherein (i) the pluripotent cells comprise a nucleotide sequence encoding rearrangement of TRG and TRD genes or have rearrangement genes of TRG and TRD gene loci, (ii) the reprogramming factors are selected from a group consisting of Oct3/4, Sox2, Klf4, c-Myc, and Lin28, (iii) the isolated population of iPSCs are negative for a Sendai virus (SeV) vector; (iv) the isolated population of iPSCs are derived from γδ T cells, but not from αβ T cells; (v) the isolated population of iPSCs do not produce PCR products from TCRA and TCRB gene loci; (vi) the isolated population of iPSCs are genomically stable with no loss of a chromosome, e.g., as determined by Karyotyping analysis; and/or (vii) the isolated population of iPSCs can grow and maintain in feeder free medium after adoption.

In a specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, and wherein the reprogramming factors are selected from a group consisting of Oct3/4, Sox2, Klf4, c-Myc, and Lin28.

In another specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, and wherein the reprogramming factors are Oct3/4, Sox2, Klf4, c-Myc, and Lin28.

In yet another specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, and wherein the reprogramming factors are Oct3/4, Sox2, Klf4, and c-Myc.

In yet another specific embodiments, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, and the isolated population of iPSCs are negative for a Sendai virus (SeV) vector.

In yet another specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, the reprogramming factors are selected from a group consisting of Oct3/4, Sox2, Klf4, c-Myc, and Lin28, and the isolated population of iPSCs are negative for a Sendai virus (SeV) vector.

In yet another specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, and the isolated population of iPSCs are derived from γδ T cells, but not from αβ T cells.

In yet another specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes, and the isolated population of iPSCs do not produce PCR products from TCRA and TCRB gene loci.

In yet another specific embodiment, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes or have rearrangement genes of TRG and TRD gene loci, and the isolated population of iPSCs are genomically stable with no loss of a chromosome, e.g., as determined by Karyotyping analysis.

In yet another specific embodiments, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes or have rearrangement genes of TRG and TRD gene loci, and the isolated population of iPSCs can grow and maintain in feeder free medium after adoption.

In yet another specific embodiments, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes or have rearrangement genes of TRG and TRD gene loci, the reprogramming factors are selected from a group consisting of Oct3/4, Sox2, Klf4, c-Myc, and Lin28, the isolated population of iPSCs are negative for a Sendai virus (SeV) vector; the isolated population of iPSCs are derived from γδ T cells, but not from αβ T cells; the isolated population of iPSCs do not produce PCR products from TCRA and TCRB gene loci; the isolated population of iPSCs are genomically stable with no loss of a chromosome, e.g., as determined by Karyotyping analysis; and the isolated population of iPSCs can grow and maintain in feeder free medium after adoption.

In yet another specific embodiments, provided herein is an isolated population of induced pluripotent stem cells (iPSCs) comprising pluripotent cells that express one or more reprogramming factors, wherein the pluripotent cells comprise a nucleotide sequence encoding rearrangement of TRG and TRD genes or have rearrangement genes of TRG and TRD gene loci, the reprogramming factors are selected from a group consisting of Oct3/4, Sox2, Klf4, c-Myc, and Lin28, the isolated population of iPSCs are negative for a Sendai virus (SeV) vector; the isolated population of iPSCs do not produce PCR products from TCRA and TCRB gene loci; the isolated population of iPSCs are genomically stable with no loss of a chromosome, e.g., as determined by Karyotyping analysis; and the isolated population of iPSCs can grow and maintain in feeder free medium after adoption.

In yet another specific embodiments, provided herein is an isolated population of induced pluripotent stem cells (iPSCs) comprising pluripotent cells, wherein the pluripotent cells comprise a nucleotide sequence encoding rearrangement of TRG and TRD genes or have rearrangement genes of TRG and TRD gene loci, the isolated population of iPSCs are negative for a Sendai virus (SeV) vector; the isolated population of iPSCs are derived from γδ T cells, but not from αβ T cells; the isolated population of iPSCs do not produce PCR products from TCRA and TCRB gene loci; the isolated population of iPSCs are genomically stable with no loss of a chromosome, e.g., as determined by Karyotyping analysis; and the isolated population of iPSCs can grow and maintain in feeder free medium after adoption.

In yet another specific embodiments, provided herein is an isolated population of induced pluripotent stem cells (iPSCs) comprising pluripotent cells, wherein the pluripotent cells comprise a nucleotide sequence encoding rearrangement of TRG and TRD genes or have rearrangement genes of TRG and TRD gene loci, the isolated population of iPSCs are negative for a Sendai virus (SeV) vector; the isolated population of iPSCs do not produce PCR products from TCRA and TCRB gene loci; the isolated population of iPSCs are genomically stable with no loss of a chromosome, e.g., as determined by Karyotyping analysis; and the isolated population of iPSCs can grow and maintain in feeder free medium after adoption.

In yet another specific embodiments, provided herein is an isolated population of induced pluripotent stem cells (iPSCs) comprising pluripotent cells, wherein the pluripotent cells comprise a nucleotide sequence encoding rearrangement of TRG and TRD genes or have rearrangement genes of TRG and TRD gene loci, the isolated population of iPSCs do not produce PCR products from TCRA and TCRB gene loci; the isolated population of iPSCs are genomically stable with no loss of a chromosome, e.g., as determined by Karyotyping analysis; and the isolated population of iPSCs can grow and maintain in feeder free medium after adoption.

In yet another specific embodiments, provided herein is an isolated population of induced pluripotent stem cells (iPSCs) comprising pluripotent cells, wherein the pluripotent cells comprise a nucleotide sequence encoding rearrangement of TRG and TRD genes or have rearrangement genes of TRG and TRD gene loci, the isolated population of iPSCs do not produce PCR products from TCRA and TCRB gene loci; and the isolated population of iPSCs are genomically stable with no loss of a chromosome, e.g., as determined by Karyotyping analysis.

5.5. Pharmaceutical Compositions

Also provided herein are "pharmaceutical compositions," which comprise the produced iPSCs according to the method described herein, or differentiated cells therefrom, and one or more pharmaceutically acceptable carriers. In a particular embodiment, the produced iPSCs or differentiated cells therefrom are present in a therapeutically effective amount. In a particular embodiment, the produced iPSCs or differentiated cells therefrom are present in a prophylactically effective amount. The pharmaceutical compositions can be used in accordance with the methods and uses provided herein. Thus, for example, the pharmaceutical compositions can be administered to a subject in order to practice the treatment or prevention methods and uses provided herein. Pharmaceutical compositions provided herein can be formulated to be compatible with the intended method or route of administration; exemplary routes of administration are set forth herein.

Pharmaceutical compositions typically comprise a therapeutically effective amount of at least one of the produced iPSCs or differentiated cells therefrom, and a pharmaceutically acceptable carrier. Suitable pharmaceutically acceptable carriers include, but are not limited to, antioxidants (e.g., ascorbic acid), preservatives (e.g., benzyl alcohol, methyl parabens, p-hydroxybenzoate), emulsifying agents, suspending agents, dispersing agents, solvents, buffers, lubricants, fillers, and/or diluents. For example, a suitable vehicle may be physiological saline solution. Typical buffers that can be used include, but are not limited to pharmaceutically acceptable weak acids, weak bases, or mixtures thereof. Buffer components can also include water soluble reagents such as phosphoric acid, tartaric acids, succinic acid, citric acid, acetic acid, and salts thereof.

A vehicle may contain other pharmaceutically acceptable excipients for modifying or maintaining the pH, osmolarity, viscosity, or stability of the pharmaceutical composition. In a specific embodiment, the vehicle is an aqueous buffer. In a specific embodiment, a vehicle comprises, for example, sodium chloride.

Pharmaceutical compositions provided herein may contain still other pharmaceutically acceptable formulation agents for modifying or maintaining the rate of administration of the produced iPSCs or differentiated cells therefrom described herein. Such formulation agents include, for example, those substances known to those skilled in the art in preparing sustained-release or controlled release formulations. Regarding pharmaceutically acceptable formulation agents, see, for example, *Remington's Pharmaceutical Sciences*, 18th Ed. (1990, Mack Publishing Co., Easton, Pa. 18042) pages 1435-1712, and *The Merck Index*, 12th Ed. (1996, Merck Publishing Group, Whitehouse, NJ).

In specific embodiments, a pharmaceutical composition is provided in a single-use container (e.g., a single-use vial, ampoule, syringe, or autoinjector). In a specific embodiment, a pharmaceutical composition is provided in a multi-use container (e.g., a multi-use vial or cartridge). Any drug delivery apparatus may be used to deliver iPSCs or pharmaceutical composition described herein, including intravenous infusion.

A pharmaceutical composition can be formulated to be compatible with its intended route of administration as described herein.

Pharmaceutical compositions can also include carriers to protect the composition against degradation or elimination from the body. Various antibacterial and antifungal agents, for example, parabens, chlorobutanol, ascorbic acid, thimerosal, can be included in the pharmaceutical composition.

5.6. Therapeutic Methods and Uses

Also provided herein are reprogrammed somatic cells, including reprogrammed pluripotent somatic cells such as iPSCs, produced by the methods of the present disclosure. These methods, useful for the generation of cells of a desired cell type have wide range of applications. For one example, these methods have medical application in treating or preventing a condition.

Accordingly, in one aspect provided herein are methods for the treatment or prevention of a disease or disorder in a mammal. In one embodiment, the methods start with obtaining somatic cells from the individual, reprogramming the somatic cells so obtained by methods of the present invention to obtain iPSCs. The iPSCs are then cultured under conditions suitable for development of the iPSCs into cells of a desired cell type. The developed cells of the desired cell type are harvested and introduced into the individual to treat the disease or disorder. In an alternative embodiment, the methods start with obtaining somatic cells from the individual, reprogramming the somatic cells according to the present methods. The iPSCs are then cultured under conditions suitable for development of the iPSCs into a desired organ, which is harvested and introduced into the individual to treat the disease or disorder.

In some embodiments, the reprogramed somatic cells of the present invention are ES-like cells, and thus may be induced to differentiate to obtain the desired cell types according to known methods to differentiate ES cells. For example, the iPSCs may be induced to differentiate into hematopoietic stem cells, muscle cells, cardiac muscle cells, liver cells, cartilage cells, epithelial cells, urinary tract cells, etc., by culturing such cells in differentiation medium and under conditions which provide for cell differentiation. Medium and methods which result in the differentiation of embryonic stem cells are known in the art as are suitable culturing conditions.

In some specific embodiments, the iPSCs are induced to differentiate into hematopoietic stem cells, for example, as described in Palacios et al., Proc. Natl. Acad. Sci., USA, 92: 7530-37 (1995), which teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferal of cell aggregates to a substrate which provides for cell attachment.

In other specific embodiments, the iPSC are induced to differentiate according to methods as described in Pedersen, J. Reprod. Fertil. Dev., 6: 543-52 (1994), which references numerous articles disclosing methods for in vitro differentiation of embryonic stem cells to produce various differentiated cell types including hematopoietic cells, muscle, cardiac muscle, nerve cells, among others.

In other specific embodiments, the iPSC are induced to differentiate according to Bain et al., Dev. Biol., 168:342-357 (1995), which teaches in vitro differentiation of embryonic stem cells to produce neural cells which possess neuronal properties.

These references are exemplary of reported methods for obtaining differentiated cells from embryonic or stem-like cells. These references and in particular the disclosures therein relating to methods for differentiating embryonic stem cells are incorporated by reference in their entirety herein.

Thus, using known methods and culture medium, one skilled in the art may culture the subject embryonic or stem-like cells to obtain desired differentiated cell types, e.g., neural cells, muscle cells, hematopoietic cells, etc. In addition, the use of inducible Bcl-2 or Bcl-xl might be useful for enhancing in vitro development of specific cell lineages. In vivo, Bcl-2 prevents many, but not all, forms of apoptotic cell death that occur during lymphoid and neural development. A thorough discussion of how Bcl-2 expression might be used to inhibit apoptosis of relevant cell lineages following transfection of donor cells is disclosed in U.S. Pat. No. 5,646,008, which is herein incorporated by reference.

The iPSCs provided herein may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system. Hematopoietic stem cells can be obtained, e.g., by fusing adult somatic cells of a cancer or AIDS patient, e.g., epithelial cells or lymphocytes with an enucleated oocyte, e.g., bovine oocyte, obtaining embryonic or stem-like cells as described above, and culturing such cells under conditions which favor differentiation, until hematopoietic stem cells are obtained. Such hematopoietic cells may be used in the treatment of diseases including cancer and AIDS.

The methods of the present invention can also be used to treat, prevent, or stabilize a neurological disease such as Alzheimer's disease, Parkinson's disease, Huntington's disease, or ALS, lysosomal storage diseases, multiple sclerosis, or a spinal cord injury. For example, somatic cells may be obtained from the individual in need of treatment, and reprogrammed to gain pluripotency, and cultured to derive neurectoderm cells that may be used to replace or assist the normal function of diseased or damaged tissue.

For the treatment or prevention of endocrine conditions, reprogramed cells that produce a hormone, such as a growth factor, thyroid hormone, thyroid-stimulating hormone, parathyroid hormone, steroid, serotonin, epinephrine, or norepinephrine may be administered to a mammal. Additionally, reprogrammed epithelial cells may be administered to repair damage to the lining of a body cavity or organ, such as a lung, gut, exocrine gland, or urogenital tract. It is also contemplated that iPSCs may be administered to a mammal to treat damage or deficiency of cells in an organ such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

The great advantage of the present disclosure is that it provides an essentially limitless supply of isogenic or synegenic human cells suitable for transplantation. Therefore, it will obviate the significant problem associated with current transplantation methods, i.e., rejection of the transplanted tissue which may occur because of host versus graft or graft versus host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs, such as cyclosporine, imulan, FK-506, glucocorticoids, and rapamycin, and derivatives thereof.

iPSCs may also be combined with a matrix to form a tissue or organ in vitro or in vivo that may be used to repair or replace a tissue or organ in a recipient mammal. For example, iPSCs may be cultured in vitro in the presence of a matrix to produce a tissue or organ of the urogenital system, such as the bladder, clitoris, corpus cavermosum, kidney, testis, ureter, uretal valve, or urethra, which may then be transplanted into a mammal (Atala, Curr. Opin. Urol. 9(6):517-526, 1999). In another transplant application, synthetic blood vessels are formed in vitro by culturing reprogrammed cells in the presence of an appropriate matrix, and then the vessels are transplanted into a mammal for the treatment or prevention of a cardiovascular or circulatory condition. For the generation of donor cartilage or bone tissue, iPSCs such as chondrocytes or osteocytes are cultured in vitro in the presence of a matrix under conditions that allow the formation of cartilage or bone, and then the matrix containing the donor tissue is administered to a mammal. Alternatively, a mixture of the cells and a matrix may be administered to a mammal for the formation of the desired tissue in vivo. Preferably, the cells are attached to the surface of the matrix or encapsulated by the matrix. Examples of matrices that may be used for the formation of donor tissues or organs include collagen matrices, carbon fibers, polyvinyl alcohol sponges, acrylateamide sponges, fibrin-thrombin gels, hyaluronic acid-based polymers, and synthetic polymer matrices containing polyanhydride, polyorthoester, polyglycolic acid, or a combination thereof (see, for example, U.S. Pat. Nos. 4,846,835; 4,642,120; 5,786, 217; and 5,041,138).

The iPSCs produced according to the disclosure may be used to produce genetically engineered or transgenic differentiated cells. Essentially, this will be effected by introducing a desired gene or genes, or removing all or part of an endogenous gene or genes of iPSCs produced according to the invention, and allowing such cells to differentiate into the desired cell type. A preferred method for achieving such modification is by homologous recombination because such technique can be used to insert, delete or modify a gene or genes at a specific site or sites in the stem-like cell genome.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor maybe introduced into human embryonic or stem-like cells, the cells differentiated into neural cells and the cells transplanted into a Parkinson's patient to retard the loss of neural cells during such disease. Examples of mutations that may be rescued using these methods include mutations in the cystic fibrosis gene; mutations associated with Dunningan's disease such as the R482W, R482Q, and R584H mutations in the lamin A gene; and mutations associated with the autosomal-dominant form of Emery Deyfuss muscular dystrophy such as the R249Q, R453W, and Q6STOP mutations in the lamin A gene. In the Q6STOP mutation, the codon for Gln6 is mutated to a stop codon.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., Brain Research, 691:25-36, (1995)). This ex vivo therapy reduced Parkinson's-like symptoms in the rats up to 45% 32 days after transfer. Also, the tyrosine hydroxylase gene has been placed into astrocytes with similar results (Lundberg et al., Develop. Neurol., 139:39-53 (1996) and references cited therein).

However, such ex vivo systems have problems. In particular, retroviral vectors currently used are down-regulated in vivo and the transgene is only transiently expressed (review by Mulligan, Science, 260: 926-932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques.

By contrast, the difficulties associated with retroviral systems should be eliminated by the use of iPSCs of the present disclosure, which are ES-like cells. Using known methods to introduced desired genes/mutations into ES cells, iPSCs may be genetically engineered, and the resulting engineered cells differentiated into desired cell types, e.g., hematopoietic cells, neural cells, pancreatic cells, cartilage cells, etc. Genes which may be introduced into the iPSCs include, for example, epidermal growth factor, basic fibroblast growth factor, glial derived neurotrophic growth factor, insulin-like growth factor (I and II), neurotrophin3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, collagen, human serum albumin, etc.

In addition, it is also possible to use one of the negative selection systems now known in the art for eliminating therapeutic cells from a patient if necessary. For example, donor cells transfected with the thymidine kinase (TK) gene will lead to the production of embryonic cells containing the TK gene. Differentiation of these cells will lead to the isolation of therapeutic cells of interest which also express the TK gene. Such cells may be selectively eliminated at any time from a patient upon gancyclovir administration. Such a negative selection system is described in U.S. Pat. No. 5,698,446, and is herein incorporated by reference.

Examples of diseases, disorders, or conditions that may be treated or prevented include neurological, endocrine, structural, skeletal, vascular, urinary, digestive, integumentary, blood, immune, auto-immune, inflammatory, endocrine, kidney, bladder, cardiovascular, cancer, circulatory, digestive, hematopoietic, and muscular diseases, disorders, and conditions. In addition, reprogrammed cells may be used for reconstructive applications, such as for repairing or replacing tissues or organs.

With respect to the therapeutic methods of present disclosure, it is not intended that the administration of iPSCs to a mammal be limited to a particular mode of administration, dosage, or frequency of dosing; the present disclosure contemplates all modes of administration, including intramuscular, intravenous, intraarticular, intralesional, subcutaneous, or any other route sufficient to provide a dose adequate to prevent or treat a disease. The iPSCs may be administered to the mammal in a single dose or multiple doses. When multiple doses are administered, the doses may be separated from one another by, for example, one week, one month, one year, or ten years. One or more growth factors, hormones, interleukins, cytokines, or other cells may also be administered before, during, or after administration of the cells to further bias them towards a particular cell type.

The iPSCs of the present disclosure may be used as an in vitro model of differentiation, in particular for the study of genes which are involved in the regulation of early development. Differentiated cell tissues and organs using the iPSCs may be used in drug studies.

Furthermore, the iPSCs produced according to the disclosure maybe introduced into animals, e.g., SCID mice, cows, pigs, e.g., under the renal capsule or intramuscularly and used to produce a teratoma therein. This teratoma can be used to derive different tissue types. Also, the inner cell mass produced by X-species nuclear transfer may be introduced together with a biodegradable, biocompatible polymer matrix that provides for the formation of 3-dimensional tissues. After tissue formation, the polymer degrades, ideally just leaving the donor tissue, e.g., cardiac, pancreatic, neural, lung, liver. In some instances, it may be advantageous to include growth factors and proteins that promote angiogenesis. Alternatively, the formation of tissues can be effected totally in vitro, with appropriate culture media and conditions, growth factors, and biodegradable polymer matrices.

In certain more specific embodiments, provided herein are methods of treating a subject in need thereof comprising: (a) obtaining an isolated population of cells from a subject; (b) reprogramming γδ T cells in the isolated population of cells to produce iPSCs according to the method of producing iPSCs described herein; and (c) administering the produced iPSCs, or a pharmaceutical composition comprising the produced iPSCs to the subject, optionally after differentiating the iPSCs into one or more desired cell types.

In certain embodiments, the produced iPSCs are differentiated the iPSCs into one or more desired cell types and administered to the subject.

For example, in some embodiments, given their remarkable multi-lineage differentiation and self-renewal potential, iPSCs can differentiate into T cells to provide an almost unlimited source of rejuvenated T cells, addressing a significant issue that limits the efficacy of T cells against tumors, i.e., T cell exhaustion (Schietinger, A. & Greenberg, P. D., *Trends Immunol.*, 2015, 35(2):51-60). T cells exert effector functions by binding to antigens via T cell receptors (TCR). Nevertheless, sometimes TCR binding does not give rise to effector activity, especially under chronic infection conditions, resulting in T cell exhaustion (Karagiannis, P., et al., *Seminars in Immunology*, 2015, 28(1):35-44). In such situations, adoptive cellular therapy (ACT) can be utilized as a compensatory mechanism, which involves either ex vivo expansion of T cells isolated from patients' tumor microenvironment or genetic modification of autologous T cell receptors to elicit immune response (Id.). Rejuvenating exhausted T cells by reprogramming them into iPSCs represent a potent solution for T cell exhaustion, as the TCR rearrangements preserve gene loci of certain specific antigens (Id.).

In some embodiments, provided herein is a composition comprising an isolated population or subpopulation functionally enhanced derivative immune cells that have been differentiated from the iPSCs produced according the methods provided herein. In some embodiments, the iPSCs comprise one or more targeted genetic editing which are retainable in the iPSC-derived immune cells, wherein the genetically engineered iPSCs and derivative cells thereof are suitable for cell based adoptive therapies. In one embodiment, the isolated population or subpopulation of genetically engineered immune cell comprises iPSC derived pro-T or T cells. In one embodiment, the isolated population or subpopulation of genetically engineered immune cell comprises iPSC derived pro-NK or NK cells. In one embodiment, the isolated population or subpopulation of genetically engineered immune cell comprises iPSC derived immune regulatory cells or myeloid derived suppressor cells (MDSCs). In some embodiments, the iPSC derived genetically engineered immune cells are further modulated ex vivo for improved therapeutic potential.

In certain embodiments, the produced iPSCs are administered to the subject without further differentiation.

In certain embodiments, the subject is a human.

In certain embodiments, the subject has a hyperproliferative disorder or a cancer of hematopoietic system. In some embodiments, the subject has a solid tumor. In some embodiments, the hyperproliferative disorder of the hematopoietic system is polycythemia vera, essential thrombocythemia, myelofibrosis with myeloid metaplasia, or chronic myelogenous leukemia.

In certain embodiments, the produced iPSCs or pharmaceutical compositions comprising the produced iPSCs described herein can be used to treat cancers. Cancers that can be treated include tumors that are not vascularized, or not yet substantially vascularized, as well as vascularized tumors. In some embodiments, the cancers can be non-solid tumors (such as hematological tumors, for example, leukemias and lymphomas) or can be solid tumors. In some embodiments, the types of cancers include, but are not limited to, carcinoma, blastoma, and sarcoma, and certain leukemia or lymphoid malignancies, benign and malignant tumors, and malignancies e.g., sarcomas, carcinomas, and melanomas. In some embodiments, adult tumors/cancers and pediatric tumors/cancers are also included.

In some embodiments, the produced iPSCs or pharmaceutical compositions comprising the produced iPSCs described herein are used to treat hematologic cancers. Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, chronic myeloic leukemia, and chronic lymphocytic leukemia), juvenile myelomonocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, agnogenic myeloid metaplasia, familial erythrophagocytic lymphohistiocytosis, hairy cell leukemia and myelodysplasia.

In some embodiments, the subject has myeloma, non-Hodgkin's lymphoma, Hodgkin's lymphoma, chronic myeloid leukemia, chronic myelogenous leukemia, chronic granulocytic leukemia, acute lymphoblastic leukemia, acute nonlymphoblastic leukemia, or pre-leukemia.

In some embodiments, the produced iPSCs or pharmaceutical compositions comprising the produced iPSCs described herein are used to treat solid tumors. Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, meduloblastoma, Schwannoma craniopharyogioma, ependymoma, pineaioma, hemangioblastoma, acoustic neuroma, oligodendroglioma, menangioma, neuroblastoma, retinoblastoma and brain metastases).

In some embodiments, the subject has breast cancer, ovarian cancer, brain cancer, prostate cancer, lung cancer, colon cancer, skin cancer, liver cancer, pancreatic cancer, sarcoma, or chronic granulomatous disease.

In some embodiments, provided herein is a combination therapy comprising the cells such iPSCs provided herein and one or more additional agents.

Also provided are the iPSCs described herein or pharmaceutical compositions comprising the iPSCs described herein for use in therapy. Also provided are the iPSCs described herein or pharmaceutical compositions comprising the iPSCs described herein for use in a method of treating a hyperproliferative disorder or a cancer of hematopoietic system in a subject in need of such treatment.

5.7. Methods for Identifying an Agent that Reprograms or Contributes to Reprogramming Somatic Cells In another aspect, provided herein are methods for identifying an agent that, alone or in combination with one or more other agents, reprograms somatic cells (e.g., T cells) to a less differentiated state. The present disclosure further provides agents identified according to the methods provided herein.

In one embodiment, the methods comprise contacting somatic cells with an activation culture comprising IL-15, zoledronic acid, and/or IL-2; contacting the somatic cells with a candidate agent and then determining whether the presence of the candidate agent results in enhanced reprogramming (e.g., increased reprogramming speed and/or efficiency) relative to that which would occur if cells had not been contacted with the candidate agent.

In some embodiments, provided herein are methods for identifying an agent that, alone or in combination with one or more other agents, reprograms somatic cells (e.g., T cells) to a less differentiated state, comprising (a) contacting an isolated population of cells with an activation culture; wherein the activation culture comprises IL-15 and zoledronic acid; (b) culturing the isolated population of cells in the activation culture to enrich and/or activate γδ T cells in the isolated population of cells; (c) contacting an isolated population of cells with a candidate agent; (d) transducing the γδ T cells with one or more viral vector(s) encoding one or more reprogramming factors; (e) culturing the transduced γδ T cells under conditions suitable for reprogramming mammalian somatic cells to a less differentiated state, and (f) determining if at least some of the somatic cells are reprogrammed to a less differentiated state. In some embodiments, the less differentiated state is a multipotent state. In some embodiments, the less differentiated state is a pluripotent state. In certain embodiments, the activation culture further comprises one or more additional agents or compounds, for example, to improve the efficiency of activation or induction. In one embodiment, the activation culture further comprises Interleukin-2 (IL-2).

In some embodiments. the IL-15, zoledronic acid, and/or IL-2 and the candidate agent are present together in the cell culture medium, while in other embodiments the IL-15, zoledronic acid, and/or IL-2 and the candidate agent are not present together (e.g., the cells are exposed to the agents sequentially). In certain embodiments, the cells are maintained in culture for 1-20 days. In certain embodiments, the cells are maintained in culture for 1-17 days. In certain embodiments, the cells are maintained in culture for 1-15 days. In certain embodiments, the cells are maintained in culture for 1-13 days. In certain embodiments, the cells are maintained in culture for 1-11 days. In certain embodiments, the cells are maintained in culture for 1-9 days. In certain embodiments, the cells are maintained in culture for 1-7 days. In certain embodiments, the cells are maintained in culture for 1-5 days. In certain embodiments, the cells are maintained in culture for 1-3 days. In certain embodiments, the cells are maintained in culture for 12-72 hours. In certain embodiments, the cells are maintained in culture for 12-60 hours. In certain embodiments, the cells are maintained in culture for 12-48 hours. In certain embodiments, the cells are maintained in culture for 12-36 hours. In certain embodiments, the cells are maintained in culture for 12-24 hours. In certain embodiments, the cells are maintained in culture for 8-16 hours. In certain embodiments, the cells are maintained in culture for 4-8 hours. In certain embodiments, the cells are maintained in culture for 2-4 hours. The cells may be maintained in culture for, e.g., at most 13 days, at most 10 days, at most 9 days, at most 8 days, at most 7 days, at most 6 days, at most 5 days, at most 4 days, at most 3 days, at most 2 days, or at most 1 day, etc., during which time they are contacted with the IL-15, zoledronic acid, and/or IL-2 and the candidate agent for all or part of the time. In some embodiments, the agent is identified as an agent that reprograms cells if there are at least 2, 5, or 10 times as many reprogrammed cells or colonies comprising predominantly reprogrammed cells after said time period than if the cells have not been contacted with the agent.

A candidate agent can be any molecule or supramolecular complex, e.g. peptide, small organic or inorganic molecule, polysaccharide, polynucleotide, etc. which is to be tested for ability to reprogram or facilitate or enhance reprogramming cells. Candidate agents may be obtained from a wide variety of sources, as will be appreciated by those in the art, including libraries of synthetic or natural compounds. In some embodiments, candidate agents are synthetic compounds. Numerous techniques are available for the random and directed synthesis of a wide variety of organic compounds and biomolecules. In some embodiments, the candidate modulators are provided as mixtures of natural compounds in the form of bacterial, fungal, plant and animal extracts, fermentation broths, conditioned media, etc., that are available or readily produced.

In some embodiments, a library of compounds is screened. A library is typically a collection of compounds that can be presented or displayed such that the compounds can be identified in a screening assay. In some embodiments, compounds in the library are housed in individual wells (e.g., of microtiter plates), vessels, tubes, etc., to facilitate convenient transfer to individual wells or vessels for contacting cells, performing cell-free assays, etc. The library may be composed of molecules having common structural features which differ in the number or type of group attached to the main structure or may be completely random. Libraries include but are not limited to, for example, phage display libraries, peptide libraries, polysome libraries, aptamer libraries, synthetic small molecule libraries, natural compound libraries, and chemical libraries. Methods for preparing libraries of molecules are well known in the art and many libraries are available from commercial or non-commercial sources. Libraries of interest include synthetic organic combinatorial libraries. Libraries, such as, synthetic small molecule libraries and chemical libraries can comprise a structurally diverse collection of chemical molecules. Small molecules include organic molecules often having multiple carbon-carbon bonds. The libraries can comprise cyclic carbon or heterocyclic structure and/or aromatic or polyaromatic structures substituted with one or more functional groups. In some embodiments, the small molecule has between 5 and 50 carbon atoms, e.g., between 7 and 30 carbons. In some embodiments, the compounds are macrocyclic. Libraries of interest also include peptide libraries, randomized oligonucleotide libraries, and the like. Libraries can be synthesized of peptoids and non-peptide synthetic moieties. Such libraries can further be synthesized which contain non-peptide synthetic moieties which are less subject to enzymatic degradation compared to their naturally-occurring counterparts. Small molecule combinatorial libraries may also be generated. A combinatorial library of small organic compounds may comprise a collection of closely related analogs that differ from each other in one or more points of diversity and are synthesized by organic techniques using multi-step processes. Combinatorial libraries can include a vast number of small organic compounds. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. In some embodiments, mixtures containing two or more compounds, extracts or other preparations obtained from natural sources (which may comprise dozens of compounds or more), and/or inorganic compounds, etc., are screened.

In one embodiment, the methods of the invention are used to screen "approved drugs." An "approved drug" is any compound (which term includes biological molecules such as proteins and nucleic acids) which has been approved for use in humans by the FDA or a similar government agency in another country, for any purpose. This can be a particularly useful class of compounds to screen because it represents a set of compounds which are believed to be safe and, at least in the case of FDA approved drugs, therapeutic for at least one purpose. Thus, there is a high likelihood that these drugs will at least be safe for other purposes.

Representative examples of libraries that could be screened include DIVERSet™ available from ChemBridge Corporation, 16981 Via Tazon, San Diego, Calif. 92127. DIVERSet contains between 10,000 and 50,000 drug-like, hand-synthesized small molecules. The compounds are preselected to form a "universal" library that covers the maximum pharmacophore diversity with the minimum number of compounds and is suitable for either high throughput or lower throughput screening. For descriptions of additional libraries, see, for example, Tan, et al., *Am. Chem Soc.* 120, 8565-8566, 1998; Floyd C D, Leblanc C, Whittaker M, *Prog Med Chem* 36:91-168, 1999. Numerous libraries are commercially available, e.g., from AnalytiCon USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. For example, libraries based on quinic acid and shikimic acid, hydroxyproline, santonine, dianhydro-D-glucitol, hydroxypipecolinic acid, andrographolide, piperazine-2-carboxylic acid based library, cytosine, etc., are commercially available.

In some embodiments, the candidate agents are cDNAs from a cDNA expression library prepared from cells, e.g., pluripotent cells. Such cells may be embryonic stem cells, oocytes, blastomeres, teratocarcinomas, embryonic germ cells, inner cell mass cells, etc.

It will be appreciated that the candidate reprogramming agent to be tested is typically one that is not present in standard culture medium, or if present is present in lower amounts than when used in the present invention. It will also be appreciated that a useful reprogramming agent or other form of reprogramming treatment need not be capable of reprogramming all types of somatic cells and need not be capable of reprogramming all somatic cells of a given cell type. Without limitation, a candidate agent that results in a population that is enriched for reprogrammed cells by a factor of 2, 5, 10, 50, 100 or more (i.e., the fraction of reprogrammed cells in the population is 2, 5, 10, 50, or 100 times more than present in a starting population of cells treated in the same way but without being contacted with the candidate agent) is of use.

In some embodiments, the screening method provided herein is used to identify an agent or combination of agents that substitutes for Klf4 in reprogramming cells to a pluripotent state. In some embodiments, the method is used to identify an agent that substitutes for Sox2 in reprogramming cells to a pluripotent state. In some embodiments, the method is used to identify an agent that substitutes for Oct3/4 in reprogramming cells to a pluripotent state. In some embodiments, the method is used to identify an agent that substitutes for c-Myc in reprogramming cells to a pluripotent state. In some embodiments, the method is used to identify an agent that substitutes for Lin28 in reprogramming cells to a pluripotent state. In some embodiments, the methods are practiced using human cells. In some embodiments, the methods are practiced using mouse cells. In some embodiments, the methods are practiced using non-human primate cells.

In another aspect, provided herein are methods for identifying a gene that activates the expression of an endogenous pluripotency gene in somatic cells (e.g., T cells).

In some embodiments, the method comprises (a) contacting an isolated population of cells with an activation culture; wherein the activation culture comprises IL-15 and zoledronic acid; (b) culturing the isolated population of cells in the activation culture to enrich and/or activate γδ T cells in the isolated population of cells; (c) transducing the γδ T cells with one or more viral vector(s) encoding one or more candidate reprogramming factors; (d) culturing the transduced γδ T cells under conditions suitable for reprogramming mammalian somatic cells to a less differentiated state, and (e) determining if at least some of the somatic cells are reprogrammed to a less differentiated state. In some embodiments, the less differentiated state is a multipotent state. In some embodiments, the less differentiated state is a pluripotent state.

In some more specific embodiments, the method comprises (a) contacting an isolated population of cells with an activation culture; wherein the activation culture comprises IL-15 and zoledronic acid; (b) culturing the isolated population of cells in the activation culture to enrich and/or activate γδ T cells in the isolated population of cells; (c) transducing the γδ T cells with one or more viral vector(s) encoding one or more candidate reprogramming factors; and (d) culturing the transduced γδ T cells under conditions suitable for reprogramming mammalian somatic cells to a pluripotent state, and (e) determining if at least some of the somatic cells are reprogrammed to a pluripotent state.

In certain embodiments, the activation culture further comprises one or more additional agents or compounds, for example, to improve the efficiency of activation or induction. In one embodiment, the activation culture further comprises Interleukin-2 (IL-2).

Therefore, in some embodiments, the method provided herein comprises (a) contacting an isolated population of cells with an activation culture; wherein the activation culture comprises IL-15, zoledronic acid and IL-2; (b)

culturing the isolated population of cells in the activation culture to enrich and/or activate γδ T cells in the isolated population of cells; (c) transducing the γδ T cells with one or more viral vector(s) encoding one or more candidate reprogramming factors; (d) culturing the transduced γδ T cells under conditions suitable for reprogramming mammalian somatic cells to a less differentiated state; and (e) determining if at least some of the somatic cells are reprogrammed to a less differentiated state.

In some more specific embodiments, the method provided herein comprises: (a) contacting an isolated population of cells with an activation culture; wherein the activation culture comprises IL-15, zoledronic acid and IL-2; (b) culturing the isolated population of cells in the activation culture to enrich and/or activate γδ T cells in the isolated population of cells; (c) transducing the γδ T cells with one or more viral vector(s) encoding one or more candidate reprogramming factors; (d) culturing the transduced γδ T cells under conditions suitable for reprogramming mammalian somatic cells to a pluripotent state; and (e) determining if at least some of the somatic cells are reprogrammed to a pluripotent state.

In other embodiments, the methods comprise culturing the somatic cells as provided herein, e.g., in the presence of IL-15, zoledronic acid, and/or IL-2, and then transfecting the somatic cells of the present disclosure with a cDNA library prepared from ES cells or oocytes, selecting for cells that express the first selectable marker, and assessing the expression of the first endogenous pluripotency gene in the transfected cells that express the first selectable marker. The expression of the first endogenous pluripotency gene indicates that the cDNA encodes a gene that activates the expression of an endogenous pluripotency gene in somatic cells.

The present methods are applicable for identifying a gene that activates the expression of at least two endogenous pluripotency genes in somatic cells. The somatic cells used in the methods further comprise a second endogenous pluripotency gene linked to a second selectable marker. The methods can be modified to select for transfected cells that express both selectable markers, among which the expression of the first and the second endogenous pluripotency genes are assessed. The expression of both the first and the second endogenous pluripotency genes indicates that the cDNA encodes a gene that activates the expression of at least two pluripotency genes in somatic cells.

The present methods are further applicable for identifying a gene that activates the expression of at least three endogenous pluripotency genes in somatic cells. The somatic cells used in the methods further comprise a third endogenous pluripotency gene linked to a third selectable marker. The methods are modified to select for transfected cells that express all three selectable markers, among which the expression of all three endogenous pluripotency genes are assessed. The expression of all three endogenous pluripotency genes indicates that the cDNA encodes a gene that activates the expression of at least three pluripotency genes in somatic cells.

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999; Manipulating the Mouse Embryos, A Laboratory Manual, 3$^{rd}$ Ed., by Hogan et al., Cold Spring Harbor Laboratory Press, Cold Spring Harbor, N.Y., 2003; Gene Targeting: A Practical Approach, IRL Press at Oxford University Press, Oxford, 1993; and Gene Targeting Protocols, Human Press, Totowa, N.J., 2000. All patents, patent applications and references cited herein are incorporated in their entirety by reference.

6. EMBODIMENTS

This invention provides the following non-limiting embodiments.

In one set of embodiments (embodiment set A), provided are:

A1. A method of producing induced pluripotent stem cells (iPSCs) comprising:
  (a) contacting an isolated population of cells with an activation culture; wherein the activation culture comprises IL-15 and zoledronic acid;
  (b) culturing the isolated population of cells in the activation culture to enrich and/or activate γδ T cells in the isolated population of cells;
  (c) transducing the γδ T cells with a viral vector encoding one or more reprogramming factors; and
  (d) culturing the transduced γδ T cells under conditions suitable for reprogramming mammalian somatic cells to a pluripotent state.

A2. The method of embodiment A1, wherein the activation culture further comprises IL-2.

A3. The method of embodiment A1 or A2, wherein the viral vector is a Sendai virus (SeV) vector.

A4. The method of any one of embodiments A1-A3, wherein the method further comprises obtaining the isolated population of cells from a subject.

A5. The method of any one of embodiments A1-A4, wherein the isolated population of cells are peripheral blood mononuclear cells (PBMCs).

A6. The method of any one of embodiments A1-A5, wherein the isolated population of cells are terminally differentiated cells.

A7. The method of any one of embodiments A1-A6, wherein the isolated population of cells are mammal cells.

A8. The method of any one of embodiments A7, wherein the isolated population of cells are human cells.

A9. The method of any one of embodiments A1-A8, wherein the isolated population of cells are cultured in the activation culture for 1-20 days, for 1-17 days, for 1-15 days, for 1-13 days, for 1-11 days, for 1-9 days, for 1-7 days, for 1-5 days, for 1-3 days, for 12-72 hours, for 12-60 hours, for 12-48 hours, for 12-36 hours, for 12-24 hours, for 8-16 hours, for 4-8 hours, or for 2-4 hours.

A10. The method of embodiment A9, wherein the isolated population of cells are cultured in the activation culture for at most 13 days, at most 10 days, at most 9 days, at most 8 days, at most 7 days, at most 6 days, at most 5 days, at most 4 days, at most 3 days, at most 2 days, or at most 1 day.

A11. The method of embodiment A10, wherein the isolated population of cells are cultured in the activation culture for at most 3 days.

A12. The method of embodiment A10, wherein the isolated population of cells are cultured in the activation culture for 3 days.

A13. The method of any one of embodiments A1-A12, wherein after being cultured in the activation culture the isolated population of cells comprise 5%-100% γδ T cells, 5%-95% γδ T cells, 5%-90% γδ T cells, 5%-85% γδ T cells, 5%-80% γδ T cells, 5%-75% γδ T cells, 5%-70% γδ T cells, 5%-65% γδ T cells, 5%-60% γδ T cells, 5%-55% γδ T cells, 5%-50% γδ T cells, 5%-45% γδ T cells, 5%-40% γδ T cells, 5%-35% γδ T cells, 5%-30% γδ T cells, 5%-25% γδ T cells, 5%-20% γδ T cells, or 5%-15% γδ T cells.

A14. The method of embodiment A13, wherein after being cultured in the activation culture the isolated population of cells comprise less than 90%, less than 80%, less than 70%, less than 60%, less than 50%, less than 45%, less than 40%, less than 35%, or less than 30% γδ T cells.

A15. The method of embodiment A14, wherein after being cultured in the activation culture the isolated population of cells comprise less than 35% γδ T cells.

A16. The method of any one of embodiments A1-A15, further comprises enriching the γδ T cells in the isolated population of cells after step (b).

A17. The method of embodiment A16, wherein the γδ T cells are enriched by cell-cell clump enrichment.

A18. The method of any one of embodiments A1-A17, wherein at least part of the γδ T cells are activated to Vγ9$^+$ γδ T cells in step (b).

A19. The method of any one of embodiments A1-A17, wherein at least part of the γδ T cells are activated to Vγ9δ2$^+$ γδ T cells in step (b).

A20. The method of any one of embodiments A1-A19, wherein the one or more reprogramming factors are selected from a group consisting of OCT3/4, SOX2, KLF4, LIN28, and c-Myc.

A21. The method of any one of embodiments A1-A20, wherein in step (d) the transduced γδ T cells are cultured in the presence of one or more feeder layers.

A22. The method of embodiment A21, wherein in step (d) the transduced γδ T cells are cultured in the presence of a mono layer of feeder layer.

A23. The method of embodiment A21 or A22, wherein the feeder layer comprises mouse embryonic fibroblasts (MEFs).

A24. The method of any one of embodiments A1-A23, further comprising isolating and/or purifying the produced iPSCs.

A25. The method of embodiments A24, further comprising administering the isolated iPSCs to a subject.

A26. The method of any one of embodiments A1-A24, further comprising differentiating the iPSCs ex vivo to cells of a desired cell type.

A27. The method of embodiment A26, further comprising administering the differentiated cell to a subject.

A28. The method of any one of embodiments A1-A27, wherein the produced iPSCs are negative for a Sendai virus (SeV) vector.

A29. The method of any one of embodiments A1-A28, wherein the produced iPSCs are derived from γδ T cells.

A30. The method of any one of embodiments A1-A28, wherein the produced iPSCs have rearrangement genes of TRG and TRD gene loci; and wherein optionally the produced iPSCs have Vγ9 and Vδ2 gene arrangements.

A31. The method of any one of embodiments A1-A28, wherein the produced iPSCs are not derived from αβ T cells.

A32. The method of any one of embodiments A1-A28, wherein the produced iPSCs do not produce polymerase chain reaction (PCR) products from TCRA and TCRB gene loci.

A33. The method of any one of embodiments A1-A32, wherein the produced iPSCs are genomically stable with no loss of a chromosome.

A34. The method of embodiment A33, wherein the genomic stability of the produced iPSCs is determined by Karyotyping analysis.

A35. The method of any one of embodiments A1-A34, wherein the produced iPSCs can grow in feeder free medium after adoption.

A36. An induced pluripotent stem cell (iPSC) produced according to the method of any one of embodiments A1-A35.

A37. A pharmaceutical composition comprising the iPSC of embodiment A36 and a pharmaceutically acceptable excipient.

A38. A differentiated cell produced according to the method of embodiment A26.

A39. A pharmaceutical composition comprising the differentiated cell of embodiment A38 and a pharmaceutically acceptable excipient.

In another set of embodiments (embodiment set B), provided are:

B1. A method of treating a subject in need thereof comprising:
(i) obtaining a population of cells comprising peripheral blood mononuclear cells (PBMCs) from a subject;
(ii) reprogramming γδ T cells in the population of cells to produced iPSCs; and
(iii) administering the produced iPSCs, or a pharmaceutical composition comprising the produced iPSCs to the subject, optionally after differentiating the iPSCs into one or more desired types of cells,
wherein step (ii) comprises:
(a) contacting the population of cells with an activation culture; wherein the activation culture comprises IL-15 and zoledronic acid;
(b) culturing the population of cells in the activation culture to enrich and/or activate γδ T cells in the population of cells;
(c) transducing the γδ T cells with a viral vector encoding one or more reprogramming factors; and
(d) culturing the transduced γδ T cells under conditions suitable for reprogramming mammalian somatic cells to a pluripotent state.

B2. The method of embodiment B1, wherein the activation culture further comprises IL-2.

B3. The method of embodiment B1 or B2, wherein the viral vector is a Sendai virus (SeV) vector.

B4. The method of any one of embodiments B1-B3, wherein the population of cells are cultured in the activation culture for 1-20 days, for 1-17 days, for 1-15 days, for 1-13 days, for 1-11 days, for 1-9 days, for 1-7 days, for 1-5 days, for 1-3 days, for 12-72 hours, for 12-60 hours, for 12-48 hours, for 12-36 hours, for 12-24 hours, for 8-16 hours, for 4-8 hours, or for 2-4 hours.

B5. The method of embodiment B4, wherein the population of cells are cultured in the activation culture for at most 13 days, at most 10 days, at most 9 days, at most 8 days, at most 7 days, at most 6 days, at most 5 days, at most 4 days, at most 3 days, at most 2 days, or at most 1 day.

B6. The method of embodiment B5, wherein the population of cells are cultured in the activation culture for at most 3 days.
B7. The method of embodiment B5, wherein the population of cells are cultured in the activation culture for 3 days.
B8. The method of any one of embodiments B1-B7, wherein after being cultured in the activation culture the population of cells comprise 5%-100% γδ T cells, 5%-95% γδ T cells, 5%-90% γδ T cells, 5%-85% γδ T cells, 5%-80% γδ T cells, 5%-75% γδ T cells, 5%-70% γδ T cells, 5%-65% γδ T cells, 5%-60% γδ T cells, 5%-55% γδ T cells, 5%-50% γδ T cells, 5%-45% γδ T cells, 5%-40% γδ T cells, 5%-35% γδ T cells, 5%-30% γδ T cells, 5%-25% γδ T cells, 5%-20% γδ T cells, or 5%-15% γδ T cells.
B9. The method of embodiment B8, wherein after being cultured in the activation culture the population of cells comprise less than 90%, less than 80%, less than 70%, less than 60%, less than 50%, less than 45%, less than 40%, less than 35%, or less than 30% γδ T cells.
B10. The method of embodiment B9, wherein after being cultured in the activation culture the population of cells comprise less than 35% γδ T cells.
B11. The method of any one of embodiments B1-B10, further comprises enriching the γδ T cells in the population of cells after step (b).
B12. The method of embodiment B11, wherein the γδ T cells are enriched by cell-cell clump enrichment.
B13. The method of any one of embodiments B1-B12, wherein at least part of the γδ T cells are activated to Vγ9+ γδ T cells in step (b).
B14. The method of any one of embodiments B1-B12, wherein at least part of the γδ T cells are activated to Vγ9δ2+ γδ T cells in step (b).
B15. The method of any one of embodiments B1-B14, wherein the one or more reprogramming factors are selected from a group consisting of OCT3/4, SOX2, KLF4, LIN28, and c-Myc.
B16. The method of any one of embodiments B1-B15, wherein in step (d) the transduced γδ T cells are cultured in the presence of one or more feeder layers.
B17. The method of embodiment B16, wherein in step (d) the transduced γδ T cells are cultured in the presence of a mono layer of feeder layer.
B18. The method of embodiment B16 or B17, wherein the feeder layer comprises mouse embryonic fibroblasts (MEFs).
B19. The method of any one of embodiments B1-B18, further comprising isolating and/or purifying the produced iPSCs.
B20. The method of any one of embodiments B1-B19, further comprising differentiating the iPSCs ex vivo to cells of a desired cell type.
B21. The method of any one of embodiments B 1-B20, wherein the produced iPSCs are negative for a Sendai virus (SeV) vector.
B22. The method of any one of embodiments B1-B20, wherein the produced iPSCs are derived from γδ T cells.
B23. The method of any one of embodiments B1-B20, wherein the produced iPSCs have rearrangement genes of TRG and TRD gene loci; and wherein optionally the produced iPSCs have Vγ9 and Vδ2 gene arrangements.
B24. The method of any one of embodiments B1-B20, wherein the produced iPSCs are not derived from αβ T cells.
B25. The method of any one of embodiments B1-B20, wherein the produced iPSCs do not produce polymerase chain reaction (PCR) products from TCRA and TCRB gene loci.
B26. The method of any one of embodiments B1-B25, wherein the produced iPSCs are genomically stable with no loss of a chromosome.
B27. The method of embodiment B26, wherein the genomic stability of the produced iPSCs is determined by Karyotyping analysis.
B28. The method of any one of embodiments B1-B27, wherein the produced iPSCs can grow in feeder free medium after adoption.
B29. The method of any one of embodiments B1-B28, wherein the subject is a human.
B30. The method of any one of embodiments B1-B29, wherein the subject has a hyperproliferative disorder or a cancer of hematopoietic system.

In another set of embodiments (embodiment set C), provided are:
C1. An isolated population of induced pluripotent stem cells (iPSCs), wherein the isolated population of iPSCs comprise pluripotent cells, wherein the pluripotent cells express one or more reprogramming factors, and/or wherein the pluripotent cells comprise a nucleotide sequence encoding rearrangement of TRG and TRD genes.
C2. The isolated population of iPSCs of embodiment C1, wherein the reprogramming factors are selected from a group consisting of Oct3/4, Sox2, Klf4, c-Myc, and Lin28.
C3. The isolated population of iPSCs of embodiment C1 or C2, wherein the isolated population of iPSCs are negative for a Sendai virus (SeV) vector.
C4. The isolated population of iPSCs of any one of embodiments C1-C3, wherein the isolated population of iPSCs are derived from γδ T cells.
C5. The isolated population of iPSCs of any one of embodiments C1-C3, wherein the isolated population of iPSCs have rearrangement genes of TRG and TRD gene loci; and wherein optionally the isolated population of iPSCs have Vγ9 and Vδ2 gene arrangements.
C6. The isolated population of iPSCs of any one of embodiments C1-C3, wherein the isolated population of iPSCs are not derived from αβ T cells.
C7. The isolated population of iPSCs of any one of embodiments C1-C3, wherein the isolated population of iPSCs do not produce PCR products from TCRA and TCRB gene loci.
C8. The isolated population of iPSCs of any one of embodiments C1-C7, wherein the isolated population of iPSCs are genomically stable with no loss of a chromosome.
C9. The isolated population of iPSCs of embodiment C8, wherein the genomic stability of the isolated population of iPSCs is determined by Karyotyping analysis.
C10. The isolated population of iPSCs of any one of embodiments C1-C9, wherein the isolated population of iPSCs can grow and maintain in feeder free medium after adoption.

In yet another set of embodiments (embodiment set D), provided are:
D1. A method of producing induced pluripotent stem cells (iPSCs) comprising:
(a) a step for performing a function of enriching and/or activating γδ T cells in the isolated population of cells; and (b) a step for performing a function of reprogramming the γδ T cells to a pluripotent state.

D2. The method of embodiment D1, wherein the step for performing a function of enriching and/or activating γδ T cells in the isolated population of cells comprises contacting the isolated population of cells with an activation culture; wherein the activation culture comprises IL-15 and zoledronic acid; and culturing the isolated population of cells in the activation culture to enrich and/or activate γδ T cells in the isolated population of cells.

D3. The method of embodiment D2, wherein the activation culture further comprises IL-2.

D4. The method of any one of embodiments D1-D3, wherein the method further comprises a step for performing a function of obtaining the isolated population of cells from a subject.

D5. The method of any one of embodiments D1-D4, wherein the isolated population of cells are peripheral blood mononuclear cells (PBMCs).

D6. The method of any one of embodiments D1-D5, wherein the isolated population of cells are terminally differentiated cells.

D7. The method of any one of embodiments D1-D6, wherein the isolated population of cells are mammal cells.

D8. The method of embodiment D7, wherein the isolated population of cells are human cells.

D9. The method of any one of embodiments D2-D8, wherein the isolated population of cells are cultured in the activation culture for 1-20 days, for 1-17 days, for 1-15 days, for 1-13 days, for 1-11 days, for 1-9 days, for 1-7 days, for 1-5 days, for 1-3 days, for 12-72 hours, for 12-60 hours, for 12-48 hours, for 12-36 hours, for 12-24 hours, for 8-16 hours, for 4-8 hours, or for 2-4 hours.

D10. The method of embodiment D9, wherein the isolated population of cells are cultured in the activation culture for at most 13 days, at most 10 days, at most 9 days, at most 8 days, at most 7 days, at most 6 days, at most 5 days, at most 4 days, at most 3 days, at most 2 days, or at most 1 day.

D11. The method of embodiment D10, wherein the isolated population of cells are cultured in the activation culture for at most 3 days.

D12. The method of embodiment D10, wherein the isolated population of cells are cultured in the activation culture for 3 days.

D13. The method of any one of embodiments D2-D12, wherein after being cultured in the activation culture the isolated population of cells comprise 5%-100% γδ T cells, 5%-95% γδ T cells, 5%-90% γδ T cells, 5%-85% γδ T cells, 5%-80% γδ T cells, 5%-75% γδ T cells, 5%-70% γδ T cells, 5%-65% γδ T cells, 5%-60% γδ T cells, 5%-55% γδ T cells, 5%-50% γδ T cells, 5%-45% γδ T cells, 5%-40% γδ T cells, 5%-35% γδ T cells, 5%-30% γδ T cells, 5%-25% γδ T cells, 5%-20% γδ T cells, or 5%-15% γδ T cells.

D14. The method of embodiment D13, wherein after being cultured in the activation culture the isolated population of cells comprise less than 90%, less than 80%, less than 70%, less than 60%, less than 50%, less than 45%, less than 40%, less than 35%, or less than 30% γδ T cells.

D15. The method of embodiment D14, wherein after being cultured in the activation culture the isolated population of cells comprise less than 35% γδ T cells.

D16. The method of any one of embodiments D1-D15, wherein at least part of the γδ T cells are activated to Vγ9$^+$ γδ T cells.

D17. The method of any one of embodiments D1-D15, wherein at least part of the γδ T cells are activated to Vγ9δ2$^+$ γδ T cells.

D18. The method of any one of embodiments D1-D17, wherein the step for performing a function of reprogramming the γδ T cells to a pluripotent state comprises transducing the γδ T cells with a viral vector encoding one or more reprogramming factors; and culturing the transduced γδ T cells under conditions suitable for reprogramming mammalian somatic cells to a pluripotent state.

D19. The method of embodiment D18, wherein the viral vector is a Sendai virus (SeV) vector.

D20. The method of embodiment D18 or D19, wherein the one or more reprogramming factors are selected from a group consisting of OCT3/4, SOX2, KLF4, LIN28, and c-Myc.

D21. The method of any one of embodiments D18-D20, wherein the transduced γδ T cells are cultured in the presence of one or more feeder layers.

D22. The method of embodiment D21, wherein the transduced γδ T cells are cultured in the presence of a mono layer of feeder layer.

D23. The method of embodiment D21 or D22, wherein the feeder layer comprises mouse embryonic fibroblasts (MEFs).

In yet another set of embodiments (embodiment set E), provided are:

E1. An induced pluripotent stem cell (iPSC) produced according to a method comprising:

(a) a step for performing a function of enriching and/or activating γδ T cells in the isolated population of cells; and (b) a step for performing a function of reprogramming the γδ T cells to a pluripotent state.

E2. The iPSC of embodiment E1, wherein the step for performing a function of enriching and/or activating γδ T cells in the isolated population of cells comprises contacting the isolated population of cells with an activation culture; wherein the activation culture comprises IL-15 and zoledronic acid; and culturing the isolated population of cells in the activation culture to enrich and/or activate γδ T cells in the isolated population of cells.

E3. The iPSC of embodiment E2, wherein the activation culture further comprises IL-2.

E4. The iPSC of any one of embodiments E1-E3, wherein the method further comprises a step for performing a function of obtaining the isolated population of cells from a subject.

E5. The iPSC of any one of embodiments E1-E4, wherein the isolated population of cells are peripheral blood mononuclear cells (PBMCs).

E6. The iPSC of any one of embodiment E1-E5, wherein the isolated population of cells are terminally differentiated cells.

E7. The iPSC of any one of embodiment E1-E6, wherein the isolated population of cells are mammal cells.

E8. The iPSC of any one of embodiment E7, wherein the isolated population of cells are human cells.

E9. The iPSC of any one of embodiments E2-E8, wherein the isolated population of cells are cultured in the activation culture for 1-20 days, for 1-17 days, for 1-15 days, for 1-13 days, for 1-11 days, for 1-9 days, for 1-7 days, for 1-5 days, for 1-3 days, for 12-72 hours, for 12-60 hours, for 12-48 hours, for 12-36 hours, for 12-24 hours, for 8-16 hours, for 4-8 hours, or for 2-4 hours.

E10. The iPSC of embodiment E9, wherein the isolated population of cells are cultured in the activation culture for at most 13 days, at most 10 days, at most 9 days, at most 8 days, at most 7 days, at most 6 days, at most 5 days, at most 4 days, at most 3 days, at most 2 days, or at most 1 day.

E11. The iPSC of embodiment E10, wherein the isolated population of cells are cultured in the activation culture for at most 3 days.

E12. The iPSC of embodiment E10, wherein the isolated population of cells are cultured in the activation culture for 3 days.

E13. The iPSC of any one of embodiments E2-E12, wherein after being cultured in the activation culture the isolated population of cells comprise 5%-100% γδ T cells, 5%-95% γδ T cells, 5%-90% γδ T cells, 5%-85% γδ T cells, 5%-80% γδ T cells, 5%-75% γδ T cells, 5%-70% γδ T cells, 5%-65% γδ T cells, 5%-60% γδ T cells, 5%-55% γδ T cells, 5%-50% γδ T cells, 5%-45% γδ T cells, 5%-40% γδ T cells, 5%-35% γδ T cells, 5%-30% γδ T cells, 5%-25% γδ T cells, 5%-20% γδ T cells, or 5%-15% γδ T cells.

E14. The iPSC of embodiment E13, wherein after being cultured in the activation culture the isolated population of cells comprise less than 90%, less than 80%, less than 70%, less than 60%, less than 50%, less than 45%, less than 40%, less than 35%, or less than 30% γδ T cells.

E15. The iPSC of embodiment E14, wherein after being cultured in the activation culture the isolated population of cells comprise less than 35% γδ T cells.

E16. The iPSC of any one of embodiments E1-E15, wherein at least part of the γδ T cells are activated to Vγ9+ γδ T cells.

E17. The iPSC of any one of embodiments E1-E15, wherein at least part of the γδ T cells are activated to Vγ9δ2+ γδ T cells.

E18. The iPSC of any one of embodiments E1-E17, wherein the step for performing a function of reprogramming the γδ T cells to a pluripotent state comprises transducing the γδ T cells with a viral vector encoding one or more reprogramming factors; and culturing the transduced γδ T cells under conditions suitable for reprogramming mammalian somatic cells to a pluripotent state.

E19. The iPSC of embodiment E18, wherein the viral vector is a Sendai virus (SeV) vector.

E20. The iPSC of embodiment E18 or E19, wherein the one or more reprogramming factors are selected from a group consisting of OCT3/4, SOX2, KLF4, LIN28, and c-Myc.

E21. The iPSC of any one of embodiments E18-E20, wherein the transduced γδ T cells are cultured in the presence of one or more feeder layers.

E22. The iPSC of embodiment E21, wherein the transduced γδ T cells are cultured in the presence of a mono layer of feeder layer.

E23. The iPSC of embodiment E21 or E22, wherein the feeder layer comprises mouse embryonic fibroblasts (MEFs).

E24. An isolated population of induced pluripotent stem cells (iPSCs) comprising pluripotent cells, wherein the pluripotent cells comprise a means for expressing one or more reprogramming factors, and/or wherein the pluripotent cells comprise a means for encoding rearrangement of TRG and TRD genes.

E25. The isolated population of iPSCs of embodiment E24, wherein the reprogramming factors are selected from a group consisting of Oct3/4, Sox2, Klf4, c-Myc, and Lin28.

E26. The isolated population of iPSCs of embodiment E24 or E25, wherein the isolated population of iPSCs are negative for a Sendai virus (SeV) vector.

E27. The isolated population of iPSCs of any one of embodiments E24-E26, wherein the isolated population of iPSCs are derived from γδ T cells.

E28. The isolated population of iPSCs of any one of embodiments E24-E27, wherein the isolated population of iPSCs have rearrangement genes of TRG and TRD gene loci; and wherein optionally the isolated population of iPSCs have Vγ9 and Vδ2 gene arrangements.

E29. The isolated population of iPSCs of any one of embodiments E24-E28, wherein the isolated population of iPSCs are not derived from αβ T cells.

E30. The isolated population of iPSCs of any one of embodiments E24-E29, wherein the isolated population of iPSCs do not produce PCR products from TCRA and TCRB gene loci.

E31. The isolated population of iPSCs of any one of embodiments E24-E30, wherein the isolated population of iPSCs are genomically stable with no loss of a chromosome.

E32. The isolated population of iPSCs of embodiment E31, wherein the genomic stability of the isolated population of iPSCs is determined by Karyotyping analysis.

E33. The isolated population of iPSCs of any one of embodiments E24-E32, wherein the isolated population of iPSCs can grow and maintain in feeder free medium after adoption.

7. EXAMPLES

The following is a description of various methods and materials used in the studies. They are put forth so as to provide those of ordinary skill in the art with a complete disclosure and description of how to make and use the present invention, and are not intended to limit the scope of what the inventors regard as their invention, nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, percentages, etc.), but some experimental errors and deviations should be accounted for.

7.1. Example 1: Selective Activation and Enrichment of γδ T Cells from PBMCs Culture To generate γδ T-cell derived iPSCs, whole PBMCs from healthy individuals were cultured with zoledronic acid monohydrate (Zol), Interleukin-2, and Interleukin-15 (Zol+ IL-2+ IL-15) for various periods of time (3 days, 8 days and 13 days). To find out the ideal time point to derive iPSCs from Zol-stimulated PBMCs, cell-cell clumps were enriched from day 3, day 8 or day 13 PBMC cultures (FIG. 1, top row). From day 3 after Zol stimulation of PBMCs, cell-cell clumps or blasts, which contains activated cells, could be observed.

Owing to the selective nature of Zol in activating and/or expanding Vγ9⁺ γδ T cells, it was hypothesized that the cell-cell clumps or blasts were largely constituted of Vγ9⁺ γδ T cells. Flow cytometry analysis revealed that the cell-cell clumps consisted of around 35%, 91% and 93% γδ T cells among whole PBMCs on day 3, day 8 and day 13 of the culture periods, respectively (FIG. 1, top row). Among γδ T cells, TCRVγ9⁺ cells constituted about 35%, 96% and 98% of γδ T cells on day 3, day 8 and day 13 of the culture periods, respectively (FIG. 1, bottom row). However, all healthy donors do not respond similarly to Zol-mediated stimulation. Hence, screening and identifying donors that rapidly respond to Zol-mediated stimulation will help find optimal donors for reprogramming.

7.1.1. Selective Activation of Vγ9+γδ T Cells from Whole PBMCs

On day −3, day −8 and day −13, a vial of frozen PBMCs was quickly thawed and added to 49 mL of warm complete RPMI medium in a 50 mL falcon tube to dilute the freezing medium. Complete RPMI medium comprises RPMI (cat #61870-036, Gibco), 10% FBS (cat #10099-141, Gibco) and 1× Pen/Strep (cat #15070-063, Gibco). PBMCs were centrifuged at 1500 rpm for 5 min. Cells were washed once by re-suspending them in 35 mL of complete RPMI medium (RPMI+10% FBS+1× Pen/Strep). The cell pellet was re-suspended in complete RPMI media and the cells were counted. Alternatively, PBMCs were isolated from whole blood sample by density gradient centrifugation and the cells were counted by using hemocytometer. Cell density was adjusted to $1.0 \times 10^6$ cells/mL in complete RPMI media.

Meanwhile, prepared γδ T cell culture medium (RPMI-10%; RPMI supplemented with 10% FBS and 1× Pen/Strep) was supplemented with recombinant human IL-2 (rhIL-2) (cat #202-IL, R&D Systems) to a final concentration of 1000 IU/mL, recombinant human rhIL-15 (cat #247-ILB-025, R&D Systems) to a final concentration of 10 ng/mL and zoledronic acid to a final concentration of 5 μM. Cell density was adjusted to $1 \times 10^6$ cells/mL with the prepared γδ T cell culture media. $10 \times 10^6$ cells were seeded in 10 mL of the culture medium in a T-75 flask.

(1) For day −3 Zol-activated PBMCs, cell enrichment was performed without any additional medium in between day −3 and day 0.
(2) For day −8 Zol-activated PBMCs, 10 mL of culture medium containing 2× concentration of IL-2 (200 IU) and IL-15 (20 ng/mL) was topped up on day −5 to reach final concentrations of IL-2 and IL-15 at 100 IU and 10 ng/mL, respectively. Cell blasts formation were observed under microscopy. Further on day −3, cells were spun down at 1500 rpm for 5 min at room temperature. Cell pellet was re-suspended in 40 mL of culture medium (RPMI+ 10% FBS+1× Pen/Strep) containing 100 IU IL-2 and 10 ng/mL IL-15 on day −3 of the culture.
(3) For day −13 Zol-activated PBMCs, 10 mL of culture medium containing 2× concentration of IL-2 (200 IU) and IL-15 (20 ng/mL) was topped up on day −11. Cell blasts formation were observed under microscopy. Further on day −7, cells were spun down at 1500 rpm for 5 min at room temperature. Cell pellet was re-suspended in 40 mL of culture medium (RPMI+10% FBS+1× Pen/Strep) containing 100 IU IL-2 and 10 ng/mL IL-15 on day −7 of the culture. Further on day −5, cells were spun down at 1500 rpm for 5 min at room temperature. Cell pellet was re-suspended in 40 mL of culture medium (RPMI+10% FBS+1× Pen/Strep) containing 100 IU IL-2 and 10 ng/mL IL-15 on day −5 of the culture. Further on day −3, cells were spun down at 1500 rpm for 5 min at room temperature. Cell pellet was resuspended in 40 mL of culture medium (RPMI+ 10% FBS+1× Pen/Strep) containing 100 IU IL-2 and 10 ng/mL IL-15 on day −3 of the culture.

7.1.2. Enrichment of γδ T Cells

Activated γδ T cells were enriched indirectly via cell-cell clump enrichment. On day 0, T-75 cm² cell culture flasks containing Zol-cultured PBMCs (for 3 days, 8 days, and 13 days, respectively) were tilted at 45-degree angle and the supernatant medium was aspirated out using a 10 mL steripipette without disturbing the sedimented cells. Remaining sedimented population largely consists of clumps of activated cells. Vγ9⁺ γδ T cells among whole PBMCs were selectively activated by Zol. Activated cells formed cell-cell clumps or blasts. These cell clumps had higher sedimentation rate compared to single cells, while the supernatant medium largely consisted of single cells.

Enrichment of pure populations of γδ T cells was performed using EasySep™ Human γδ T cell isolation kit (Stemcell Technologies) according to the manufacturer's instructions.

Day 3 or day 8 Zol cultured PBMCs were harvested and spun down at 1500 rpm for 5 min at room temperature. γδ T cells enriched from day 3 or day 8 Zol stimulated PBMCs were used for SeV vector transduction.

Cells were washed once by re-suspending them in plain RPMI (no FBS, or 1× Pen/Strep) medium, and spun down at 1500 rpm for 5 min. Cell pellet was re-suspended in 1 mL of EasySep™ buffer (cat #20144, STEMCELL Technologies) and cells were counted by hemocytometer.

Cell density of the sedimented cell clumps was adjusted to $50 \times 10^6$ cells in 1 mL of EasySep buffer in a 5 mL polystyrene round bottom tube. 50 μL of biotinylated cocktail was added to the re-suspended cells, mixed and incubated at room temperature for 15 minutes. Before the end of the incubation period, EasySep magnetic particles were vortexed for 30 seconds to get them evenly dispersed. After the incubation period, 50 μL of EasySep magnetic particles were added to 1 mL of re-suspended cells, mixed and incubated at room temperature for 10 min.

After the incubation period, 1.5 mL of EasySep™ buffer was added to top up the tube containing the cells, which were re-suspended by gently mixing the cells up and down. The tube was placed onto the magnet stand and incubated for 5 minutes at room temperature.

At the end of the incubation period, medium containing enriched cell suspension was collected by inverting the magnet containing the tube in one continuous motion. In the multiple tube scenario, supernatants were collected from the tubes while they were on the magnet stand, without disturbing the bound magnetic particles, by using a 1 mL pipette hand.

37 μl of vortexed magnetic particles was added to the enriched cell suspension, which was then mixed and incubated at room temperature for 5 minutes. The tube containing cell suspension was placed onto the magnet stand and incubated at room temperature for 5 minutes. Enriched cells were collected by transferring the cell suspension into a new 15 mL tube by inverting the magnet containing the tube in one continuous motion. The tube was then topped up with 10 mL of complete RPMI media (RPMI+10% FBS+1× Pen/Strep).

Cells were spun down at 1500 rpm for 5 min at room temperature and washed one more time by adding 10 mL of complete RPMI medium. Cells were spun down at 1500 rpm for 5 minutes at room temperature, re-suspended in 1 mL of complete RPMI medium and counted by hemocytometer. The purity of the enriched γδ T cells were checked on flow cytometer by staining the cells with mAbs against TCR γδ, TCR αβ and TCR Vγ9.

7.2. Example 2: Generation of Human γδ T-Cell Derived iPSCs from PBMCs Culture Cell-cell clumps (or blasts) were subjected to transduction with Sendai virus (SeV) vector encoding OCT3/4, SOX2, KLF4, and c-Myc reprogramming factors. SeV vector transduced cells were propagated on mitotically inactivated MEF feeder layers, T-cell depleted autologous PBMCs, and/or feeder free conditions, as described below in Section 7.2.1 through Section 7.2.5.

Colonies started to be observed on about day 20 after SeV transduction and reached the maximum number around day 26. Surprisingly, only PBMC culture stimulated by Zol+IL-2+IL-15 for 3 days yielded considerable number of colonies after 20 days of SeV transduction. In contrast, PBMC cultures stimulated by Zol+IL-2+IL-15 for 8 days or 13 days did not yield considerable number of colonies after SeV transduction.

This surprising observation indicates that the less enriched cells (for 3 days) are highly prone to re-programming, compared to more enriched cells (for 8 days or for 13 days).

As shown in FIGS. 2A and 2B, undifferentiated iPSCs colonies of different clones (Clones A-C) on MEF feeder layers were identified as round colonies with smooth and tight borders, and compact cells inside tight borders with no heterotrophic centers. Clones A-C were from the same donor.

In contrast, none of the experiment groups (enriched for 3 days, 8 days, or 13 days) of SeV-transduced PBMCs that were grown on laminin-511 coated plates (feeder free culture) or co-cultured with mitotically inactivated T cell depleted autologous PBMCs (feeder-based culture) yielded any colonies. Enriched γδ T cells from day 8 PBMC cultures grown on MEF feeder layers also did not yield any colonies.

Further, mRNA- or episomal-mediated reprogramming was examined as an alternative to Sendai virus (SeV)-mediated re-programming. Since Zol activated PBMCs were not resistant to repeated electroporation-mediated mRNA transfection, studies on mRNA-mediated reprogramming could not be pursued further. Episomal-mediated reprogramming yielded very few colonies. Therefore, SeV-mediated reprogramming was observed to be the most efficient method to reprogram Zol activated γδ T cells.

7.2.1. Coating Cell Culture Plates with Extracellular Matrix

Gelatin Coating 2 mL of 0.1% gelatin solution (cat #ES-006-B, Merck) was added to a well of a 6-well cell culture plate and incubated either at room temperature for two hours or at 37° C. for one hour.

At the end of the incubation period, the gelatin solution was aspirated using a vacuum based aspirator with care so that the surface area of the well does not come into contact with the aspirator. Cells (e.g., mouse embryonic fibroblasts) were added to the well without any delay.

iMatrix-511 Coating iMatrix-511 (cat #892011, Nippi/Matrixome) solution at a stock concentration of 0.5 mg/mL was diluted with sterile DPBS (cat #14190-136, Gibco). Dishes were coated with diluted iMatrix-511 at a concentration of 0.5 μg/cm². For one well of a 6-well plate (9.6 cm²/well), 9.6 μL of iMatrix-511 (4.8 μg) was added into 1.99 mL of sterile DPBS and incubated at 4° C. overnight, at 37° C. for 1 hour or at room temperature for 3 hours.

After the incubation period, diluted iMatrix-511 was aspirated from the well with care so that the surface area of the well does not come into contact with the aspirator and that the wells are not air-dried.

The required medium was added to the wells immediately so as not to allow the plate to dry. The medium needs to be added along the walls drop-wise to the wells. No rinsing is needed in between aspiration and cell seeding. Cells were plated immediately at a desired density. The plate was placed back into the incubator.

Vitronectin Coating

A vial of vitronectin (cat #A14700, Gibco) at a stock concentration of 0.5 mg/mL was thawed at room temperature. 60 μL aliquots of vitronectin were prepared in polypropylene tubes. These aliquots were used immediately or frozen at −80° C.

To coat the wells of a 6-well plate, two 60-4, aliquots of vitronectin were removed from −80° C. storage and thawed at room temperature. Two 60-4, aliquots were needed for every 6-well plate.

120 μL of thawed vitronectin was added into a 15-mL conical tube containing 12 mL of sterile DPBS without calcium or magnesium at room temperature, and gently resuspended by pipetting the diluted vitronectin up and down. This resulted in a working concentration of vitronectin at 5 μg/mL (i.e., a 1:100 dilution)

2 mL of the diluted vitronectin solution was added into each well of a 6-well plate. When used to coat a 6-well plate (10 cm²/well) at 2 mL/well, the final concentration of vitronectin will be 0.5 μg/cm². The coated plates were incubated at 37° C. for 3 hours (or at room temperature for 1 hour pursuant to the manufacturer of vitronectin).

Coated plates can be used or stored at 2-8° C. wrapped in laboratory film for up to a week. But the coated plates cannot be dried. Prior to use, a coated plate was pre-warmed to room temperature for at least 1 hour.

The vitronectin solution was aspirated and discarded. It is not necessary to rinse coated plate after the removal of vitronectin. Cells can be passaged directly onto the vitronectin-coated plates.

7.2.2. Preparation of Mitotically Inactivated Mouse Embryonic Fibroblasts (MEF) Cell Culture Mouse Embryonic Fibroblasts (MEF) Revival MEF (CF-1) (cat #SCRC-1040, ATCC) cell line was procured from ATCC as frozen vials. A Frozen vial of MEF cells was quickly thawed in a 37° C. water bath. The thawed content was added to a 50 mL falcon tube containing 40 mL of 37° C. pre-warmed MEF medium, which comprises DMEM (cat #11965-092, Gibco), 15% FBS and 1% Pen/Strep, in a drop wise manner. MEF cells were spun down at 1500 rpm for 5 min at room temperature, with the supernatant discarded. Cells were washed once with 30 mL of MEF medium (DMEM+15% FBS+1% Pen/Strep) and spun down at 1500 rpm for 5 min at room temperature. Cells were then counted on hemocytometer using trypan blue (cat #TCL046, Himedia).

MEF Seeding and Culture

MEFs were seeded in a T-75 cm$^2$ flask at a density of $0.8 \times 10^6$ cells in 20-25 mL of MEF medium (DMEM+15% FBS+1% Pen/Strep). Alternatively, MEFs were seeded in T-150 flasks at a density of $1 \times 10^6$ cells in 40 mL of MEF medium. MEFs were incubated at 37° C. in a humidified incubator with 7.5-10% $CO_2$. To grow MEFs at 7.5-10% $CO_2$, the medium should contain 3.7 g/L sodium bicarbonate. Cells were subcultured (as described below) when the cell culture reached 60-70% confluency.

MEF Subculture

MEF culture medium was removed and discarded. The cell layer was then rinsed with 20 mL (for T-75 flasks) or 40 mL (for T-175 flask) sterile DPBS. 4 mL (for a T-75 flask) or 10 mL (for a T-175 flask) of pre-warmed Trypsin-EDTA (cat #25200-056, Gibco) was added and the mixture was incubated for 2-5 minutes. MEFs detached from the flask, as observed under microscope, and disassociated to form a single cell suspension. Trypsin was neutralized by adding twice the amount of complete MEF culture medium (DMEM+15% FBS+1% Pen/Strep) into the flask.

All cells were transferred into a centrifuge tube and centrifuged at 1500 rpm for 5 minutes at room temperature. After discarding the supernatant, 10 mL complete growth medium was added to the cell pellet. Cells were suspended gently with a 10 mL pipette to create a single cell suspension. Additional MEF culture medium was added to the single cell suspension as needed for subculturing.

For subculturing, MEF cells were split at 1:2 or 1:3 ratio, depending upon the requirement. Cells were incubated in flasks in a 37° C. humidified incubator containing 7.5-10% $CO_2$. If the MEFs are being used as a feeder layer for iPSCs, it is not recommended to use them past passage No. 6 (P6).

MEF Freezing

MEF cells were frozen at a cell density of 5 million/cryovial in 1 ml of freezing medium (Complete MEF medium supplemented with additional 40% FBS and 10% (v/v) DMSO (cat #D2650, Sigma)).

Cryovials were stored overnight at –80° C. in a step cooler and transferred to liquid nitrogen the next day.

Mitotic Inactivation of MEF Cells

A vial of frozen MEFs (<passage number 5) was quickly thawed in a 37° C. water bath and added drop-wise to 49 mL of pre-warmed complete MEF media (DMEM+15% FBS+1× Pen Strep) in a 50 mL falcon tube. Cells were centrifuged at 1500 rpm for 5 minutes at room temperature and washed once with phosphate buffered saline (PBS). One million of MEFs were seeded in 40 mL of MEF medium (DMEM+15% FBS+1% Pen/Strep) in a T-150 cm$^2$ flask, and incubated at 37° C. in a humidified incubator with 7.5% $CO_2$. To grow MEFs at 7.5% $CO_2$, the DMEM medium should contain 3.7 g/L sodium bicarbonate. On day 2 of culture, the medium was replaced with fresh MEF medium. After 3-3.5 days of culture, MEF cells reached sub-confluent stage (approximately 70% confluency).

Mitomycin-C master stock was prepared at a concentration of 1 mg/mL in double distilled $H_2O$ (dd $H_2O$). Mitomycin-C was added to a final working concentration of 10 µg (10 µl) per milliliter of MEF culture medium (DMEM+15% FBS+1× Pen/Strep). For a T-150 cm$^2$ flask containing log phase passage 3 MEFs, added 400 µL of Mitomycin-C (1 mg/mL stock concentration) to 40 mL of MEF culture medium (DMEM+15% FBS+1× Pen/Strep). The mixture was incubated in the flask for 2 hours at 37° C. in a humidified incubator with 7.5% $CO_2$. After the incubation period, the medium containing Mitomycin-C was aspirated. Cell were washed with 40 mL of plain DMEM medium repeatedly for ten (10) times. Vigorous washing is needed to remove any remnants of Mitomycin-C because the presence of remnants of Mitomycin-C will prevent proliferation of any co-cultured cells. As a last wash, cells were washed once with 40 mL of DPBS.

10 mL of 1× Trypsin-EDTA was added to the washed T-150 cm$^2$ flask containing MEF cells. Incubated at 37° C. in a humidified incubator with 7.5% $CO_2$ for 3-5 minutes. After the incubation period, trypsin was neutralize by adding 20 mL of complete MEF medium (DMEM+ 15% FBS+ Pen/Strep). Cells were spun down at 1500 rpm for 5 minutes at room temperature. After washing, mitomycin-C treated MEFs were used either directly or frozen down for downstream applications.

7.2.3. Sendai Virus (SeV) Vector Mediated Reprogramming of γδ T Cells

Day 0: Sendai Virus Infection

Cells were counted using trypan blue. Half a million cell-cell clump enriched PBMCs or γδ T cells were pipetted in a well of low adherent 24-well plate. Low adherent plates are crucial to prevent any cells, including PBMCs, from attaching to each other during or after SeV infection.

Pure population γδ T cells were enriched, without the contamination of any αβ T cells or other cells, only from PBMCs harvested on day 8 and 13 of PBMC culture with Zol+IL-2+IL-15 culture.

Cytotune™ 2.0 tubes (cat #A16517, Thermo Fischer Scientific) were removed from –80° C. and quickly thawed in a 37° C. water bath one by one for 5 to 10 seconds. Once thawed, these tubes were placed on ice.

Calculated volumes of KOS, hc-Myc and hKlf4 containing Sendai virus particles were added to the cells in 0.3 mL of complete RPMI medium (RPMI+10% FBS) at a multiplicity of infection (MOI, calculated based on the titer that is specific for each lot of Cyotune™ 2.0 kit) of 5, 5 and 3, respectively. Complete culture medium was supplemented with 100 IU IL-2 and 10 ng/mL IL-15. Polybrene (cat #TR-1003-G, Millipore) was added to the cell suspension containing virus at a concentration of 4 µg/mL.

Day 1: Replace Medium and Culture Cells

Cells and medium were removed from the culture plate and transferred to a 15 mL falcon tube. The wells in the plate were rinsed gently with 1 mL of complete RPMI medium (RPMI+10% FBS+1× Pen/Strep) to ensure most of the cells were harvested. Complete culture medium was supplemented with 100 IU IL-2 and 10 ng/mL IL-15.

Cytotune™ 2.0 Sendai viruses were removed from the cell suspension by spinning the cells at 200×g for 10 minutes at room temperature. The medium was aspirated and the cell pellet was resuspended in 0.5 mL of complete RPMI medium in a low adherent 24-well plate.

Cells were cultured at 37° C. in a humidified incubator of 5% $CO_2$ for 2 days in complete RPMI medium (RPMI+10% FBS+1% Pen/Strep).

Day 3: Transfer Transduced Cells—Feeder Layers (MEFs) Condition

Feeder layers were mitotically arrested using Mitomycin-C (cat #M4287, Millipore). A detailed protocol for treating MEFs with Mitomycin-C is described in Section 7.2.2. Mitotically arrested MEFs were plated on gelatin-coated wells of a 6-well plate. It is advisable to plate mitotic arrested MEFs a day or two before seeding the transduced cells onto them. Whether Mitomycin-C arrested MEFs' cell cycle was checked by measuring the medium consumption by mitotically arrested MEFs at 37° C., 5% $CO_2$ over a period of 7 days. Whether Mitomycin-C actually arrested MEFs' cell cycle or not should always be checked SeV transduced cell-cell clump enriched PBMCs or γδ T cells were counted and seeded onto MEF monolayer in 2 mL of complete RPMI medium in a 6-well plate at varying cell densities (from 10,000 to 100,000 cells/well in a 6-well plate). Complete culture medium was supplemented with 100 IU IL-2 and 10 ng/mL IL-15.

Day 3: Transfer Transduced Cells—Feeder Free Condition (onto iMatrix-511 Coated Plates)

6-well plates were coated with laminin 511-E8 fragments (a detailed protocol for coating plates with iMatrix-511 is described in Section 7.2.1) on the day SeV transduced cell-cell clump enriched PBMCs or γδ T cells were to be seeded.

SeV transduced PBMCs or γδ T cells were seeded onto laminin 511-E8 fragment-coated wells in 2 mL of complete RPMI culture medium at various cell densities (from 10,000 to 100,000 cells/well in a 6-well plate).

Days 5, 7, 9 and 11: Medium Change

Half of the used complete RPMI medium (1 mL) was taken out without disturbing the cells and the well was replenished with 1 mL of fresh StemFit Basic 2.0 (cat #SFB500, AJINOMOTO) containing 100 ng/mL of basic fibroblastic growth factors (bFGFs) (cat #AMS-480-100, Amsbio). The final working concentration of bFGF was 50 ng/mL.

While replenishing the medium with fresh medium on day 7, 9 and 11, bFGF was added in 2× concentration, i.e, 100 ng/mL.

Days 13, 15, 17, 19 and 21: Complete Replenishment of Medium 1.5 mL of old medium was removed and the well was replenished with 2 mL StemFit Basic 2.0 medium containing 50 ng/mL bFGF. Colonies were observed everyday, and developing colonies were marked with a marker pen and followed up.

7.2.4. Colony Pickup and Propagation

Once the colonies were prominent, i.e., around day 23 or so, manual colony pickup was prepared for. The 6-well plate containing iPSC colonies was taken out from the incubator and cells were observed under the microscope.

Undifferentiated colonies were marked with a marker pen. A picture or two was taken of these colonies for reference purposes. Once the identification of the colonies was completed, the plate was taken to the laminar hood.

Used medium was aspirated from the wells using a vacuum pump. For a feeder-based culture, 800 μL of TrypLE (cat #12563-029, Gibco) disassociation reagent, which was prediluted with sterile DPBS in a 1:1 dilution, was added to a well in a 6-well plate. The plate was incubated at 37° C. in a humidified incubator containing 5% $CO_2$ for 4 minutes.

For a feeder-free culture, 800 μL of TrypLE disassociation reagent, which was prediluted with sterile DPBS in a 1:1 dilution, was added to a well in a 6-well plate. The plate was incubated at 37° C. in a humidified incubator containing 5% $CO_2$ for 1 minute.

At the end of the incubation period, the plate was taken out from the incubator and tilted gently. The entirety of the TrypLE reagent present in the well was aspirated with a 1 mL pipette. 2 mL of StemFit Basic2.0 medium contained 10 μM ROCK inhibitor (cat #SCM075, Merck Millipore) and bFGF was added to the well.

For a feeder-free culture, 2 mL of mTeSR medium (cat #85850, STEMCELL Technologies) containing 10 μM ROCK inhibitor was added (without any bFGF) to the well.

Plates containing StemFit Basic2.0 (feeder-based culture) or mTeSR (feeder-free) medium was taken to the inverted microscope (OLYMPUS, model CKX53SF, S. no 8M44621) for colony picking. In the meantime, an inverted microscope was mobilized inside the laminar hood. It is important to make sure that the microscope is clean and sanitized before moving it into the laminar hood. The microscope was adjusted the focus on the pre-marked colonies, which were scraped back and forth using a gel loading tip with an elongated mouth mounted onto a 200 μL pipettor. Colonies were divided by scraping into small square chunks.

Colonies can be collected either with little scrapping to prevent contamination from adjacent colony or the whole colonies can be collected by a 200 μL tip and transferred into a well in a 96-well plate that contained either 200 μL of StemFit Basic2.0 medium containing ROCK inhibitors and bFGFs for a feeder-based culture or mTeSR medium containing ROCK inhibitors with no bFGFs for a feeder-free culture.

Scrapped chunks were collected using a 200 μL pipettor and immediately transferred onto either irradiated MEF monolayer seeded plates in StemFit Basic2.0 medium containing 10 μM ROCK inhibitors and 100 ng/mL bFGFs (feeder-based culture) or laminin-511/vitronectin coated plates (feeder-free culture) in mTeSR medium containing 10 μM ROCK inhibitors just for the 24 hours on Day 0 and no ROCK inhibitors thereafter.

Irradiated MEFs were obtained from ATCC as frozen vials (cat #SCRC-1040.1, ATCC) and thawed as described by ATCC. Thawed cells were counted and seeded on gelatin-coated plates at a density of 0.5 million cells/well in a 6-well plate in MEF culture medium (which density may vary according to different conditions), one day before the iPSC colony was transferred onto them. Unlike Mitomycin-C treated MEF monolayers, irradiated MEF monolayers persisted only for 5 to 7 days.

The whole procedure of colony picking needed to be done quickly. Long exposure of the colonies to external environment may lead to improper attachment and/or differentiation of cells in the colonies.

The plate was in a figure-8 pattern and transferred to a humidified incubator containing 5% $CO_2$ at 37° C. The colonies were cultured without any disturbance for the next 48 hours. During the 48 hours of cell culture, 2 mL fresh medium was used to replace used medium in one well of a 6-well plate every 24 hours up to the next passage.

Passage intervals depended on the growth of the iPSC colonies, which may vary from donor to donor. Typically, each passage took 3 to 5 days. A large number of differentiated cells were observed until the end of the first four passages. From passage 5 and onwards, undifferentiated colonies were observed.

The above mentioned procedure can be repeated for a new passage cycle. The plates were observed on a daily basis.

7.2.5. iPSCs Colony Freezing and Thawing iPSCs Colony Freezing

The plate was taken out from the incubator and cells were observed under inverted microscope. Undifferentiated colonies (colonies with smooth and tight borders, and compact cells inside tight borders with no heterotrophic centers) were marked with a marker pen. A picture or two was taken of these colonies for reference purposes. Once the identification of the colonies was completed, the plate was taken to the laminar hood.

Used medium was aspirated from the wells using a vacuum pump. For a feeder-based culture, 800 µL of TrypLE disassociation reagent, which was prediluted with sterile DPBS in a 1:1 dilution, was added to a well in a 6-well plate. The plate was incubated at 37° C. in a humidified incubator containing 5% $CO_2$ for 2-4 minutes (for feeder-based culture) or 1 minute (for feeder-free culture).

At the end of the incubation period, the plate was taken out from the incubator and tilted gently. The entirety of the TrypLE reagent present in the well was aspirated with a vacuum pump. The well was washed with plain medium. 2 mL of StemFit Basic2.0 medium (for feeder-based culture) or mTeSR medium (for feeder-free culture) was added to the well.

The plate was taken under the microscope for colony picking. All differentiated colonies were selectively dislodged using a gel loading tip, with elongated mouth, mounted onto a 200 µL pipettor. The plate was washed with 2 mL of StemFit Basic2.0 medium (for feeder-based culture) or mTeSR medium (for feeder-free culture), which medium was then aspirated with a vacuum pump. The washing step was repeated one more time. After these two washes, most of the dislodged differentiated colonies were removed from the plate.

For feeder-based cultures, undifferentiated colonies were picked into an Eppendorf tube, as described in Section 7.2.4. For feeder-free cultures, the remaining undifferentiated colonies were scraped from the well using a scrapper and collected in a 1.5 mL Eppendorf tube.

Cells were spun down at 100×g for 30 seconds at room temperature. The supernatant was discarded using 1 mL pipettor. The cell pellet was resuspended gently in 1 mL of freezing medium (ES-FBS+10% DMSO) or alternatively, Knock out serum replacement (KnockOutTMSR, cat #10828028, Thermo Fisher Scientific) with 10% DMSO as freezing medium.

Vial were stored in a step cooler and placed in −80° C. for overnight and transferred to storage in liquid nitrogen the very next day.

iPSCs Colony Thawing

A vial of frozen iPSCs (from a feeder-based or feeder-free culture) was quickly thawed in 37° C. water bath. Content of the vial was added drop by drop to a 50 mL conical tube containing 25 mL of StemFit Basic 2.0 medium (for feeder-based culture) or mTeSR medium (for feeder-free culture) containing 10 µM ROCK inhibitors. It is important to makes sure the cells are added drop by drop because sudden addition of cells into the medium will cause osmotic shock.

Cells were spun down at 1200 rpm for 5 minutes at room temperature. The supernatant was discarded and cells were gently resuspended in 2 mL of StemFit Basic 2.0 medium containing 10 µM ROCK inhibitors and 100 ng/mL bFGFs (for feeder-based culture) or mTeSR medium (feeder-free culture) containing 10 µM ROCK inhibitors. The ROCK inhibitors in the culture medium will help prevent iPSCs' spontaneous differentiation and improve their survival while thawing.

The re-suspended iPSC chunks were seeded into a 6-well plate that was either pre-seeded with irradiated MEFs (as described in Section 7.2.4) or pre-coated with vitronectin (as described in Section 7.2.1) for feeder-based and feeder-free cultures, respectively.

The plate was incubated at 37° C. in a humidified incubator containing 5% $CO_2$ for 24 hours. After 24 hours of incubation, culture medium containing ROCK inhibitors was replaced with fresh medium without ROCK inhibitors but with bFGFs, although no substantial difference were observed even if ROCK inhibitors continued to be used throughout the culture. Used medium was replaced with 2 mL fresh medium for one well of a 6-well plate every 24 hours up to the next passage.

Passage intervals depended on the recovery and growth of the iPSC colonies. Growth of colonies varies from donor to donor. However, recovery of colonies depends on how well the iPSC colonies were frozen and thawed. Typically, each passage takes 3-5 days on average.

Compromised colonies may take longer (7-10 days) to recover. Culture medium needs to be replaced with fresh medium every 24 hours until iPSCs recover completely.

Recovered colonies initially produced a lot of differentiated cells (until passage 4 or 5). From passage 5 and onwards, prominent undifferentiated colonies can be observed.

7.3. Example 3: Characterization of TRG and TRD Gene Rearrangements in γδ T Cell-Derived iPSCs iPSCs colonies that were derived from 3-day Zol activated PBMCs were examined for the rearrangement at the TRG and TRD gene loci. As a first step, genomic DNAs from all five iPSC colonies and the 22Rv1 cell line were isolated, as described in Section 7.3.1. Genomic PCR was carried out with primers (against TRG loci) from Identi-Clone™ T cell receptor gamma gene rearrangement assay kit (cat #1-207-0101, Invivoscribe) to assess the gene rearrangement at TRG locus following the procedure as described in Section 7.3.2.

Upon subjecting amplicons obtained from genomic PCR to capillary electrophoresis, as detailed in Section 7.3.2, amplicon of desired sizes of approximately 191 and 192 bp were observed in all clones, which confirmed specific Vγ9 gene rearrangement at the TRG locus (FIG. 3). However, FIG. 3 also shows additional amplicons of sizes approximately 180 and 182 bp in Clones A, B and C, indicating the possibility of having other Vγ gene rearrangements in these clones.

Given that the T cell receptor gamma gene rearrangement assay did not generate the confirmatory result and the possibility of artefacts associated with ABI detection systems (as detailed in Section 7.3.2), genomic PCR was performed using the published primers specific to the variable region (Vγ9) and the joining region (JP1/JP2, JP) of the TRG locus and the variable region (Vγ2) and the joining region of (Jδ1 and Jδ3) of the TRD locus. Published primer sequences for genomic PCR analysis of TRG and TRD gene rearrangement are provide din Table 2 below.

TABLE 2

| TCR Gene Sequences | | |
|---|---|---|
| | TCR Gene | Nucleotide Sequence (5' to 3') |
| Sense Primer | Vγ9 | CGGCACTGTCAGAAAGGAATC (SEQ ID NO: 27) |
| | Vδ2 | ATACCGAGAAAAGGACATCTATG (SEQ ID NO: 28) |

TABLE 2-continued

TCR Gene Sequences

| | TCR Gene | Nucleotide Sequence (5' to 3') |
|---|---|---|
| Anti-sense Primer | JP1/JP2 | GAAGTTACTATGAGCTTAGTCCCTT (SEQ ID NO: 29) |
| | JP | AAGCTTTGTTCCGGGACCAAATAC (SEQ ID NO: 30) |
| | J1/J2 | TACCTGTGACAACAAGTGTTGTTC (SEQ ID NO: 31) |
| | Jδ1 | GTTCCACAGTCACACGGGTTC (SEQ ID NO: 32) |
| | Jδ3 | CTCACGGGGCTCCACGAAGAG (SEQ ID NO: 33) |

In the genomic PCT analyses performed, iPSCs colonies from Clones A, B and C all showed rearrangements of the TRG and TRD genes. Gene rearrangements were identified as single bands representing Vγ9-JP and Vδ2-Jδ1 or Jδ3 recombinations, indicating that these colonies carried rearranged Vγ9Vδ2-TCR genes. For all three clones, rearrangements of the TRG gene were detected as single bands representing Vγ9-JP. For Clone A, TCR gene rearrangement was detected as Vδ2-Jδ1. For clones B and C, Vδ2-Jδ3 recombination was detected, which indicated that these clones carried Vγ9 and Vδ2 gene rearrangements (FIG. 4). GAPDH amplification was observed in all three clones as a housekeeping control gene.

No amplification was observed with genomic DNA isolated from the 22Rv1 cell line, which reaffirmed the specific nature of genomic primers used in this study (FIG. 4). Further, FIG. 4 also shows that no amplification was observed from the genomic DNA of Clones A, B and C when amplified with primers against TCRα and TCRβ, confirming that these colonies are not from αβ T-cells. Further, sequencing of the amplicons and BLASTing the sequences against the whole human genome confirmed successful Vγ9 and Vδ2 gene arrangements in all the clones (FIG. 5 for Clone B, and FIGS. 6A-6D for Clones A, C, D, and E) at the TRG and TRD gene loci. Amplicons were ran on 1% agarose gel for Clones A, B and C only, whereas all five clones were subjected to genomic PCR with specific primers and sequencing (FIGS. 5 and 6A-6D).

7.3.1. Genomic DNA Isolation

The genomic DNA from the iPSC colonies and 22Rv1 cells was isolated using GenElute™ mammalian genomic DNA miniprep kit (cat #G1N70-1Kt, Sigma) as described in detail in the following protocol.

Undifferentiated iPSC colonies were picked up as described in Section 7.2.4. Cells were pelleted at 200×g for 30 seconds at room temperature. The culture medium was carefully removed using a 1 mL pipettor until there was no left over medium in the tube. Cells were flash frozen in liquid nitrogen and stored at −80° C. for future use.

The cell pellet was thawed slowly on ice for 10-20 minutes and resuspended thoroughly in 200 µL of Resuspension Solution. 20 µL of RNase A solution was added and the mixture was incubated for 2 minutes at room temperature. 20 µL of the Proteinase K solution was added to the sample, followed by the addition of 200 µL of Lysis Solution C (B8803). The mixture was vortexed thoroughly for about 15 seconds and incubated at 70° C. for 10 minutes. A homogeneous mixture is essential for efficient lysis.

500 µL of the Column Preparation Solution, which maximizes binding of DNA to the membrane resulting in more consistent yields, was added to each pre-assembled GenElute™ Miniprep Binding Column. The column was centrifuged at 12,000×g for 1 minute on a bench top Eppendorf centrifuge. The flow through liquid was discarded.

200 µL of ethanol (95-100%) was added to the lysate mixture; mixed thoroughly by vertexing the mixture 5-10 seconds. A homogeneous solution is essential.

The entire content of the tube was transferred into the treated binding column using a wide bore pipette tip to reduce shearing of the DNA during transferring. The column was centrifuge at ≥6500×g for 1 minute. The collection tube containing the flow through liquid was discarded. The binding column was placed in a new 2 mL collection tube.

Prior to the first use, the Wash Solution Concentrate was diluted with ethanol pursuant to manufacturer's instructions. 500 µL of Wash Solution was added to the binding column, which was centrifuged for 1 minute at 6,500×g. The collection tube containing the flow through liquid was discarded. The binding column was placed in a new 2 mL collection tube.

Another 500 µL of Wash Solution was added to the binding column, which was centrifuged for 3 minutes at maximum speed (12,000-16,000×g) to dry the binding column. The binding column must be free of ethanol before eluting the DNA. The column was centrifuged for one additional minute at maximum speed if residual ethanol was observed. The collection tube containing the flow through liquid was discarded. The binding column was placed in a new 2 mL collection tube.

200 µL of the Elution Solution was pipetted directly into the center of the binding column, which was centrifuged for 1 minute at 6,500×g to elute the DNA. To increase the elution efficiency, the binding column was incubated for 5 minutes at room temperature after adding the Elution Solution, and then centrifuged.

7.3.2. T Cell Receptor Gamma Gene Rearrangement Assay 2.0

IdentiClone™ T Cell Receptor Gamma Gene Rearrangement Assay 2.0 PCR assay employs multiple consensus DNA primers that target conserved genetic regions within the T cell receptor gamma chain gene. Genomic DNA was isolated from the given clones followed by amplifying the region using IdentiClone T Cell Receptor Gamma Gene Rearrangement Assay 2.0 kit. This kit consists of a single master mix that contains primers (conjugated to 6-FAM fluorescent dye) that target Vγ2, Vγ3, Vγ4, Vγ5, Vγ8, Vγ9, Vγ10 and Vγ11 and Jγ1/Jγ2, JγP and JγP1/JγP2 regions. This was followed by fractionation by capillary electrophoresis and analysis by the GeneMapper software (Eurofins). PCR amplicons have an expected size range between 159 and 207 base pairs.

PCR was performed using the genomic DNA that was isolated from iPSC colonies, with the following PCR conditions. First, a temperature of 95° C. was applied for 3 minutes. Next, the following cycle was applied twenty-five (25) times: 95° C. for 30 seconds, 65° C. for 30 seconds, and 72° C. for 45 seconds. Finally, the temperature was held at 72° C. for 5 minutes, and then the mixture was kept at 25° C. until removed. The PCR mixture (30 µL) consisted of the following ingredients: 15 µL of the 2× Pwo Master (cat #03789403001, Roche), 100 ng DNA template, 0.5 µL of each of the two primers (100 µM), and water to make up to 30 µL.

Initially, only genomic DNA from clone B was used for PCR, as a test to make sure the system was working. PCR samples were submitted to a firm called Eurofins (Bengaluru, India) for analysis and processing pursuant to the kit manufacturer's protocol. The details of the samples are summarized in Table 3 below.

TABLE 3

T Cell Receptor Gamma Gene Rearrangement PCR on Test Sample B

| Sample No. | Sample Content |
|---|---|
| Sample 1 | Test Sample B + TRG 6-FAM Master Mix |
| Sample 2 | Positive control from the kit + TRG 6-FAM Master Mix |
| Sample 3 | Negative control from the kit + TRG 6-FAM Master Mix |
| Sample 4 | Water + TRG 6-FAM Master Mix |
| Sample 5 | Test Sample B + Specimen Control DNA ladder Master Mix |
| Sample 6 | Positive control from the kit + Specimen Control DNA ladder Master Mix |
| Sample 7 | Water + Specimen Control DNA ladder Master Mix |

Upon analysis of the results, based on the presence of peaks at specific sizes of DNA fragments, it was determined that test sample B (clone B) was positive for the rearrangement for Vγ9Vδ2 genes.

The rest of the genomic DNA samples were used to perform the PCRs just as it was done for Clone B and were submitted for analysis to Eurofins again. The details of the samples are summarized in Table 4 below.

TABLE 4

T Cell Receptor Gamma Gene Rearrangement PCR on Test Samples A, C, D, E

| Sample No. | Sample Content |
|---|---|
| Sample 1 | Test Sample A + TRG 6-FAM Master Mix |
| Sample 2 | Test Sample C + TRG 6-FAM Master Mix |
| Sample 3 | Test Sample D + TRG 6-FAM Master Mix |
| Sample 4 | Test Sample E + TRG 6-FAM Master Mix |
| Sample 5 | Test Sample A + Specimen Control DNA ladder Master Mix |
| Sample 6 | Test Sample C + Specimen Control DNA ladder Master Mix |
| Sample 7 | Test Sample D + Specimen Control DNA ladder Master Mix |
| Sample 8 | Test Sample E + Specimen Control DNA ladder Master Mix |
| Sample 9 | Positive control from the kit + TRG 6-FAM Master Mix |
| Sample 10 | Positive control from the kit + Specimen Control DNA ladder Master Mix |
| Sample 11 | Negative control from the kit + TRG 6-FAM Master Mix |
| Sample 12 | Water + TRG 6-FAM Master Mix |
| Sample 13 | Water + Specimen Control DNA ladder Master Mix |

Upon analysis, some of the test samples (clones) were shown to be positive for Vγ9Vδ2 rearrangement, which was only taken as a preliminary result. Sequencing was to be done to confirm these clones. For sequencing, PCR was performed using two pairs of primers for amplifying γ and δ regions, respectively. The sequences of the primers are summarized in Table 5 below.

TABLE 5

PCR Primers for Sequencing

| Primer Pair | Primer name | Sequence |
|---|---|---|
| | TRGV9for | GCAGGTCACCTAGAGCAACC (SEQ ID NO: 34) |
| | TRGJPrev | TGTAATGATAAGCTTTGTTC (SEQ ID NO: 35) |

TABLE 5-continued

PCR Primers for Sequencing

| Primer Pair | Primer name | Sequence |
|---|---|---|
| P10 | TCRVδ2_Fwd | ATACCGAGAAAAGGACATCTATG (SEQ ID NO: 36) |
| | TCRJδ1_Rev | GTTCCACAGTCACACGGGTTC (SEQ ID NO: 37) |

Sample processing and analysis was performed at Eurofin (Bengaluru, India) pursuant to the kit manufacturer's instructions. PCR products ware labelled with 6-FAM. Size standards (ROX or LIZ) and Hi-Di formamide were added pursuant to the protocol before linking.

For ABI fluorescence detection, a preceding peak was often observed and was an artefact due to the detection method the ABI platforms use. Preceding peaks were sometimes skewed and had bases that sloped on the right side towards the real peak. This was especially evident in the specimen control size ladder master mix, where the 96-bp peak had a preceding peak at 84 bp.

In a new microcentrifuge tube, appropriate amount (10 μL for ROX size standards and 9.5 μL for LIZ size standards) of PCR reaction product was mixed with Hi-Di formamide and ROX or LIZ size standards by vortex the mixture well.

In a new 96-well PCR plate, 10 μl of Hi-Di formamide with ROX or LIZ size standards were added to individual wells for each PCR.

1 μL of each PCR reaction product was transferred to the wells containing Hi-Di formamide and ROX or LIZ size standards. Only one sample was added per well and mixed by pipetting up and down. The PCR plate was then capped or covered.

The samples were heat denatured at 95° C. for 2 minutes, and then snap chilled on ice for 5 minutes.

A sample sheet and injection list were prepared for the samples. The samples were run on an ABI 3100/3130 capillary electrophoresis instrument according to its user manual. Data were automatically displayed as size and color specific peaks.

7.3.3. Genomic PCR

Genomic PCR was performed to assess the rearrangement at the TRG and TRD loci. Genomic DNA isolated from the iPSC clones (as described above) was used as a template.

The amplicons were identified on 1% agarose gel electrophoresis. In a second series of experiments, DNA was extracted out of the dominant band on the agarose gel and cloned into a Topo vector and sequenced on a 3730×1 DNA analyzer (cat #3730XL, Thermo Fisher Scientific). Amplicon sequences were analyzed using the BLAST program (blast dot ncbi dot nlm dot nih dot gov/BlastAlign dot cgi) against the human whole genome for sequence homology.

7.4. Example 4: Assessment of SeV Transgenic Presence in γδ T Cell-Derived iPSCs After confirming rearrangements at the TRG and TRD loci in all five clones, the presence of Sendai virus transgenes (SeV Tg) was examined in all clones by RT-PCR as described below. Around passage 10, almost all colonies were negative for SeV vector. This observation was in line with the fact that the high passage colonies will be free of the SeV transgene. RT-PCR primer sequences are summarized in Table 6 below.

TABLE 6

List of RT-PCR Primer Sequences Used

| Primer Pair | Primer name | Sequence |
|---|---|---|
| OCT3/4 | Forward (F) | GACAGGGGGAGGGGAGGAGCTAGG (SEQ ID NO: 38) |
| | Reverse (R) | CTTCCCTCCAACCAGTTGCCCCAAAC (SEQ ID NO: 39) |
| NANOG | Forward (F) | CAGCCCCGATTCTTCCACCAGTCCC (SEQ ID NO: 40) |
| | Reverse (R) | CGGAAGATTCCCAGTCGGGTTCACC (SEQ ID NO: 41) |
| SOX2 | Forward (F) | GGGAAATGGGAGGGGTGCAAAAGAGG (SEQ ID NO: 42) |
| | Reverse (R) | TTGCGTGAGTGTGGATGGGATTGGTG (SEQ ID NO: 43) |
| LIN28 | Forward (F) | TGCACCAGAGTAAGCTGCAC (SEQ ID NO: 44) |
| | Reverse (R) | CTCCTTTTGATCTGCGCTTC (SEQ ID NO: 45) |
| TCR-Vγ9 | Forward (Vγ9) | CGGCACTGTCAGAAAGGAATC (SEQ ID NO: 46) |
| | Reverse (Cγ) | GGCACCGTTAACCAGCTAAA (SEQ ID NO: 47) |
| TCR-Vδ2 | Forward (Vδ2) | ATACCGAGAAAAGGACATCTATG (SEQ ID NO: 48) |
| | Reverse (Cδ) | GACAAAAACGGATGGTTTGG (SEQ ID NO: 49) |
| GAPDH | Forward (F) | ACCACAGTCCATGCCATCAC (SEQ ID NO: 50) |
| | Reverse (R) | TCCACCACCCTGTTGCTGTA (SEQ ID NO: 51) |
| SeV-Tg | Forward (F) | GGATCACTAGGTGATATCGAGC (SEQ ID NO: 52) |
| | Reverse (R) | ACCAGACAAGAGTTTAAGAGATATGTATC (SEQ ID NO: 53) |

7.4.1. RT-PCR

To assess the expression of pluripotent genes (Oct3/4, Nanog, Sox2, Lin28) and to verify the presence or absence of Sendai virus transgene (SeV Tg) among all five iPSC clones, RT-PCR was performed using primers listed in Table 6 above. Total RNA was isolated from iPSC colonies and whole PBMCs using the RNeasy Plus mini kit (cat #74134, Qiagen) pursuant to the manufacturer's instructions. Isolated RNA was quantified on nanodrop. cDNA synthesis was performed using the Primescript 1st strand cDNA synthesis kit (cat #6110B, Takara) pursuant to the manufacturer's instructions.

The resulting cDNA was used as a template for carrying out RT-PCR using primers listed in Table 6 above. At the end of the RT-PCR, amplicons were ran on 1% agarose gel electrophoresis to visualize the bands with DNA ladder at one end. cDNA prepared from whole PBMCs was used as a template negative control and primers against TCRα and TCRβ were used as negative primer controls.

7.5. Example 5: Assessment of Pluripotent Markers in γδ T Cell-Derived iPSCs The pluripotent markers of γδ T-cell derived iPSC colonies were evaluated by RT PCR as described in Section 7.4.1 above (FIG. 7A), by immunohistochemistry as described in Section 7.5.1 (FIG. 7B), and by flow cytometry as described in Section 7.5.2 (FIG. 7C). RT-PCR results showed that these colonies expressed mRNAs that encode pluripotent transcription factors Oct3/4, Nanog, Sox2 and Lin28. Whole PBMCs were used as a negative control to show that the primers are specific against pluripotent markers (RT-PCR primer list and sequence are given in Table 6).

Further supporting these results, immunohistochemistry data confirmed the presence of master transcription factors (Nanog, Oct3/4, Sox2) in all five iPSC colonies (see FIG. 7B). According to FIG. 7B, the expressions of Nanog and Oct3/4 were uniform among all the clones. However, Sox2 was differently expressed in all five clones (varying from 20-40%). Further, as shown in FIG. 7C, flow cytometry data from single suspension of iPSCs clones showed that they expressed high levels of surface SSEA-4 and TRA 1-60 and intranuclear Oct-3, reaffirming the IHC observations. Interestingly, in line with the IHC data, flow cytometry analysis also showed different expression levels of Sox2 among all five clones (FIG. 7C).

7.5.1. Immunohistochemistry (IHC)

Seeding iPSC Onto Coverslips

Coverslips were cut into the desired size and placed in a well of a 24-well plate. Coverslips were then coated with vitronectin by immersing them in 1 mL of PBS containing vitronectin. iPSCs were adapted from feeder condition to feeder free condition. Thus, vitronectin was used to coat the coverslips.

The 24-well plate was incubated at 37° C. for 2 hours. After the incubation period, PBS containing vitronectin was aspirated, and the well was washed with DPBS once. iPSC chunks were immediately plated onto vitronectin coated coverslips in mTeSR culture medium containing 10 μM ROCK inhibitors.

The 24-well plate was incubated in a humidified incubator at 37° C. containing 5% $CO_2$. After 24 hours of culture, culture medium containing ROCK inhibitors was replaced with fresh mTeSR medium without ROCK inhibitors. At this stage, colonies started to attach to the coverslips. No substantial difference was observed even if ROCK inhibitors continued to be used throughout culture.

Culture was further continued for 2 more days with culture medium replenished by fresh medium or until colonies grew to a desired size.

Intranuclear Staining

On the day of IHC staining, culture medium was aspirated from the 24-well plate containing coverslips seeded with iPSC colonies, which were washed twice with 0.5 mL of DPBS.

Coverslips seeded with iPSCs were fixed by incubating them in 200 μL of 4.2% PFA for precisely 2 minutes at room temperature. After the incubation period, PFA was aspirated from the wells containing iPSC colony seeded coverslips. Coverslips containing fixed cells were washed twice with 400 μL of 1×BD Perm wash buffer (cat #51-2091KZ, BD Biosciences).

Blocking was performed by incubating coverslips containing fixed cells in 400 of blocking buffer (10% Donkey serum and 0.35% Triton X-100) at room temperature for 1 hour. After the incubation period, cells were washed once with 400 μL of 1×BD Perm wash buffer.

Cells were then permeabilized by incubating them in 400 μL of 1× Fixation/Permeabilization solution for one hour at 4° C. in a refrigerator. The Fixation/Permeabilization solution was from the eBioscience™ Foxp3/Transcription factor staining buffer set. One part of Fixation/Permeabilization concentrate was diluted using 3 parts of Fixation/Permeabilization diluent. Since Nanog, Oct3/4 and Sox2 are transcription factors, intranuclear permeabilization was used to detect them using the aforesaid reagent. 1×BD Perm wash, instead of the permeabilization buffer from the eBioscience™ Foxp3/Transcription factor staining buffer set, was used due to the existence of mild detergent in the former.

Cells were washed twice with 400 µL of 1×BD Perm wash buffer. Permeabilized cells were stained in 400 µL of wash buffer containing either unconjugated or fluorochrome-conjugated primary antibodies against human Nanog (cat #AF1997, R&D Systems), Oct3/4 (cat #130-117-821, Miltenyi Biotec for fluorochrome-conjugated antibodies and cat #AF1759 for unconjugated antibodies) and Sox2 (cat #130-121-129, Miltenyi Biotec).

The cells were incubated at room temperature for one hour in darkness. After the incubation period, wash buffer containing antibodies was aspirated away and washed the wells twice with 400 µL of wash buffer. If cells were probed with unconjugated primary antibody, fluorochrome-labelled secondary antibody was used to detect the signal. Goat anti-human Oct3/4, Nanog antibodies were unconjugated, while anti-Sox2 was fluorescein isothiocyanate (FITC)-conjugated.

Cells were then stained in 400 µL of wash buffer containing secondary antibodies for one hour at room temperature in darkness.

Anti-goat IgG NorthenLights™ fluorescent 557 conjugated antibodies (cat #NL001, R&D Systems) were used as secondary antibodies in the IHC studies. They are resistant to photobleaching, and thus are ideal for multiplexing IHC studies.

After the incubation period, coverslips containing probed cells were washed twice in 400 µL of 1×BD Perm wash buffer. Coverslips containing fixed and stained cells were recovered from the 24-well plate using fine forceps.

Any remnant wash buffer was drained off from coverslips by pressing one corner of the coverslip against a paper towel. It needed to be ensured that there was no wash buffer drops on the coverslips.

A drop of the VECATSHIELD Antifade mounting medium with DAPI (cat #H-1200, Vector Laboratories)) was added on coverslips containing fixed and stained cells. The coverslip was held with forceps by its corner and inverted in a single motion and mounted on a microscopic slide. The slide with mounted coverslip was allowed to settle for 30 minutes at room temperature in darkness. Paper towel was used to remove the excessive oozed out mounting medium. The edges of the coverslip were sealed with nail polish.

The slide was imaged on Fluorescence microscope (Carl-Zeiss Vert.A1 AXIO). After imaging, sealed slides were stored in a freezer at −20° C. If there was a need to image them again, slides would be thawed at room temperature in darkness for an hour. Water drops formed due to condensation were wiped off and imaging can be performed.

Analysis

Immunohistochemistry (IHC) images were taken on a fluorescence microscope.

Individual channels in images were saved and exported as TIFF format files. TIFF files were exported onto a different computer that contained Image J software. Image J software was used for generating overlay images. Briefly, TIFF images were converted into 8-bit format and the images to be overlaid were selected in the appropriate R, G and B channels. A composite image was generated in RGB color and the image was saved as TIFF/JPEG format file.

7.5.2. Flow Cytometry

For flow cytometry mediated pluripotent markers characterization, iPSC colonies were initially disassociated into singles cells. Cells were spun down in a V-bottom 96-well plate at 1800 rpm for 5 minutes at room temperature. Supernatant was aspirated and the cells pellet was resuspended in 200 µL of DPBS containing 5 µL Live/Dead fixable violet dead cell strain (cat #L34955, Thermo Fisher Scientific) and Anti-Fc antibody.

Cells were incubated at 4° C. for 30 minutes. After the incubation period, cells were spun down at 1800 rpm for 5 minutes at room temperature and washed once with 200 µL of FACS buffer.

For Surface Staining

Cells were surface stained in 100 µL of FACS buffer (DPBS+2% FBS) containing fluorochrome-conjugated antibodies against SSEA-4 (cat #330418, BioLegend), Tra 1-60 (cat #A25617, Thermo Fisher Scientific) for 30 minutes at 4° C. After the incubation period, cells were spun down and FACS buffer (DPBS+2% FBS) containing mAbs was aspirated. Cells were washed twice gently with 200 µL of FACS buffer.

Cells were then fixed by resuspending them in 100 µL of BD Cytofix (cat #554655, BD Biosciences) for 30 minutes at 4° C. in a refrigerator. After the incubation period, cells were spun down at 1800 rpm for 5 min at room temperature and resuspended in 150 µL of FACS buffer.

Flow cytometry data was obtained from the cells on the same day or the day after fixation.

For Intracellular Staining

Cells were permeabilized by incubating them with 200 µL of Fixation/Permeabilization solution for 30 minutes at 4° C. The Fixation/Permeabilization solution was from eBioscience™ Foxp3/Transcription factor staining buffer set. One part of the Fixation/Permeabilization concentrate was diluted using 3 parts of Fixation/Permeabilization diluent.

After the incubation period, the Fixation/Permeabilization solution was aspirated. Cells were washed twice with 200 µL of 1×BD Perm wash buffer.

Cells were then intracellularly probed with 100 µL wash buffer containing fluorochrome-conjugated antibodies against Oct3/4 and Sox2 and incubated at 4° C. for 30 minutes in darkness.

After the incubation period, 100 µL of wash buffer was added to the stained cells to a total volume of 200 µL. Cell were spun down at 1800 rpm for 5 minutes at room temperature. The supernatant was discarded and the cells were washed once with 200 µL of wash buffer. Cells were then resuspended in 150 µL of FACS buffer (DPBS+2% FBS). Flow cytometry data was obtained from the cells on the same day or the day after fixation.

Analysis

For surface phenotype profiling experiments, cells were initially sorted based on FSC-H (Forward Scatter-Height) vs SSC-H (Side Scatter-Height). Live cells were gated in while other cells were eliminated. Next, doublets were eliminated from live cells by gating cells on FSC-A (Forward Scatter-Area) vs FSC-H (Forward Scatter-Height) parameters. Live cells were gated for pluripotent markers like surface expression of SSEA-4 and Tra 1-60 and intracellular expression of Oct3 and Sox2. Fluorescence minus one (FMO) controls were used for each marker to define the specific gate.

7.6. Example 6: Assessment of Genomic Stability of iPSC Clones

To examine genomic stability of these iPSC colonies, such iPSC colonies were subject to karyotyping at passage 19 for Clones A, B and C) and at passage 9 for clones D and E, as described below. As shown in FIGS. 8A-8D, karyotyping of Clones B, C, D and E have normal chromosomal banding pattern by G-band technique, confirming that colonies were normal without any aberrant patterns. Karyotyping data for Clone A was not obtained.

Karyotyping was performed to assess the genomic stability of iPSC colonies. Undifferentiated iPSC colonies were picked from passage 19 and 9 for colonies A, B and C and D and E, respectively, as described above. Single cells were isolated from colonies, added to the StemFit Basic02 medium and sent to Humain Health (Bengaluru, India) for Karyotyping.

7.7. Example 7: Adopting of γδ T-Cell-Derived iPSCs to Feeder-Free Culture Condition As described above in Example 2, no iPSCs colony in feeder free condition was observed during any of the T cell reprogramming experiments. After validating the colonies for Vγ9 and Vδ2 gene rearrangements and pluripotent markers, iPSCs colonies (at passage number 14 for Clones A, B and C and at passage number 4 for Clones D and E) were adopted to feeder-free conditions by testing various combinations of matrix and medium. Surprisingly, after adoption, all colonies were found to maintain and propagate in feeder free condition in vitronectin in combination the mTeSR™ medium (see FIG. 9).

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of producing human induced pluripotent stem cells (iPSCs) comprising:
   a) contacting and culturing an isolated population of cells comprising γδ T cells with an activation culture to activate and enrich Vγ9Vδ2 γδ T cells within the isolated population of cells; wherein the activation culture comprises IL-15 and zoledronic acid;
   b) after step (a), purifying the Vγ9Vδ2-enriched γδ T cells from the isolated population of cells;
   c) transducing the purified Vγ9Vδ2-enriched γδ T cells with a viral vector encoding one or more reprogramming factors; and
   d) culturing the transduced cells under conditions suitable for reprogramming mammalian somatic cells to a pluripotent state, thereby producing iPSCs;
   wherein the produced iPSCs have rearranged TRG and TRD genes;
   wherein the produced iPSCs have TCR rearrangements containing Vγ9 and Vδ2 gene segments;
   wherein optionally the activation culture further comprises IL-2;
   wherein optionally the viral vector is a Sendai virus (SeV) vector;
   wherein optionally the method further comprises obtaining the isolated population of cells from a subject prior to step (a); and
   wherein optionally the isolated population of cells are peripheral blood mononuclear cells (PBMCs).

2. The method of claim 1, wherein the isolated population of cells are cultured in the activation culture for 3 days to 13 days.

3. The method of claim 1, wherein after being cultured in the activation culture in step (a), the isolated population of cells comprises between 5% and 90% γδ T cells; wherein optionally after being cultured in the activation culture in step (a), the isolated population of cells comprises between 5% and 35% γδ T cells.

4. The method of claim 1, wherein the purification step (b) comprises further enriching the Vγ9Vδ2-enriched γδ T cells in the isolated population of cells by cell-cell clump enrichment.

5. The method of claim 1, wherein the one or more reprogramming factors are selected from a group consisting of OCT3/4, SOX2, KLF4, LIN28, and c-Myc.

6. The method of claim 1, wherein in step (d) the transduced cells are cultured in the presence of one or more feeder layers;
   wherein optionally in step (d) the transduced cells are cultured in the presence of a mono layer of feeder layer, and
   wherein optionally the feeder layer comprises mouse embryonic fibroblasts (MEFs).

7. The method of claim 1, wherein the method further comprises isolating the produced iPSCs;
   wherein optionally the method further comprises differentiating the iPSCs ex vivo to cells of a desired cell type; and
   wherein optionally the method further comprises administering the isolated iPSCs or the differentiated cell to a subject.

8. The method of claim 1, wherein the produced iPSCs are negative for a Sendai virus (SeV) vector.

9. The method of claim 1, wherein the produced iPSCs are genomically stable with no loss of a chromosome; wherein optionally the genomic stability of the produced iPSCs is determined by karyotyping analysis.

10. The method of claim 1, wherein the produced iPSCs can grow in feeder free medium after adaptation to the feeder free medium.

11. The method of claim 1, wherein the viral vector is a SeV vector.

12. The method of claim 1, wherein the activation culture further comprises IL-2.

* * * * *

```
                        SEQUENCE LISTING

<160> NUMBER OF SEQ ID NOS: 53

<210> SEQ ID NO 1
<211> LENGTH: 493
<212> TYPE: DNA
<213> ORGANISM: Artificial Sequence
<220> FEATURE:
<223> OTHER INFORMATION: Clone A V Gamma 9 amplicon sequence

<400> SEQUENCE: 1
atgcatgctc gagcggccgc cagtgtgatg gatatctgca gaattcgccc tttgtaatga      60
taagctttgt tccgggacca aataccttga ttttttttgcc caactccagc acctcccaca    120
aggcacagta gtaggtagct atgtcctgtt tctctacatt gtgaatggtg agagtggatg    180
tagacgtttc aggtatccta tccacctcaa atttgcctga cggaatgccg gattcctttc    240
tgacagtgcc gtcatatgaa atggacacca ggaactgtat gacttcacca ggtctctctc    300
gataccaata tacagatgtt gcagaaattg ttattccaga caccacacat tccaggcggg    360
ctgtttttga cagcgtttta gtactggaaa tttgaggttg ctctaggtga cctgcaaggg    420
cgaattccag cacactggcg gccgttacta gtggatccga gctcggtacc aagcttgatg    480
catagcttga gta                                                        493

<210> SEQ ID NO 2
<211> LENGTH: 363
<212> TYPE: DNA
<213> ORGANISM: Artificial Sequence
<220> FEATURE:
<223> OTHER INFORMATION: Clone A V Gamma 9 amplicon sequence for
      alignment

<400> SEQUENCE: 2
tgtaatgata agctttgttc cgggaccaaa taccttgatt ttttttgccca actccagcac     60 ctcccacaag gcacagtagt aggtagctat gtcctgtttc tctacattgt gaatggtgag    120
agtggatgta gacgtttcag gtatcctatc cacctcaaat ttgcctgacg gaatgccgga    180
ttcctttctg acagtgccgt catatgaaat ggacaccagg aactgtatga cttcaccagg    240
tctctctcga taccaatata cagatgttgc agaaattgtt attccagaca ccacacattc    300
caggcgggct gtttttgaca gcgttttagt actggaaatt tgaggttgct ctaggtgacc    360
tgc                                                                    363
```

<210> SEQ ID NO 3
<211> LENGTH: 363
<212> TYPE: DNA
<213> ORGANISM: Homo sapiens
<220> FEATURE:
<223> OTHER INFORMATION: Human V Gamma 9 sequence for alignment

<400> SEQUENCE: 3

```
tgtaatgata agctttgttc cgggaccaaa taccttgatt ttttgccca actcccgcac      60
ctcccacaag gcacagtagt aggtagctat gtcctgtttc tctacattgt gaatggtgag    120
agtggatgta gacgtttcag gtatcctatc cacctcaaat ttgcctgacg gaatgccgga    180
ttcctttctg acagtgccgt catatgaaat ggacaccagg aactgtatga cttcaccagg    240
tctctctcga taccaatata cagatgttgc agaaattgtt attccagaca ccacacattc    300
caggcgggct gtttttgaca gcgttttagt actggaaatt tgaggttgct ctaggtgacc    360
tgc                                                                  363
```

<210> SEQ ID NO 4
<211> LENGTH: 399
<212> TYPE: DNA
<213> ORGANISM: Artificial Sequence
<220> FEATURE:
<223> OTHER INFORMATION: Clone A V Delta 2 amplicon sequence

<400> SEQUENCE: 4

```
agaagggggg cggggccgcc tatgaatgat tcgccagctt ttggtgacct atacaatact     60
cggctatgca tcagcttggt accgatttcg gatccactag taacggccgc cagtgtgctg    120
gaattctccc ttataccgag aaaaggacat ctatggccct ggttacaaag acaatttcca    180
aggtgacatt gatattgccc agaacctggc tgtacttaag atacttgcac catcagagag    240
agatgaaggg tcttactact gtgcctgtga caccgtgggg aacaaaccg ataaactcat     300
ctttggaaaa ggaacccgtt gtgactgtgg aacaagggcg aattctgcag atatccatca    360
cactggcggc cgctcgagca tgcatctaga gggcccaat                           399
```

<210> SEQ ID NO 5
<211> LENGTH: 205
<212> TYPE: DNA
<213> ORGANISM: Artificial Sequence
<220> FEATURE:
<223> OTHER INFORMATION: Clone A V Delta 2 amplicon sequence for
      alignment

<400> SEQUENCE: 5

```
tataccgaga aaaggacatc tatggccctg gttacaaaga caatttccaa ggtgacattg     60
atattgccca gaacctggct gtacttaaga tacttgcacc atcagagaga gatgaagggt    120
cttactactg tgcctgtgac accgtggggg aacaaaccga taaactcatc tttggaaaag    180
gaacccgttg tgactgtgga acaag                                          205
```

<210> SEQ ID NO 6
<211> LENGTH: 208
<212> TYPE: DNA
<213> ORGANISM: Homo sapiens
<220> FEATURE:
<223> OTHER INFORMATION: Human V Delta 2 sequence for alignment

<400> SEQUENCE: 6

```
tataccgaga aaaggacatc tatggccctg gtttcaaaga caatttccaa ggtgacattg     60
atattgcaaa gaacctggct gtacttaaga tacttgcacc atcagagaga gatgaagggt    120
```

```
cttactactg tgcctgtgac accgtggggg ataccgacac cgataaactc atctttggaa    180
aaggaacccg tgtgactgtg gaaccaag                                       208

<210> SEQ ID NO 7
<211> LENGTH: 258
<212> TYPE: DNA
<213> ORGANISM: Artificial Sequence
<220> FEATURE:
<223> OTHER INFORMATION: Clone B V Gamma 9 amplicon sequence

<400> SEQUENCE: 7
gcaacatctg tatattggta tcgagagaga cctggtgaag tcatacagtt cctggtgtcc    60
atttcatatg acggcactgt cagaaaggaa tccggcattc cgtcaggcaa atttgaggtg    120
gataggatac ctgaaacgtc tacatccact ctcaccattc acaatgtaga gaaacaggac    180
atagctacct actactgtgc cttgtgggag acacaagagt tgggcaaaaa aatcaaggta    240
tttggtcccg aacaaag                                                   258

<210> SEQ ID NO 8
<211> LENGTH: 258
<212> TYPE: DNA
<213> ORGANISM: Homo sapiens
<220> FEATURE:
<223> OTHER INFORMATION: Human V Gamma 9 sequence for alignment

<400> SEQUENCE: 8
gcaacatctg tatattggta tcgagagaga cctggtgaag tcatacagtt cctggtgtcc    60
atttcatatg acggcactgt cagaaaggaa tccggcattc cgtcaggcaa atttgaggtg    120
gataggatac ctgaaacgtc tacatccact ctcaccattc acaatgtaga gaaacaggac    180
atagctacct actactgtgc cttgtgggag aaccaagagt tgggcaaaaa aatcaaggta    240
tttggtcccg aacaaag                                                   258

<210> SEQ ID NO 9
<211> LENGTH: 221
<212> TYPE: DNA
<213> ORGANISM: Artificial Sequence
<220> FEATURE:
<223> OTHER INFORMATION: Clone B V Delta 2 amplicon sequence

<400> SEQUENCE: 9
gcccttatac cgagaaaagg acatctatgg ccctggtttc aaagacaatt tccaaggtga    60
cattgatatt gcaagaacc tggctgtact taagatactt gcaccatcag agagagatga     120
agggtcttac tactgtgcct gtgacaccgt aaatggggga tacgcggtca ccgataaact    180
catctttgga aaaggaaccc gtgtgactgt ggaacaaggg c                        221

<210> SEQ ID NO 10
<211> LENGTH: 213
<212> TYPE: DNA
<213> ORGANISM: Artificial Sequence
<220> FEATURE:
<223> OTHER INFORMATION: Clone B V Delta 2 amplicon sequence for
      alignment

<400> SEQUENCE: 10
tataccgaga aaaggacatc tatggcccctg gtttcaaaga caatttccaa ggtgacattg    60
atattgcaaa gaacctggct gtacttaaga tacttgcacc atcagagaga gatgaagggt    120
cttactactg tgcctgtgac accgtaaatg ggggatacgc ggtcaccgat aaactcatct    180
```
ttggaaaagg aacccgtgtg actgtggaac aag 213

<210> SEQ ID NO 11
<211> LENGTH: 217
<212> TYPE: DNA
<213> ORGANISM: Homo sapiens
<220> FEATURE:
<223> OTHER INFORMATION: Human V Delta 2 sequence for alignment

<400> SEQUENCE: 11
tataccgaga aaaggacatc tatggccctg gtttcaaagg caatttccaa ggtgacattg 60
atattgcaaa gaacctggct gtacttaaga tacttgcacc atcagagaga gatgaagggt 120
cttactactg tgcctgtgac accgtagtac tgggggatac gctcgacacc gataaactca 180
tctttggaaa aggaacccgt gtgactgtgg aaccaag 217

<210> SEQ ID NO 12
<211> LENGTH: 820
<212> TYPE: DNA
<213> ORGANISM: Artificial Sequence
<220> FEATURE:
<223> OTHER INFORMATION: Clone C V Gamma 9 amplicon sequence

<400> SEQUENCE: 12
ccagctggcg aaaggggat gtgctgcaag gcgattaagt tgggtaacgc cagggttttc 60
ccagtcacga cgttgtaaaa cgacggccag tgaattgtaa tacgactcac tatagggcga 120
attgggccct ctagatgcat gctcgagcgg ccgccagtgt gatggatatc tgcagaattc 180
aggcctgaat tcgccctttg taatgataag ctttgttccg ggaccaaata ccttgatttt 240
tttgcccaac tcttgtgtct cccacaaggc acagtastas gtagctatgt cctgtttctc 300
tacattgtga atggtgagag tggatgtaga cgtttcaggt atcctatcca cctcaaattt 360
gcctgacgga atgccggatt cctttctgac agtgccgtca tatgaaatgg acaccaggaa 420
ctgtatgact tcaccaggtc tctctcgata ccaatataca gatgttgcag aaattgttat 480
tccagacacc acacattcca ggcgggctgt ttttgacagc gttttagtac tggaaatttg 540
aggttgctct aggtgacctg caagggcgaa ttccagcaca ctggcggccg ttactagtgg 600
atccgagctc ggtaccaagc ttgatgcata gcttgagtat tctatagtgt cacctaaata 660
gcttggcgta atcatggtca tagctgtttt cctgtgtgaa attgttatcc gctcacaatt 720
ccacacaaca tacgagccgg aagcataaag tgtaaagcct ggggtgccta atgagtgagc 780
taactcacat taattgcgtt gcgctcactg cccgctttcc 820

<210> SEQ ID NO 13
<211> LENGTH: 363
<212> TYPE: DNA
<213> ORGANISM: Artificial Sequence
<220> FEATURE:
<223> OTHER INFORMATION: Clone C V Gamma 9 amplicon sequence for
      alignment

<400> SEQUENCE: 13
tgtaatgata agctttgttc cgggaccaaa taccttgatt tttttgccca actcttgtgt 60
ctcccacaag gcacagtast asgtagctat gtcctgtttc tctacattgt gaatggtgag 120
agtggatgta gacgtttcag gtatcctatc cacctcaaat ttgcctgacg gaatgccgga 180
ttcctttctg acagtgccgt catatgaaat ggacaccagg aactgtatga cttcaccagg 240
tctctctcga taccaatata cagatgttgc agaaattgtt attccagaca ccacacattc 300

```
caggcgggct gttttgaca gcgttttagt actggaaatt tgaggttgct ctaggtgacc    360
tgc                                                                363

<210> SEQ ID NO 14
<211> LENGTH: 363
<212> TYPE: DNA
<213> ORGANISM: Homo sapiens
<220> FEATURE:
<223> OTHER INFORMATION: Human V Gamma 9 sequence for alignment

<400> SEQUENCE: 14
tgtaatgata agctttgttc cgggaccaaa taccttgatt ttttttgccca actcttggtt    60 ctcccacaag gcacagtagt aggtagctat gtcctgtttc tctacattgt gaatggtgag   120
agtggatgta gacgtttcag gtatcctatc cacctcaaat ttgcctgacg gaatgccgga   180
ttcctttctg acagtgccgt catatgaaat ggacaccagg aactgtatga cttcaccagg   240
tctctctcga taccaatata cagatgttgc agaaattgtt attccagaca ccacacattc   300
caggcgggct gttttgaca gcgttttagt actggaaatt tgaggttgct ctaggtgacc    360
tgc                                                                363

<210> SEQ ID NO 15
<211> LENGTH: 524
<212> TYPE: DNA
<213> ORGANISM: Artificial Sequence
<220> FEATURE:
<223> OTHER INFORMATION: Clone D V Gamma 9 amplicon sequence

<400> SEQUENCE: 15
atagggcgaa ttgggccctc tagatgcatg ctcgagcggc cgccagtgtg atggatatct    60
gcagaattcg cccttgcagg tcacctagag caacctcaaa tttccagtac taaaacgctg   120
tcaaaaacag cccgcctgga atgtgtggtg tctggaataa caatttctgc aacatctgta   180
tattggtatc gagagagacc tggtgaagtc atacagttcc tggtgtccat ttcatatgac   240
ggcactgtca gaaaggaatc cggcattccg tcaggcaaat ttgaggtgga taggataccc   300
gaaacgtcta catccactct caccattcac aatgtagaga acaggacat agctacctac    360 tactgtgcct tgtgggagtc acaagagttg ggcaaaaaaa tcaaggtatt tggtcccgga   420
acaaagctta tcattacaaa gggcgaattc cagcacactg gcggccgtta ctagtggatc   480
cgagctcggt accaagcttg atgcatagct tgagtattct atag                   524

<210> SEQ ID NO 16
<211> LENGTH: 363
<212> TYPE: DNA
<213> ORGANISM: Artificial Sequence
<220> FEATURE:
<223> OTHER INFORMATION: Clone D V Gamma 9 amplicon sequence for
      alignment

<400> SEQUENCE: 16
gcaggtcacc tagagcaacc tcaaatttcc agtactaaaa cgctgtcaaa aacagcccgc    60
ctggaatgtg tggtgtctgg aataacaatt tctgcaacat ctgtatattg gtatcgagag   120
agacctggtg aagtcataca gttcctggtg tccatttcat atgacggcac tgtcagaaag   180
gaatccggca ttccgtcagg caaatttgag gtggatagga tacctgaaac gtctacatcc   240
actctcacca ttcacaatgt agagaaacag gacatagcta cctactactg tgccttgtgg   300
gagtcacaag agttgggcaa aaaaatcaag gtatttggtc ccggaacaaa gcttatcatt   360
```

```
aca                                                                  363

<210> SEQ ID NO 17
<211> LENGTH: 363
<212> TYPE: DNA
<213> ORGANISM: Homo sapiens
<220> FEATURE:
<223> OTHER INFORMATION: Human V Gamma 9 sequence for alignment

<400> SEQUENCE: 17
gcaggtcacc tagagcaacc tcaaatttcc agtactaaaa cgctgtcaaa aacagcccgc     60
ctggaatgtg tggtgtctgg aataacaatt tctgcaacat ctgtatattg gtatcgagag    120
agacctggtg aagtcataca gttcctggtg tccatttcat atgacggcac tgtcagaaag    180
gaatccggca ttccgtcagg caaatttgag gtggatagga tacctgaaac gtctacatcc    240
actctcacca ttcacaatgt agagaaacag gacatagcta cctactactg tgccttgtgg    300
gagatccaag agttgggcaa aaaaatcaag gtatttggtc ccggaacaaa gcttatcatt    360
aca                                                                  363

<210> SEQ ID NO 18
<211> LENGTH: 360
<212> TYPE: DNA
<213> ORGANISM: Artificial Sequence
<220> FEATURE:
<223> OTHER INFORMATION: Clone D V Delta 2 amplicon sequence

<400> SEQUENCE: 18
ttgggccctc tagatgcatg ctcgagcggc cgccagtgtg atggatatct gcagaattcg     60
cccttatacc gagaaaagga catctatggc cctggtttca agacaatttt ccaaggtgac    120
attgatattg caagaacct ggctgtactt aagatacttg caccatcaga gagagatgaa    180
gggtcttact actgtgcctg tgacacctta cttcctgggg gaccgtacac cgataaactc    240
atctttggaa aggaacccg tgtgactgtg aacaagggc gaattccagc acactggcgg    300
ccgttactag tggatccgag ctcggtacca agcttgatgc atagcttgag tattctatag    360

<210> SEQ ID NO 19
<211> LENGTH: 213
<212> TYPE: DNA
<213> ORGANISM: Artificial Sequence
<220> FEATURE:
<223> OTHER INFORMATION: Clone D V Delta 2 amplicon sequence for
      alignment

<400> SEQUENCE: 19
tataccgaga aaaggacatc tatggccctg gtttcaaaga caatttccaa ggtgacattg     60
atattgcaaa gaacctggct gtacttaaga tacttgcacc atcagagaga gatgaagggt    120
cttactactg tgcctgtgac accttacttc ctgggggacc gtacaccgat aaactcatct    180
ttggaaaagg aacccgtgtg actgtggaac aag                                 213

<210> SEQ ID NO 20
<211> LENGTH: 217
<212> TYPE: DNA
<213> ORGANISM: Homo sapiens
<220> FEATURE:
<223> OTHER INFORMATION: Human V Delta 2 sequence for alignment

<400> SEQUENCE: 20
tataccgaga aaaggacatc tatggccctg gtttcaaaga caatttccaa ggtgacattg     60
```

```
atattgcaaa gaacctggct gtacttaaga tacttgcacc atcagagaga gatgaagggt      120
cttactactg tgcctgtgac accttgcgta ctggggacg actgtacacc gataaactca       180
tctttggaaa aggaacccgt gtgactgtgg aaccaag                               217
```

<210> SEQ ID NO 21
<211> LENGTH: 660
<212> TYPE: DNA
<213> ORGANISM: Artificial Sequence
<220> FEATURE:
<223> OTHER INFORMATION: Clone E V Gamma 9 amplicon sequence

<400> SEQUENCE: 21

```
ggcgaattgg gccctctaga tgcatgctcg agcggccgcc agtgtgatgg atatctgcag       60
aattcgccct tgtaatgat aagctttgtt ccgggaccaa taccttgat ttttttgccc       120 aactcttgta gctcccacaa ggcacagtag taggtagcta tgtcctgttt ctctacattg      180
tgaatggtga gagtggatgt agacgtttca ggtatcctat ccacctcaaa tttgccwgac      240
ggaatgccgg attcctttct gacagtgccg tcatatgaaa tggacaccag gaactgtatg      300
acttcaccag gtctctctcg ataccaatat acagatgttg cagaaattgt tattccagac      360
accacacatt ccaggcgggc tgttttttgac agcgttttag tactggaaat tgaggttgc      420 tctaggtgac ctgcaagggc gaattcaggc ctgaattcca gcacactggc ggccgttact      480
agtggatccg agctcggtac caagcttgat gcatagcttg agtattctat agtgtcacct      540
aaatagcttg gcgtaaatca tggtcatagc tgtttcctgt gtgaaattgt tatccgctca      600
caaattccac acaacatacg agccgaaagc ataaagtgta aagcctgggg tgcctaatga      660
```

<210> SEQ ID NO 22
<211> LENGTH: 363
<212> TYPE: DNA
<213> ORGANISM: Artificial Sequence
<220> FEATURE:
<223> OTHER INFORMATION: Clone E V Gamma 9 amplicon sequence for
      alignment

<400> SEQUENCE: 22

```
tgtaatgata agctttgttc cgggaccaaa taccttgatt ttttgccca actcttgtag        60 ctcccacaag gcacagtagt aggtagctat gtcctgtttc tctacattgt gaatggtgag      120
agtggatgta gacgtttcag gtatcctatc cacctcaaat ttgccwgacg gaatgccgga      180
ttcctttctg acagtgccgt catatgaaat ggacaccagg aactgtatga cttcaccagg      240
tctctctcga taccaatata cagatgttgc agaaattgtt attccagaca ccacacattc      300
caggcgggct gttttttgaca gcgttttagt actggaaatt gaggttgct ctaggtgacc       360 tgc                                                                    363
```

<210> SEQ ID NO 23
<211> LENGTH: 363
<212> TYPE: DNA
<213> ORGANISM: Homo sapiens
<220> FEATURE:
<223> OTHER INFORMATION: Human V Gamma 9 sequence for alignment

<400> SEQUENCE: 23

```
tgtaatgata agctttgttc cgggaccaaa taccttgatt ttttgccca actcttggat        60 ctcccacaag gcacagtagt aggtagctat gtcctgtttc tctacattgt gaatggtgag      120
agtggatgta gacgtttcag gtatcctatc cacctcaaat ttgcctgacg gaatgccgga      180
```

```
ttcctttctg acagtgccgt catatgaaat ggacaccagg aactgtatga cttcaccagg      240
tctctctcga taccaatata cagatgttgc agaaattgtt attccagaca ccacacattc      300
caggcgggct gttttgaca gcgttttagt actggaaatt tgaggttgct ctaggtgacc      360
tgc                                                                   363
```

<210> SEQ ID NO 24
<211> LENGTH: 278
<212> TYPE: DNA
<213> ORGANISM: Artificial Sequence
<220> FEATURE:
<223> OTHER INFORMATION: Clone E V Delta 2 amplicon sequence

<400> SEQUENCE: 24

```
tgggccctct agatgcatgc tcgagcggcc gccagtgtga tggatatctg cagaattcag       60
gcctgaattc gcccttgttc cacagtcaca cgggttcctt ttccaaagat gagtttatcg      120
gtgtacttct accccagta gagtagcagg cacagtatta agaccccttca tctctctctg      180 atggtgcaag tatcttaagt acagccaggt tctttgcaat atcaatgtca ccttggaaat      240
tgtctttgaa accagggcca tagatgtcct tttctcgg                              278
```

<210> SEQ ID NO 25
<211> LENGTH: 205
<212> TYPE: DNA
<213> ORGANISM: Artificial Sequence
<220> FEATURE:
<223> OTHER INFORMATION: Clone E V Delta 2 amplicon sequence for
      alignment

<400> SEQUENCE: 25

```
cttgttccac agtcacacgg gttccttttc caaagatgag tttatcggtg tacttctacc       60
cccagtagag tagcaggcac agtattaaga cccttcatct ctctctgatg gtgcaagtat      120
cttaagtaca gccaggttct ttgcaatatc aatgtcacct tggaaattgt ctttgaaacc      180
agggccatag atgtcctttt ctcgg                                            205
```

<210> SEQ ID NO 26
<211> LENGTH: 207
<212> TYPE: DNA
<213> ORGANISM: Homo sapiens
<220> FEATURE:
<223> OTHER INFORMATION: Human V Delta 2 amplicon sequence

<400> SEQUENCE: 26

```
cttggttcca cagtcacacg gttcctttt ccaaagatga gtttatcggt gttcccttta       60
tcccccagta tgtcacaggc acagtagtaa gaccctttcat ctctctctga tggtgcaagt     120
atcttaagta cagccaggtt ctttgcaata tcaatgtcac cttggaaatt gtctttgaaa      180
ccagggccat agatgtcctt ttctcgg                                          207
```

<210> SEQ ID NO 27
<211> LENGTH: 21
<212> TYPE: DNA
<213> ORGANISM: Artificial Sequence
<220> FEATURE:
<223> OTHER INFORMATION: V Gamma 9 Sense Primer

<400> SEQUENCE: 27

```
cggcactgtc agaaaggaat c                                                21
```

```
<210> SEQ ID NO 28
<211> LENGTH: 23
<212> TYPE: DNA
<213> ORGANISM: Artificial Sequence
<220> FEATURE:
<223> OTHER INFORMATION: V Delta 2 Sense Primer

<400> SEQUENCE: 28
ataccgagaa aaggacatct atg                                               23

<210> SEQ ID NO 29
<211> LENGTH: 25
<212> TYPE: DNA
<213> ORGANISM: Artificial Sequence
<220> FEATURE:
<223> OTHER INFORMATION: JP1/JP2 Anti-sense Primer

<400> SEQUENCE: 29
gaagttacta tgagcttagt ccctt                                             25

<210> SEQ ID NO 30
<211> LENGTH: 24
<212> TYPE: DNA
<213> ORGANISM: Artificial Sequence
<220> FEATURE:
<223> OTHER INFORMATION: JP Anti-sense Primer

<400> SEQUENCE: 30
aagctttgtt ccgggaccaa atac                                              24

<210> SEQ ID NO 31
<211> LENGTH: 24
<212> TYPE: DNA
<213> ORGANISM: Artificial Sequence
<220> FEATURE:
<223> OTHER INFORMATION: J1/J2 Anti-sense Primer

<400> SEQUENCE: 31
tacctgtgac aacaagtgtt gttc                                              24

<210> SEQ ID NO 32
<211> LENGTH: 21
<212> TYPE: DNA
<213> ORGANISM: Artificial Sequence
<220> FEATURE:
<223> OTHER INFORMATION: J Delta 1 Anti-sense Primer

<400> SEQUENCE: 32
gttccacagt cacacgggtt c                                                 21

<210> SEQ ID NO 33
<211> LENGTH: 21
<212> TYPE: DNA
<213> ORGANISM: Artificial Sequence
<220> FEATURE:
<223> OTHER INFORMATION: J Delta 3 Anti-sense Primer

<400> SEQUENCE: 33
ctcacggggc tccacgaaga g                                                 21

<210> SEQ ID NO 34
<211> LENGTH: 20
<212> TYPE: DNA
<213> ORGANISM: Artificial Sequence
<220> FEATURE:
<223> OTHER INFORMATION: TRGV9for
```

<400> SEQUENCE: 34
gcaggtcacc tagagcaacc                                                  20

<210> SEQ ID NO 35
<211> LENGTH: 20
<212> TYPE: DNA
<213> ORGANISM: Artificial Sequence
<220> FEATURE:
<223> OTHER INFORMATION: TRGJPrev

<400> SEQUENCE: 35
tgtaatgata agctttgttc                                                  20

<210> SEQ ID NO 36
<211> LENGTH: 23
<212> TYPE: DNA
<213> ORGANISM: Artificial Sequence
<220> FEATURE:
<223> OTHER INFORMATION: TCRV Delta 2_Fwd P10

<400> SEQUENCE: 36
ataccgagaa aaggacatct atg                                              23

<210> SEQ ID NO 37
<211> LENGTH: 21
<212> TYPE: DNA
<213> ORGANISM: Artificial Sequence
<220> FEATURE:
<223> OTHER INFORMATION: TCRJ Delta 1_Rev P10

<400> SEQUENCE: 37
gttccacagt cacacgggtt c                                                21

<210> SEQ ID NO 38
<211> LENGTH: 24
<212> TYPE: DNA
<213> ORGANISM: Artificial Sequence
<220> FEATURE:
<223> OTHER INFORMATION: OCT3/4 Forward (F)

<400> SEQUENCE: 38
gacaggggga ggggaggagc tagg                                             24

<210> SEQ ID NO 39
<211> LENGTH: 26
<212> TYPE: DNA
<213> ORGANISM: Artificial Sequence
<220> FEATURE:
<223> OTHER INFORMATION: OCT3/4 Reverse (R)

<400> SEQUENCE: 39
cttccctcca accagttgcc ccaaac                                           26

<210> SEQ ID NO 40
<211> LENGTH: 25
<212> TYPE: DNA
<213> ORGANISM: Artificial Sequence
<220> FEATURE:
<223> OTHER INFORMATION: NANOG Forward (F)

<400> SEQUENCE: 40
cagccccgat tcttccacca gtccc                                            25

<210> SEQ ID NO 41
<211> LENGTH: 25

```
<212> TYPE: DNA
<213> ORGANISM: Artificial Sequence
<220> FEATURE:
<223> OTHER INFORMATION: NANOG Reverse (R)

<400> SEQUENCE: 41
cggaagattc ccagtcgggt tcacc                                          25

<210> SEQ ID NO 42
<211> LENGTH: 26
<212> TYPE: DNA
<213> ORGANISM: Artificial Sequence
<220> FEATURE:
<223> OTHER INFORMATION: SOX2 Forward (F)

<400> SEQUENCE: 42
gggaaatggg aggggtgcaa aagagg                                         26

<210> SEQ ID NO 43
<211> LENGTH: 26
<212> TYPE: DNA
<213> ORGANISM: Artificial Sequence
<220> FEATURE:
<223> OTHER INFORMATION: SOX2 Reverse (R)

<400> SEQUENCE: 43
ttgcgtgagt gtggatggga ttggtg                                         26

<210> SEQ ID NO 44
<211> LENGTH: 20
<212> TYPE: DNA
<213> ORGANISM: Artificial Sequence
<220> FEATURE:
<223> OTHER INFORMATION: LIN28 Forward (F)

<400> SEQUENCE: 44
tgcaccagag taagctgcac                                                20

<210> SEQ ID NO 45
<211> LENGTH: 20
<212> TYPE: DNA
<213> ORGANISM: Artificial Sequence
<220> FEATURE:
<223> OTHER INFORMATION: LIN28 Reverse (R)

<400> SEQUENCE: 45 ctcctttga tctgcgcttc                                                 20

<210> SEQ ID NO 46
<211> LENGTH: 21
<212> TYPE: DNA
<213> ORGANISM: Artificial Sequence
<220> FEATURE:
<223> OTHER INFORMATION: TCR-V Gamma 9 Forward (V Gamma 9)

<400> SEQUENCE: 46
cggcactgtc agaaaggaat c                                              21

<210> SEQ ID NO 47
<211> LENGTH: 20
<212> TYPE: DNA
<213> ORGANISM: Artificial Sequence
<220> FEATURE:
<223> OTHER INFORMATION: TCR-V Gamma 9 Reverse (C Gamma)

<400> SEQUENCE: 47
```
ggcaccgtta accagctaaa                    20

<210> SEQ ID NO 48
<211> LENGTH: 23
<212> TYPE: DNA
<213> ORGANISM: Artificial Sequence
<220> FEATURE:
<223> OTHER INFORMATION: TCR-V Delta 2 Forward (V Delta 2)

<400> SEQUENCE: 48
ataccgagaa aaggacatct atg                23

<210> SEQ ID NO 49
<211> LENGTH: 20
<212> TYPE: DNA
<213> ORGANISM: Artificial Sequence
<220> FEATURE:
<223> OTHER INFORMATION: TCR-V Delta 2 Reverse (C Delta)

<400> SEQUENCE: 49
gacaaaaacg gatggtttgg                    20

<210> SEQ ID NO 50
<211> LENGTH: 20
<212> TYPE: DNA
<213> ORGANISM: Artificial Sequence
<220> FEATURE:
<223> OTHER INFORMATION: GAPDH Forward (F)

<400> SEQUENCE: 50
accacagtcc atgccatcac                    20

<210> SEQ ID NO 51
<211> LENGTH: 20
<212> TYPE: DNA
<213> ORGANISM: Artificial Sequence
<220> FEATURE:
<223> OTHER INFORMATION: GAPDH Reverse (R)

<400> SEQUENCE: 51
tccaccaccc tgttgctgta                    20

<210> SEQ ID NO 52
<211> LENGTH: 22
<212> TYPE: DNA
<213> ORGANISM: Artificial Sequence
<220> FEATURE:
<223> OTHER INFORMATION: SeV-Tg Forward (F)

<400> SEQUENCE: 52
ggatcactag gtgatatcga gc                 22

<210> SEQ ID NO 53
<211> LENGTH: 29
<212> TYPE: DNA
<213> ORGANISM: Artificial Sequence
<220> FEATURE:
<223> OTHER INFORMATION: SeV-Tg Reverse (R)

<400> SEQUENCE: 53
accagacaag agtttaagag atatgtatc          29